United States Patent
Njikang et al.

(10) Patent No.: US 9,408,797 B2
(45) Date of Patent: *Aug. 9, 2016

(54) DERMAL FILLER COMPOSITIONS FOR FINE LINE TREATMENT

(75) Inventors: Gabriel N. Njikang, Orcutt, CA (US); Futian Liu, Sunnyvale, CA (US); Xiaojie Yu, Irvine, CA (US); Nicholas J. Manesis, Ramona, CA (US); Sumit Paliwal, Goleta, CA (US)

(73) Assignee: Allergan, Inc., Irvine, CA (US)

( * ) Notice: Subject to any disclaimer, the term of this patent is extended or adjusted under 35 U.S.C. 154(b) by 158 days.

This patent is subject to a terminal disclaimer.

(21) Appl. No.: 13/615,193

(22) Filed: Sep. 13, 2012

(65) Prior Publication Data

US 2013/0203696 A1 Aug. 8, 2013

Related U.S. Application Data

(63) Continuation-in-part of application No. 13/593,313, filed on Aug. 23, 2012, which is a continuation-in-part of application No. 13/486,754, filed on Jun. 1, 2012.

(60) Provisional application No. 61/534,780, filed on Sep. 14, 2011, provisional application No. 61/493,309, filed on Jun. 3, 2011.

(51) Int. Cl.
*A61K 8/73* (2006.01)
*A61Q 19/08* (2006.01)
*A61K 8/33* (2006.01)

(52) U.S. Cl.
CPC ... *A61K 8/73* (2013.01); *A61K 8/33* (2013.01); *A61K 8/735* (2013.01); *A61Q 19/08* (2013.01); *A61K 2800/262* (2013.01); *A61K 2800/95* (2013.01)

(58) Field of Classification Search
CPC ..... A61K 8/735; A61K 8/676; A61K 8/4993; A61Q 19/08
See application file for complete search history.

(56) References Cited

U.S. PATENT DOCUMENTS

| | | |
|---|---|---|
| 2,128,827 A | 8/1938 | Killian |
| 3,548,056 A | 12/1970 | Eigen et al. |
| 3,763,009 A | 10/1973 | Suzuki |
| 3,949,073 A | 4/1976 | Daniels et al. |
| 4,060,081 A | 11/1977 | Yannas et al. |
| 4,140,537 A | 2/1979 | Luck et al. |
| 4,233,360 A | 11/1980 | Luck et al. |
| 4,273,705 A | 6/1981 | Kato |
| 4,279,812 A | 7/1981 | Cioca |
| 4,424,208 A | 1/1984 | Wallace et al. |
| 4,501,306 A | 2/1985 | Chu et al. |
| 4,582,640 A | 4/1986 | Smestad et al. |
| 4,582,865 A | 4/1986 | Balazs et al. |
| 4,605,691 A | 8/1986 | Balazs et al. |
| 4,636,524 A | 1/1987 | Balazs |
| 4,642,117 A | 2/1987 | Nguyen et al. |
| 4,713,448 A | 12/1987 | Balazs |
| 4,716,154 A | 12/1987 | Malson et al. |
| 4,772,419 A | 9/1988 | Malson et al. |
| 4,803,075 A | 2/1989 | Wallace et al. |
| 4,886,787 A | 12/1989 | De Belder et al. |
| 4,896,787 A | 1/1990 | Delamour et al. |
| 5,009,013 A | 4/1991 | Wiklund |
| 5,087,446 A | 2/1992 | Suzuki et al. |
| 5,091,171 A | 2/1992 | Yu et al. |
| 5,137,723 A | 8/1992 | Yamamoto et al. |
| 5,143,724 A | 9/1992 | Leshchiner et al. |
| 5,246,698 A | 9/1993 | Leshchiner et al. |
| 5,314,874 A | 5/1994 | Miyata et al. |
| 5,328,955 A | 7/1994 | Rhee et al. |
| 5,356,883 A | 10/1994 | Kuo et al. |
| 5,399,351 A | 3/1995 | Leshchiner et al. |
| 5,428,024 A | 6/1995 | Chu et al. |
| 5,531,716 A | 7/1996 | Luzio et al. |
| 5,565,519 A | 10/1996 | Rhee et al. |
| 5,571,503 A | 11/1996 | Mausner |
| 5,614,587 A | 3/1997 | Rhee et al. |
| 5,616,568 A | 4/1997 | Pouyani et al. |
| 5,616,611 A | 4/1997 | Yamamoto |
| 5,616,689 A | 4/1997 | Shenoy et al. |
| 5,633,001 A | 5/1997 | Agerup |
| 5,643,464 A | 7/1997 | Rhee et al. |
| 5,676,964 A | 10/1997 | della Valle |
| 5,823,671 A | 10/1998 | Mitchell et al. |
| 5,824,333 A | 10/1998 | Scopelianos et al. |
| 5,827,529 A | 10/1998 | Ono et al. |

(Continued)

FOREIGN PATENT DOCUMENTS

| | | |
|---|---|---|
| CA | 949965 | 6/1974 |
| CN | 101002725 A | 7/2007 |

(Continued)

OTHER PUBLICATIONS

Lemperle, G. et al., Plastic and Reconstructive Surgery, "A Classification of Facial Wri", Nov. 2001, vol. 108, No. 6, pp. 1735-1750.*
Laeschke, "Biocompatibility of Microparticles into Soft Tissue Fillers", 23 Semin. Cutan. Med. Surg., 214 (2004).
Lamar et al., "Antifibrosis Effect of Novel Gels in Anterior Ciliary Sclerotomy *ACS)," ARVO 2002 abstract.
Levy, Jaime et al., "Lidocaine hypersensitivity after subconjunctival injection", Can J Ophthalmol 2006; 41:204-6.
Lindvall et al.; "Influence of Various Compunds on the Degradation of Hyaluronic Acid by a Myeloperoxidase System"; Chemico-Biological Interactions; vol. 90; pp. 1-12; 1994.

(Continued)

*Primary Examiner* — Layla Berry
*Assistant Examiner* — Bahar Craigo
(74) *Attorney, Agent, or Firm* — Barbara C. Potts

(57) ABSTRACT

The present invention provides highly injectable, long-lasting hyaluronic acid-based hydrogel dermal filler compositions which are particularly advantageous for correction of fine lines in the face.

16 Claims, 9 Drawing Sheets

(56) References Cited

U.S. PATENT DOCUMENTS

| | | |
|---|---|---|
| 5,843,907 A | 12/1998 | Sakai |
| 5,880,107 A | 3/1999 | Buenter |
| 5,886,042 A | 3/1999 | Yu et al. |
| 5,935,164 A | 8/1999 | Iversen |
| 5,972,326 A | 10/1999 | Galin et al. |
| 5,980,930 A | 11/1999 | Fenton et al. |
| 5,985,850 A | 11/1999 | Falk et al. |
| 6,013,679 A | 1/2000 | Kuo et al. |
| 6,066,325 A | 5/2000 | Wallace et al. |
| 6,147,054 A | 11/2000 | De Paoli Ambrosi |
| 6,224,857 B1 | 5/2001 | Romeo et al. |
| 6,335,035 B1 | 1/2002 | Drizen et al. |
| 6,372,494 B1 | 4/2002 | Naughton et al. |
| 6,383,218 B1 | 5/2002 | Sourdille et al. |
| 6,383,219 B1 | 5/2002 | Telandro et al. |
| 6,418,934 B1 | 7/2002 | Chin |
| 6,495,148 B1 | 12/2002 | Abbiati |
| 6,521,223 B1 | 2/2003 | Calias et al. |
| 6,544,503 B1 | 4/2003 | Vanderhoff et al. |
| 6,627,620 B1 | 9/2003 | Nielsen |
| 6,630,486 B1 | 10/2003 | Royer |
| 6,685,963 B1 | 2/2004 | Taupin et al. |
| 6,716,251 B1 | 4/2004 | Asius et al. |
| 6,734,298 B1 | 5/2004 | Barbucci |
| 6,767,924 B2 | 7/2004 | Yu et al. |
| 6,767,928 B1 | 7/2004 | Murphy et al. |
| 6,852,255 B2 | 2/2005 | Yang |
| 6,893,466 B2 | 5/2005 | Trieu |
| 6,903,199 B2 | 6/2005 | Moon |
| 6,921,819 B2 | 7/2005 | Piron et al. |
| 6,924,273 B2 | 8/2005 | Pierce |
| 6,939,562 B2 | 9/2005 | Spiro et al. |
| 6,979,440 B2 | 12/2005 | Shefer et al. |
| 7,119,062 B1 | 10/2006 | Alvis et al. |
| 7,166,570 B2 | 1/2007 | Hunter et al. |
| 7,192,984 B2 | 3/2007 | Berg |
| 7,196,180 B2 | 3/2007 | Aeschlimann |
| 7,214,667 B2 | 5/2007 | Fukuda et al. |
| 7,314,636 B2 | 1/2008 | Caseres et al. |
| 7,491,709 B2 | 2/2009 | Carey |
| 7,635,592 B2 * | 12/2009 | West et al. ............... 435/395 |
| 7,741,476 B2 | 6/2010 | Lebreton |
| 7,902,171 B2 | 3/2011 | Reinmuller et al. |
| 8,052,990 B2 | 11/2011 | Hermitte et al. |
| 8,124,120 B2 | 2/2012 | Sadozai |
| 8,303,941 B2 | 11/2012 | Musumeci |
| 8,318,695 B2 | 11/2012 | Stroumpoulis et al. |
| 8,338,375 B2 | 12/2012 | Schroeder et al. |
| 8,338,388 B2 | 12/2012 | Lebreton |
| 8,357,795 B2 | 1/2013 | Lebreton |
| 8,394,782 B2 | 3/2013 | Stroumpoulis |
| 8,394,783 B2 | 3/2013 | Stroumpoulis |
| 8,394,784 B2 | 3/2013 | Stroumpoulis |
| 8,455,465 B2 | 6/2013 | Molliard |
| 8,513,216 B2 | 8/2013 | Stroumpoulis |
| 8,524,213 B2 | 9/2013 | Leshchiner et al. |
| 8,563,532 B2 | 10/2013 | Lebreton |
| 8,575,129 B2 | 11/2013 | Bellini |
| 8,586,562 B2 | 11/2013 | Lebreton |
| 8,853,184 B2 | 10/2014 | Stroumpoulis |
| 8,895,532 B2 | 11/2014 | Bresin et al. |
| 8,945,523 B2 | 2/2015 | Patel Framroze |
| 8,946,192 B2 | 2/2015 | Gousse et al. |
| 9,023,369 B2 | 5/2015 | Malessa et al. |
| 2002/0102311 A1 | 8/2002 | Gustavsson et al. |
| 2002/0106793 A1 | 8/2002 | West et al. |
| 2002/0160109 A1 | 10/2002 | Yeo et al. |
| 2003/0031638 A1 | 2/2003 | Joshi et al. |
| 2003/0093157 A1 | 5/2003 | Casares et al. |
| 2003/0119985 A1 | 6/2003 | Sehl et al. |
| 2003/0148995 A1 | 8/2003 | Piron et al. |
| 2004/0032056 A1 | 2/2004 | Vang et al. |
| 2004/0101959 A1 | 5/2004 | Marko et al. |
| 2004/0127698 A1 | 7/2004 | Tsai et al. |
| 2004/0127699 A1 | 7/2004 | Zhao et al. |
| 2004/0199241 A1 | 10/2004 | Gravett et al. |
| 2004/0265389 A1 | 12/2004 | Yui et al. |
| 2005/0101582 A1 | 5/2005 | Lyons et al. |
| 2005/0136122 A1 | 6/2005 | Sadozai et al. |
| 2005/0142152 A1 | 6/2005 | Leshchiner et al. |
| 2005/0181007 A1 | 8/2005 | Hunter |
| 2005/0186261 A1 | 8/2005 | Avelar |
| 2005/0186673 A1 | 8/2005 | Geistlich et al. |
| 2005/0226936 A1 | 10/2005 | Agerup |
| 2005/0266064 A1 | 12/2005 | McCarthy |
| 2005/0271729 A1 | 12/2005 | Wang |
| 2005/0277617 A1 | 12/2005 | Fukuda et al. |
| 2005/0281880 A1 | 12/2005 | Wang |
| 2005/0287180 A1 | 12/2005 | Chen |
| 2006/0040894 A1 | 2/2006 | Hunter et al. |
| 2006/0095137 A1 | 5/2006 | Chung et al. |
| 2006/0122147 A1 | 6/2006 | Wohlrab |
| 2006/0141049 A1 | 6/2006 | Lyons et al. |
| 2006/0147483 A1 | 7/2006 | Chaouk et al. |
| 2006/0189516 A1 | 8/2006 | Yang |
| 2006/0194758 A1 | 8/2006 | Lebreton |
| 2006/0246137 A1 | 11/2006 | Hermitte et al. |
| 2006/0257488 A1 | 11/2006 | Hubbard |
| 2006/0286769 A1 | 12/2006 | Tsuchiya et al. |
| 2007/0026070 A1 | 2/2007 | Vonwiller et al. |
| 2007/0066816 A1 | 3/2007 | Tsai et al. |
| 2007/0077292 A1 | 4/2007 | Pinsky |
| 2007/0129430 A1 | 6/2007 | Miyata et al. |
| 2007/0178121 A1 | 8/2007 | First et al. |
| 2007/0203095 A1 | 8/2007 | Sadozai et al. |
| 2007/0212385 A1 | 9/2007 | David |
| 2007/0224247 A1 | 9/2007 | Chudzik |
| 2007/0224278 A1 | 9/2007 | Lyons et al. |
| 2007/0298005 A1 | 12/2007 | Thibault |
| 2008/0044476 A1 | 2/2008 | Lyons et al. |
| 2008/0057091 A1 | 3/2008 | Abdellaoui |
| 2008/0089918 A1 | 4/2008 | Lebreton |
| 2008/0188416 A1 | 8/2008 | Bernstein |
| 2008/0193538 A1 | 8/2008 | Kitazono et al. |
| 2008/0200430 A1 | 8/2008 | Biterman et al. |
| 2008/0207794 A1 | 8/2008 | Wright et al. |
| 2008/0241252 A1 | 10/2008 | Lyons |
| 2008/0268051 A1 | 10/2008 | Lyons |
| 2008/0274946 A1 | 11/2008 | Gimpapa |
| 2008/0279806 A1 | 11/2008 | Cho |
| 2008/0293637 A1 | 11/2008 | Schroeder et al. |
| 2009/0017091 A1 | 1/2009 | Daniloff et al. |
| 2009/0018102 A1 | 1/2009 | Moutet |
| 2009/0022808 A1 | 1/2009 | Championn |
| 2009/0028817 A1 | 1/2009 | Niklason et al. |
| 2009/0036403 A1 | 2/2009 | Stroumpoulis et al. |
| 2009/0042834 A1 | 2/2009 | Karageozian et al. |
| 2009/0093755 A1 | 4/2009 | Schroeder et al. |
| 2009/0110671 A1 | 4/2009 | Miyata et al. |
| 2009/0110736 A1 | 4/2009 | Boutros |
| 2009/0143331 A1 | 6/2009 | Stroumpoulis et al. |
| 2009/0143348 A1 | 6/2009 | Tezel et al. |
| 2009/0148527 A1 | 6/2009 | Robinson |
| 2009/0155314 A1 | 6/2009 | Tezel |
| 2009/0155362 A1 | 6/2009 | Longin |
| 2009/0169615 A1 | 7/2009 | Pinsky |
| 2009/0263447 A1 | 10/2009 | Asius et al. |
| 2009/0291986 A1 | 11/2009 | Pappas et al. |
| 2009/0297632 A1 | 12/2009 | Waugh |
| 2010/0004198 A1 | 1/2010 | Stroumpoulis et al. |
| 2010/0028437 A1 | 2/2010 | Lebreton |
| 2010/0035838 A1 | 2/2010 | Herber et al. |
| 2010/0041788 A1 | 2/2010 | Voigts et al. |
| 2010/0098764 A1 | 4/2010 | Stroumpoulis et al. |
| 2010/0098794 A1 | 4/2010 | Armand |
| 2010/0099623 A1 | 4/2010 | Schroeder et al. |
| 2010/0111919 A1 | 5/2010 | Abuzaina et al. |
| 2010/0136070 A1 | 6/2010 | Dobak et al. |
| 2010/0226988 A1 | 9/2010 | Lebreton |
| 2010/0255068 A1 | 10/2010 | Stroumpoulis et al. |
| 2010/0273747 A1 | 10/2010 | Malessa et al. |
| 2010/0316683 A1 | 12/2010 | Piron |
| 2010/0323985 A1 | 12/2010 | Moutet et al. |
| 2011/0034684 A1 | 2/2011 | Yokokawa |

(56) References Cited

U.S. PATENT DOCUMENTS

| | | |
|---|---|---|
| 2011/0077737 A1 | 3/2011 | Stroumpoulis et al. |
| 2011/0118206 A1 | 5/2011 | Lebreton |
| 2011/0171286 A1 | 7/2011 | Cecile et al. |
| 2011/0171310 A1 | 7/2011 | Gousse et al. |
| 2011/0171311 A1 | 7/2011 | Gousse et al. |
| 2011/0172180 A1 | 7/2011 | Gousse et al. |
| 2011/0201571 A1 | 8/2011 | Gavard Molliard |
| 2011/0229574 A1 | 9/2011 | Guillen et al. |
| 2011/0250276 A1 | 10/2011 | Fournial et al. |
| 2011/0263521 A1 | 10/2011 | Moutet et al. |
| 2012/0010146 A1 | 1/2012 | Han et al. |
| 2012/0034462 A1 | 2/2012 | Stroumpoulis et al. |
| 2012/0071437 A1 | 3/2012 | Stroumpoulis et al. |
| 2012/0095206 A1 | 4/2012 | Chen |
| 2012/0100217 A1 | 4/2012 | Green |
| 2012/0164098 A1 | 6/2012 | Schroeder et al. |
| 2012/0172328 A1 | 7/2012 | Lebreton |
| 2012/0189589 A1 | 7/2012 | Van Epps et al. |
| 2012/0189590 A1 | 7/2012 | Van Epps et al. |
| 2012/0189591 A1 | 7/2012 | Van Epps et al. |
| 2012/0189708 A1 | 7/2012 | Van Epps et al. |
| 2012/0190644 A1 | 7/2012 | D'este |
| 2012/0208890 A1 | 8/2012 | Gousse et al. |
| 2012/0225842 A1 | 9/2012 | Cecile et al. |
| 2012/0232030 A1 | 9/2012 | Gousse et al. |
| 2012/0283428 A1 | 11/2012 | Lee et al. |
| 2013/0023658 A1 | 1/2013 | Stroumpoulis et al. |
| 2013/0041038 A1 | 2/2013 | Lebreton |
| 2013/0041039 A1 | 2/2013 | Lebreton |
| 2013/0072453 A1 | 3/2013 | Gousse et al. |
| 2013/0096081 A1 | 4/2013 | Njikang |
| 2013/0116188 A1 | 5/2013 | Pollock et al. |
| 2013/0116190 A1 | 5/2013 | Pollock et al. |
| 2013/0116411 A1 | 5/2013 | Pollock et al. |
| 2013/0123210 A1 | 5/2013 | Liu |
| 2013/0131011 A1 | 5/2013 | Lebreton |
| 2013/0136780 A1 | 5/2013 | Tezel et al. |
| 2013/0203696 A1 | 8/2013 | Liu |
| 2013/0209532 A1 | 8/2013 | Stroumpoulis et al. |
| 2013/0210760 A1 | 8/2013 | Liu |
| 2013/0237615 A1 | 9/2013 | Meunier |
| 2013/0244943 A1 | 9/2013 | Yu et al. |
| 2013/0244970 A1 | 9/2013 | Lebreton |
| 2013/0274222 A1 | 10/2013 | Home |
| 2014/0011980 A1 | 1/2014 | Chitre et al. |
| 2014/0011990 A1 | 1/2014 | Lebreton |
| 2014/0039061 A1 | 2/2014 | Wiebensjo et al. |
| 2014/0088037 A1 | 3/2014 | Bon Betemps et al. |
| 2015/0151858 A1 | 6/2015 | Turzi |

FOREIGN PATENT DOCUMENTS

| | | |
|---|---|---|
| DE | 20221171 U1 | 6/2005 |
| EP | 0273823 | 7/1988 |
| EP | 0416250 | 3/1991 |
| EP | 0416846 | 3/1991 |
| EP | 0637450 A2 | 2/1995 |
| EP | 1247522 | 10/2002 |
| EP | 1419792 | 4/2003 |
| EP | 1398131 | 3/2004 |
| EP | 1532991 | 5/2005 |
| EP | 1726299 | 11/2006 |
| EP | 2236523 | 10/2010 |
| EP | 2484387 A1 | 8/2012 |
| EP | 2670447 B1 | 12/2013 |
| EP | 2676658 B1 | 12/2013 |
| FR | 2733427 | 10/1996 |
| FR | 2920000 | 2/2009 |
| FR | 2924615 | 6/2009 |
| JP | 55-153711 | 11/1980 |
| JP | 2002020259 | 1/2002 |
| JP | 2002080501 | 3/2002 |
| JP | 2007043960 | 2/2007 |
| JP | 2007063177 | 3/2007 |
| WO | 8600079 | 1/1986 |
| WO | 8600912 | 2/1986 |
| WO | 9104058 A2 | 4/1991 |
| WO | 9200105 | 1/1992 |
| WO | 9220349 | 11/1992 |
| WO | 9401468 | 1/1994 |
| WO | 9402517 | 2/1994 |
| WO | 9633751 | 1/1996 |
| WO | 9704012 | 2/1997 |
| WO | 9835639 | 8/1998 |
| WO | 9835640 | 8/1998 |
| WO | 0001428 | 1/2000 |
| WO | 0008061 A1 | 2/2000 |
| WO | 0179342 | 10/2001 |
| WO | 0205753 | 1/2002 |
| WO | 0206350 | 1/2002 |
| WO | 0209792 | 2/2002 |
| WO | 02017713 | 3/2002 |
| WO | 03007782 | 1/2003 |
| WO | 2004020473 | 3/2004 |
| WO | 2004022603 | 3/2004 |
| WO | 2004073759 | 9/2004 |
| WO | 2004092223 | 10/2004 |
| WO | 2005040224 | 5/2005 |
| WO | 2005067944 | 7/2005 |
| WO | 2005074913 | 8/2005 |
| WO | 2005112888 | 12/2005 |
| WO | 2006020994 A2 | 2/2006 |
| WO | 2006023645 | 3/2006 |
| WO | 2006067608 | 6/2006 |
| WO | 2007004300 A1 | 1/2007 |
| WO | 2007018124 | 2/2007 |
| WO | 2007070617 | 6/2007 |
| WO | 2007077399 | 7/2007 |
| WO | 2007128923 | 11/2007 |
| WO | 2007136738 | 11/2007 |
| WO | 2008015249 A2 | 2/2008 |
| WO | 2008034176 | 3/2008 |
| WO | 2008068297 | 6/2008 |
| WO | 2008072230 | 6/2008 |
| WO | 2008077172 | 7/2008 |
| WO | 2008078154 A2 | 7/2008 |
| WO | 2008098019 | 8/2008 |
| WO | 2008139122 | 11/2008 |
| WO | 2008140665 A2 | 11/2008 |
| WO | 2008148967 | 12/2008 |
| WO | 2008157608 | 12/2008 |
| WO | 2009024350 A2 | 2/2009 |
| WO | 2009024677 A2 | 2/2009 |
| WO | 2009024719 | 2/2009 |
| WO | 2009026158 | 2/2009 |
| WO | 2009028764 | 3/2009 |
| WO | 2009034559 | 3/2009 |
| WO | 2009073437 | 6/2009 |
| WO | 2009073508 A2 | 6/2009 |
| WO | 2010003797 | 1/2010 |
| WO | 2010015900 | 2/2010 |
| WO | 2010027471 | 3/2010 |
| WO | 2010028025 | 3/2010 |
| WO | 2010029344 | 3/2010 |
| WO | 2010038771 | 4/2010 |
| WO | 2010051641 | 5/2010 |
| WO | 2010052430 | 5/2010 |
| WO | 2010053918 | 5/2010 |
| WO | 2010061005 | 6/2010 |
| WO | 2011059909 A1 | 5/2011 |
| WO | 2011086458 A1 | 7/2011 |
| WO | 2012/077055 | 6/2012 |
| WO | 2012104419 A1 | 8/2012 |
| WO | 2014026161 A2 | 2/2014 |
| WO | 2014032804 A1 | 3/2014 |

OTHER PUBLICATIONS

Lupo, MP., "Hyaluronic acid fillers in facial rejuvenation." Semin. Cutan. Med. Surg. 25(3): 122-126 (2006).

Mackley, et al., "Delayed-Type Hypersensitivity to Lidocaine", Arch Dermatol, vol. 139, Mar. 2003, pp. 343-346.

Mancinelli et al., "Intramuscular High-Dose Triamcinolone Acetonide in the Treatment of Severe Chronic Asthma", West J. Med, Nov. 1997: 167(5), 322-329.

(56) References Cited

OTHER PUBLICATIONS

Matsumoto, Alan H, et al., "Reducing the Discomfort of Lidocaine Administration through pH Buffering," Journal of Vascular and Interventional Radiology, Jan.-Feb. 1994, pp. 171-175.
McCarty et al., "Inflammatory Reaction After Intrasynovial Injection of Microcrystalline Adrenocorticosteroid Esters", Arthritis and Rheumatism, 7(4):359-367 (1964).
McCleland, Plastic Reconstructive Surgery, 100(6), Nov. 1997, pp. 1466-1474.
McPherson, John M., "Development and Biochemical Characterization of Injectable Collagen," J. Dermatol Surg Oncol, 14 (Suppl1):Jul. 7, 1988, pp. 13-20.
Millay et al.; "Vasoconstrictors in Facial Plastic Surgery"; Archives of Otolaryngology-Head & Neck Surgery; vol. 117; pp. 160-163; Feb. 1991.
Orvisky, E., et al., "High-molecular-weight hyaluronan—a valuable tool in testing the antioxidative activity of amphiphilic drugs stobadine and vinpocetine," Pharm.Biomed.Anal. 16:419-424 (1997).
Osmitrol (generic name Mannitol),Official FDA Information, side effects and uses, pp. 1-10 (2010) http://www.drugs.com/pro/osmitrol.html.
Park et al., "Biological Characterization of EDC-crosslinked Collagen-Hyaluronic Acid Matrix in Dermal Tissue Restoration", Biomaterials 24 (2003) 1631-1641.
Park et al., "Characterization of Porous Collagen/Hyaluronic Acid Scaffold Modified by 1-ethyl-3-(3-dimethylaminopropyl)carbodiimide cross-linking", Biomaterials 23 (2002): 1205-1212.
Powell; "Stability of Lidocaine in Aqueous Solution: Effect of Temperature, pH, Buffer, and Metal Ions on Amide Hydrolysis"; Pharmaceutical Research; vol. 4, No. 1, 1987.
Prestwich, Glenn D., "Evaluating drug efficacy and toxicology in three dimensions: using synthetic extracellular matrices in drug discovery," Accounts of Chemical Research 41 (1):139-148 (2008).
Rehakova, Milena, et al., "Properties of collagen and hyaluronic acid composite materials and their modifications by chemical crosslinking," Journal of Biomedical Research, vol. 30, 1996, pp. 36-372, XP002590342.
Remington's Pharmaceutical Science Mac Publishing Company, Easton, PA 16th Edition 1980.
Rosenblatt et al., "The Effect of Collagen Fiber Size Distribution on the Release Rate of Proteins from Collagen Matrices by Diffusion", J. Controlled Rel., 9, pp. 195-203 (1989).
Rosenblatt et al., "Chain Rigidity and Diffusional Release in Biopolymer Gels", Proceed. Inter. Symp. Control. Rel. Bioact. Mater., 20, pp. 264-265 (1993) Controlled Release Society, Inc.
Sannino et al., "Crosslinking of Cellulose Derivatives and Hyaluronic Acid with Water-Soluble Carbodiimide," Polymer 46 (2005)pp. 11206-11212.
Sculptra® Aesthetic (injectable poly-L-lactic acid) Directions for Use, Dermik Laboratories product insert (Jul. 2009), sanofi-aventis U.S. LLC.
Segura et al. "Crosslinked hyaluronic acid hydrogels: a strategy to functionalize and pattern." Biomaterials 26(4): 359-371 (2005).
Selvi et al, "Arthritis Induced by Corticosteroid Crystals", J. Rheumatology, 2004, 34:3.
Serban et al. "Modular Extracellular Matrices: Solutions for the Puzzle." Methods 45(1): 93-98 (2008).
Shu et al. "Synthesis and evaluation of injectable, in situ crosslinkable synthetic extracellular matrices for tissue engineering." J. Biomed. Mater. Res. A. 79(4): 902-912 (2006).
Silver et al., "Physical Properties of Hyaluronic Acid and Hydroxypropylmethylcellulose in Solution: Evaluation of Coating Ability," Journal of Applied Biomaterials, vol. 5, 89-98 (1994).
Skardal etal "Bioprinting Vessel-Like Constructs Using Hyaluronan Hydrogels Crosslinkedwith Tetrahedral Polyethylene Glyol Tetracrylates"; BioMaterials. Elsevier Science Publishers BV; vol. 31, No. 24; pp. 6173-6181; Aug. 1, 2010.

Smith, Kevin C., et al., "Five Percent Lidocaine Cream Applied Simultaneously to Skin and Mucosa of the Lips Creates Excellent Anesthesia for Filler Injections", Dermatol Surg 2005; 31:1635-1637.
Tezel et al. "The science of hyaluronic acid dermal fillers." J. Cosmet. Laser Ther. 10(1): 35-42 (2008).
TRB Chemedica Ophthalmic Line, VISIOL, product info., pp. 1-2. VISIOL, Viscoelstic gel for use in ocular surgery, (2010) p. 1, htt://www.trbchemedica.com/index.php/option=com_content&tas.
Waraszkiewicz, Sigmund M., et al., "Stability-Indicating High-Performance Liquid Chromatographic Analysis of Lidocaine Hydrochloride and Lidocaine Hydrochloride with Epinephrine Injectable Solutions", Journal of Pharmaceutical Sciences, vol. 70, No. 11, Nov. 1981, pp. 1215-1218.
Wahl, "European Evaluation of a New Hyaluronic Acid Filler Incorporating Lidocaine", Journal of Cosmetic Dermatology; vol. 7; pp. 298-303; 2008.
Weidmann; "New Hyaluronic Acid Filler for Subdermal and Long-Lasting Volume Restoration of the Face"; European Dermatology; pp. 65-68; 2009.
Xia, Yun et al., "Comparison of Effects of Lidocaine Hydrochloride, Buffered Lidocaine, Diphenhydramine, and Normal Saline After Intradermal Injection", Journal of Clinical Anesthesia 14:339-343, 2002.
Yeom et al. "Effect of Cross-Linking Reagents for Hyaluronic Acid Hydrogel Dermal Fillers on Tissue Augmentation and Regeneration." Bioconjugate Chem., 21(2): 240-247 (2010).
Yui, Nobuhiko, et al., "Inflammation responsive degradation of crosslinked hyaluronic acid gels," Journal of Controlled release, 22 (1992) pp. 105-116.
Yui, Nobuhiko, et al., "Photo-responsive degradation of heterogeneous hydrogels comprising crosslinked hyaluronic acid and lipid microspheres for temporal drug delivery," Journal of Controlled Release, 26 (1993) pp. 141-145.
Yun, YH et al. "Hyaluronan Microspheres for Sustained Gene Delivery and Site-Specific Targeting", Biomaterials, vol. 25, 2004, pp. 147-157.
Zheng et al. "In situ crosslinkable hyaluronan hydrogels for tissue engineering." Biomaterials 25(7-8): 1339-1348 (2004).
Zulian et al., Triamcinolone Acetonide and Hexacetonide Intra-Articular Treatment of Symmetrical Joints in Juvenile Idiopathic Arthritis: a Double-Blind Trial, Rheum 2004.
Boulle et al., "Lip Augmentation and Contour Correction With a Ribose Cross-linked Collagen Dermal Filler", Journals of Drugs in Dermatology, Mar. 2009, vol. 8, Issue 3, pp. 1-8.
Crosslinking Technical Handbook, Thermo Scientific, pp. 1-48, published Apr. 2009.
Park et al., "In vireio evaluation of conjugated Hyalruonic acid with Ascorbic Acid", Journal of Bone & Joint Surgery, British vol. 92-B, XP-002706399, 2010.
Aesthetic Buyers Guide, "Juvéderm Raises Standards" Jan./Feb. 2007 (5 pp.), www.miinews.com.
Adams, "An Analysis of Clinical Studies of the Uses of Crosslinked Hyaluronan, Hylan, in the Treatment of Osteoarthritis", J. Rheumatol Suppl., Aug. 1993; 39:16-8.
Albano, Emanuele, et al., "Hydroxyethyl Radicals in Ethanol Hepatotoxicity," Frontiers in Bioscience 4:533-540 (1999).
Allemann et al., "Hyaluronic acid gel (JUVEDERM) preparations in the treatment of facial wrinkles and folds", 2008, Clinical Interventions in Aging, vol. 3, No. 4, pp. 629-634.
Antunes, Alberto A., et al., "Efficacy of Intrarectal Lidocaine Hydrochloride Gel for Pain control in Patients Undergoing Transrectal Prostate Biopsy", International Braz J Urol, vol. 30(5): 380-383, Sep.-Oct. 2004.
Atanassoff, Peter G., et al., "The Effect of Intradermal Administration of Lidocaine and Morphine on the Response to Thermal Stimulation", Anesth Analg 1997; 84:1340-3.
Baumann et al. "JUVEDERM vs. ZYPLAST Nasolabial Fold Study Group, Comparison of smooth-gel hyaluronic acid dermal fillers with cross-linked bovine collagen: a multicenter, double-masked, randomized, within-subject study." Dermatol. Surg. 33(Suppl 2): S128-S135 (2007).

(56) References Cited

OTHER PUBLICATIONS

Beasley et al. :Hyaluronic acid fillers: a comprehensive review. Facial Plast. Surg. 25(2): 86-94 (2009).

Beer "Dermal fillers and combinations of fillers for facial rejuvenation." Dermatol. Clin. 27(4): 427-432 (2009).

Belda, Jose I., et al., "Hyaluronic acid combined with mannitol to improve protection against free-radical endothelial damage: Experimental Model," J.Cataract Refract Surg 2005; 31:1213-1218.

Bircher, Andreas J., et al., "Delayed-type hypersensitivity to subcutaneous lidocaine with tolerance to articaine: confirmation by in vivo and in vitro tests", Contact Dermatitis 1996, 34, 387-389.

Bluel et al., "Evaluation of Reconstituted Collagen Tape as a Model for Chemically Modified Soft Tissues", Biomat. Med. De. Art Org., 9(1):37-46 (1981).

Buck et al, "Injectable Fillers for our Facial Rejuvenation: a Review", Journal of Plastic, Reconstructive and Aesthetic Surgery, (2009), 62:11-18, XP002668828.

Capozzi et al., "Distant Migration of Silicone Gel From a Ruptured Breats Implant", Plastic and Reconstructive Surgery, 1978; 62:302-3.

Carlin, G., et al., "Effect of anti-inflammatory drugs on xanthine oxidase and xanthine oxidase induced depolymerization of hyaluronic acid," Agents and Actions. 16 (5):377-384 (1985).

Carruthers et al. "The science and art of dermal fillers for soft-tissue augmentation." J. Drugs Dermatol. 8(4): 335-350 (2009).

Champion, et al., "Role of Target Geometry in Phagocytosis", S. Proc. Nat. Acad. Sci., Mar. 2008, 2006, vol. 103, No. 13, pp. 4930-4934.

Chin, Thomas M., et al., "Allergic Hypersensitivity to Lidocaine Hydrochloride", International journal of Dermatology, vol. 19, Apr. 1980, pp. 147-148.

Chvapil, "Collagen Sponse: Theory and Practice of Medical Applications", J. Biomed Mater. Res., II, pp. 721-741 (1977).

Clark et al., "The Influence of Triamcinolone Acetonide on Joint Stiffness in the Rat", J Bone Joint Surg Am, 1971; 53:1409-1414.

Cohen et al., "Organization and Adhesive Properties of the Hyaluronan Pericellular Coat of Chondrocytes and Epithelial Cells", Biophys J., 2003; 85:1996-2005.

Cui et al; "The Comparison of Physicochemical Properties of Four Cross-Linked Sodium Hyaluronate Gels with Different Cross-Linking Agents"; Advanced Material Research; vols. 396-398; pp. 1506-1512; 2012.

Deland, "Intrathecal Toxicity Studies with Benzyl Alcohol", Toxicol Appl Pharmacol, 1973; 25(2):153.

Desai et al., J Pharm Sci Feb. 1995; 84 (2): 212-5.

Eyre et al., Top Curr. Chem., 2005, vol. 247, pp. 207-229.

Falcone et al. "Crosslinked hyaluronic acid dermal fillers: a comparison of rheological properties." J Biomed Mater Res A. 87(1): 264-271 (2008).

Falcone et al. "Temporary polysaccharide dermal fillers: a model for persistence based on physical properties." Dermatol Surg. 35(8): 1238-1243 (2009).

Farley, Jon S., et al., "Diluting Lidocaine and Mepivacaine in Balanced Salt Solution Reduces the Pain of Intradermal Injection", Regional Anesthesia 19(1):48-51, 1994.

Frati, Elena, et al., "Degradation of hyaluronic acid by photosensitized riboflavin in vitro. Modulation of the effect by transition metals, radical quenchers, and metal chelators," Free Radical Biology Medicine 22 (7):1139-1144 (1997).

Fujinaga, Masahiko, et al., "Reproductive and Teratogenic Effects of Lidocaine in Sprague-Dawley Rats", Anesthesiology 65:626-632, 1986.

Gammaitoni, Arnold R., et al., "Pharmacokinetics and safety of continuously applied lidocaine patches 5%", Am J Health Syst Pharm, vol. 59, Nov. 15, 2002, pp. 2215-2220.

GinShiCel MH Hydroxy Propyl methyl Cellulose, Web Page http://www.ginshicel.cn/MHPC.html, Nov. 12, 2008.

Gold MH, "Use of Hyaluronic acid fillers for the treatment of the aging face." Clin. Interventions Aging 2(3): 369-376 (2007).

Goldberg "Breakthroughs in US dermal fillers for facial soft-tissue augmentation." J Cosmet Laser Ther. 11(4): 240-247 (2009).

Graefe, Hendrik, et al., "Sensitive and specific photometric determination of mannitol in human serum," Clin Chem Lab Med. 41 (8):1049-1055 (2003).

Grecomoro et al., "Intra-Articular Treatment with Sodium Hyaluronate in Gonarthrosis" A Controlled Clinical Trial Versus Placebo, Pharmatherapeutica, 1987; 5(2):137-41.

Grillo et al., "Thermal Reconstitution of Collagen from Solution and the Response to Its Heterologous Implantation", JSR II, No. 1, pp. 69-82 (1962).

Hassan et al., Effects of Adjuvants to local anaesthetics on their duration. III. Experimental studies of hyaluronic acid. Abstract Pub Med [Acta Anesthesiol Scand. May 1985; 29(4):384-8].

Hayashibara, "AA2G"; Sep. 23, 2007, http://web.archive.org/web/20079230720l0/http://www.hayashibara-intl.com/cosmetics/aa2g.html.

Helary et al., "Concentrated collagen hydrogels as dermal substitutes", Biomaterials 31 (2010) 481-490.

Helliwell, "Use of an Objective Measure of Articular Stiffness to Record Changes in Finger Joints After Intra-Articular Injection of Corticosteroid", An Theum Dis, 1997; 56:7.

Hertzberger-Ten et al., "Intra-Articular Steroids in Pauciarticular Juvenile Chronic Arthritis", Type I, Eur J Ped 1991; 150:170-172.

Hetherington, "Potential for Patient Harm From Intrathecal Administration of Preserved Solutions", Med J Aust, 2000, 173(3):p. 141.

Hurst, "Adhesive Arachnoiditis and Vascular Blockage Caused by Detergents and Other Chemical Irritants: an Experimental Study", J Path Bact, 1955; 70:167.

Intramed Mannitol 20% m/v Infusion, package insert, pp. 1-2 (2010) http://home.intekom.com/pharm/intramed/manitl20.html.

Jones et al., "Intra-Articular Hyaluronic Acid Compared to Intra-Articular Triamcinolone Hexacetonide in Inflammatory Knee Osteoarthritis", Osteoarthritis Cartilage, 1995, 3:269-273.

Kablik et al. "Comparative physical properties of hyaluronic acid dermal fillers." Dermatol. Surg. Suppl. 35(Suppl. 1): 302-312 (2009).

Klein, "Skin Filling Collagen and Other Injectables of the Skin", Dermatologic Clinics, Jul. 2001, vol. 19, No. 3, pp. 491-588, ix, XP00919589.

Kopp et al., The Short-Term Effect of Intra-Articular Injections of Sodium Hyaluronate and Corticosteroid on Temporomandibular Joint Pain and Dysfunction, J. Oral Maxillofac.

Kulicke et al., "Visco-Elastic Properties of Sodium Hyaluronate Solutions," American Institue of Physics (2008).

* cited by examiner

AA2G, (L-ascorbic acid 2-glucoside)

Vitagen, (ascobyl 3-aminopropyl phosphate)

AA2P, sodium ascorbyl phosphate

BDDE, 1,4-butanediol diglycidal ether

Star-PEG epoxide, pentaerythritol glycidal ether

Star-PEG amine, pentaerythritol (3-aminopropyl) ether

| Sample ID | Crosslinker | Conjugation degree (HA-AA2G, mol%) | G' (Pa) |
|---|---|---|---|
| | BDDE | 12 | 69 |
| | | 9.78 | 291 |
| | | 10.47 | 377 |
| | | 12.44 | 1160 |
| | Star Arm PEG Epoxide | 32.26 | 132 |
| | | 31.25 | 263 |
| | | 20.48 | 421 |
| | | 31.87 | 1160 |

HA-AA2G/Epoxyl: Gel Synthesis Results

FIG. 7

| Conjugation Degree (HA-AA2G, mol%) | Gel Conc. (mg/ml) | G' (Pa) |
|---|---|---|
| 8.0 | 25 | 42 |
| 12.0 | 17 | 69 |
| 11.6 | 24 | 113 |
| 12.6 | 24 | 237 |
| 9.8 | 17 | 291 |
| 10.5 | 17 | 377 |
| 8.5 | 26 | 700 |
| 13.0 | 22 | 1010 |
| 11.9 | 23 | 1260 |

HA-AA2G (BDDE)

FIG. 8

| Cross linker | Conjugation degree (AsA mole / AA2G mole)% |
|---|---|
| BDDE | 9.78 |
| BDDE | 10.04 |
| BDDE | 10.49 |
| BDDE | 13.76 |
| Star-PEG | 19.30 |
| Star-PEG | 31.87 |

For the same formulation, the released amount increases with the increase of the enzyme concentration.

Images of gels from
(a) Example 19, (b) Example 21, (c) Juvederm Refine, and (d) Restylane Touch

DERMAL FILLER COMPOSITIONS FOR FINE LINE TREATMENT

RELATED APPLICATIONS

This application claims priority to and the benefit of U.S. Provisional Patent Application No. 61/534,780, filed on Sep. 14, 2011, and is a continuation in part of U.S. patent application Ser. No. 13/593,313, filed on Aug. 23, 2012, which is a continuation-in-part of U.S. patent application Ser. No. 13/486,754, filed on Jun. 1, 2012, which claims priority to and the benefit of U.S. Provisional Patent Application No. 61/493,309, filed on Jun. 3, 2011, the entire disclosure of each of these applications being incorporated herein in its entirety by this specific reference.

BACKGROUND

The present invention generally relates to dermal filler compositions, and more specifically relates to injectable dermal filler compositions that are effective for treatment of fine lines in skin.

Skin aging is a progressive phenomenon, occurs over time and can be affected by lifestyle factors, such as alcohol consumption, tobacco and sun exposure. Aging of the facial skin can be characterized by atrophy, slackening, and fattening. Atrophy corresponds to a massive reduction of the thickness of skin tissue. Slackening of the subcutaneous tissues leads to an excess of skin and ptosis and leads to the appearance of drooping cheeks and eye lids. Fattening refers to an increase in excess weight by swelling of the bottom of the face and neck. These changes are typically associated with dryness, loss of elasticity, and rough texture.

Hyaluronic acid (HA), also known as hyaluronan, is a non-sulfated glycosaminoglycan that is distributed widely throughout the human body in connective, epithelial, and neural tissues. Hyaluronic acid is abundant in the different layers of the skin, where it has multiple functions such as, e.g., to ensure good hydration, to assist in the organization of the extracellular matrix, to act as a filler material; and to participate in tissue repair mechanisms. However, with age, the quantity of hyaluronic acid, collagen, elastin, and other matrix polymers present in the skin decreases. For example, repeated exposed to ultra violet light, e.g., from the sun, causes dermal cells to both decrease their production of hyaluronan as well as increase the rate of its degradation. This loss of materials results in various skin conditions such as, e.g., wrinkling, hollowness, loss of moisture and other undesirable conditions that contribute to the appearance of aging.

Injectable dermal fillers have been successfully used in treating the aging skin. The fillers can replace lost endogenous matrix polymers, or enhance/facilitate the function of existing matrix polymers, in order to treat these skin conditions. Hyaluronic acid-based dermal fillers have become increasingly popular, as hyaluronic acid is a substance naturally found throughout the human body. These fillers are generally well tolerated, nonpermanent, and a fairly low risk treatment for a wide variety of skin conditions.

Tyndall effect is an adverse event occurring in some patients administered with hyaluronic acid (HA)-based dermal fillers. Tyndall effect is characterized by the appearance of a blue discoloration at the skin site where a dermal filler had been injected, which represents visible hyaluronic acid seen through the translucent epidermis. Clinical reports suggest that filler administration technique and skin properties can influence the manifestation of this adverse event. Fillers with high stiffness and elasticity are successfully used to correct areas on the face like nasolabial folds, cheeks, and chin without any fear of facial discoloration, as the materials are injected in the mid and deep dermis regions. However, when these filler materials are used to correct superficial, fine line wrinkles, for example, tear trough, glabellar lines periorbital lines, smile lines, or forehead, or mistakenly applied too superficially in the upper regions of the dermis, a bluish discoloration of the skin is often observed. This phenomenon, which is thought to be the result of Tyndall effect, leaves a semi-permanent discoloration of the application sites, and sometimes disappears only after the administration of hyaluronidase to degrade the filler material. Consequently, Tyndall effect is more common in patients treated for superficial fine line wrinkles. Prolonged manifestation of Tyndall effect, typically for several months as long as the gel lasts in the skin, is a cause of major concern among patients.

HA-based dermal filler gels have been specifically formulated to treat "fine line" wrinkles found around the tear trough, forehead, periobital, glabellar lines, etc. Commercially available HA "fine line" gels include Juvéderm Refine (G' ~67 Pa; G"/G' ~0.59, HA concentration 18 mg/ml), Belotero Soft (G' ~28 Pa; G"/G' ~1.1, HA concentration 20 mg/ml), Emervel Touch (G' ~56 Pa; G"/G' ~0.64, HA concentration 20 mg/ml), Stylage S (G' ~192 Pa; G"/G' ~0.20, HA concentration 16 mg/ml), Teosyal First Lines (G' 59 Pa; G"/G' ~0.53, HA concentration 20 mg/ml), Restylane Touch (G' ~489 Pa; G"/G' ~0.24, HA concentration 18 mg/ml). Though these gels are formulated to have low elastic moduli, for example, by lightly crosslinking the linear HA chains with a small amount of crosslinker and/or by reducing the final HA concentration of these gels, most of the commercially available "fine line" gels still show Tyndall effect in some patients, especially when injected superficially, for example, at a depth of less than about one mm.

Collagen-based gels can be employed in the treatment of superficial wrinkles and does not appear to cause Tyndall effect. Collagen based gels are not highly favored as they have relatively poor duration in the skin and require pre-testing in individuals. Radiesse® (calcium hydroxylapatite) is a subdermal, injectable implant, whose principal component is synthetic calcium hydroxylapatite, not hyaluronic acid. Unlike hyaluronic acid-based dermal fillers, calcium hydroxylapatite is not transparent, and thus avoids the complication of the Tyndall effect. However, if placed too superficially, this filler can be seen as a white substance immediately beneath the skin. Furthermore, compared to hyaluronic acid based fillers, Radiesse® requires a larger needle for injection and is not typically recommended for use in the eye area.

It would be desirable to provide an injectable hyaluronic acid-based dermal filler that does not exhibit the bluish discoloration attributed to Tyndall effect, even when injected superficially.

SUMMARY

The present invention describes compositions and formulation methods for preparing HA-based dermal fillers that can be administered in the upper dermis without producing any bluish discoloration of the skin, or at least no significant or noticeable bluish discoloration. Further, many of the presently described filler gels of the invention have been found to last significantly longer in vivo than current commercially available gels. In some aspects of the invention, optically transparent dermal fillers useful for enhancing the appearance of the skin are provided which add volume and fullness, and reduce the appearance of even fine line wrinkles without "tyndalling". The present compositions can be introduced into fine lines in the skin, even in regions of thin skin and rather superficially, without causing the negative blue discoloration associated with many conventional optically transparent dermal fillers.

More specifically, in one aspect of the present invention, long lasting, therapeutic dermal filler compositions are provided which generally comprise a biocompatible polymer, for example, crosslinked hyaluronic acid component and an additive combined with the hyaluronic acid component.

In one embodiment, the polymer is a polysaccharide, for example, hyaluronic acid. The hyaluronic acid includes a crosslinked component and may further include a non-crosslinked component. The additive may comprise a vitamin, for example, vitamin C, for example, a stabilized form of vitamin C, or a vitamin C derivative, for example, L-ascorbic acid 2-glucoside (AA2G), ascobyl 3-aminopropyl phosphate (Vitagen) or sodium ascorbyl phosphate (AA2P).

In one aspect of the invention, the additive is a vitamin derivative which is covalently conjugated to the polymer by a suitable reaction process, for example, etherification, amidization or estherification.

In a broad aspect of the invention, a dermal filler composition is provided, the composition comprising a hyaluronic acid component crosslinked with a crosslinking component, and an additive other than the crosslinking component. The hyaluronic acid component may be chemically conjugated to the additive. Further, the composition exhibits reduced Tyndall effect when administered into a dermal region of a patient, relative to composition that is substantially identical except without the additive. The composition may further comprise other additives, for example, an anesthetic agent, such as lidocaine. In one embodiment, the additive is a vitamin C derivative, for example, AA2G. In another embodiment, the additive is Vitagen.

In one embodiment, the hyaluronic acid component is chemically conjugated to the additive with degree of conjugation being between about 3 mol % and about 40 mol, for example, between about 3 mol % and about 10 mol %.

The composition may be substantially optically transparent. The compositions generally have a G' value of between about 40 Pa and about 100 Pa, for example, no greater than about 100 Pa and, for example, no less than about 40 Pa.

In another aspect of the invention, methods of treating fine lines in the skin of a patient are provided. In one embodiment, the method comprises the steps of introducing, into skin of a patient, a composition comprising a mixture of a hyaluronic acid component, a crosslinking component crosslinking the hyaluronic acid, and an additive other than the crosslinking component, the composition being substantially optically transparent, and wherein the composition exhibits reduced Tyndall effect relative to composition that is substantially identical except without the additive.

In another aspect of the invention, methods of improving aesthetic appearance of a face are provided, the methods generally comprising the steps of administering, to a dermal region of a patient, a substantially optically transparent dermal filler composition that exhibits no or insignificant Tyndall effect. The composition may be made by the steps of providing hyaluronic acid, reacting a crosslinking agent with a vitamin C derivative, adding the reacted crosslinking agent and vitamin C derivative to the hyaluronic acid to form a crosslinked hyaluronic acid composition including covalently conjugated vitamin C; and homogenizing and neutralizing the crosslinked hyaluronic acid composition to obtain an injectable dermal filler composition. In some embodiments, the vitamin C derivative is AA2G. In other embodiments, the vitamin C derivative is Vitagen.

In yet another aspect of the invention, methods of reducing appearance of fine lines in thin skin regions of a patient are provided, wherein the method generally comprises administering to the patient a dermal filler composition, at a depth of no greater than about 1 mm, a substantially optically transparent hyaluronic acid based dermal filler composition including a vitamin C or a vitamin C derivative. In some embodiments, the composition is injected at a depth of a depth of no greater than about 0.8 mm, no greater than about 0.6 mm, or no greater than about 0.4 mm.

In yet another aspect of the invention, a dermal filler composition is provided which is substantially optically transparent, and generally comprises a hyaluronic acid component crosslinked with a crosslinking component, and a vitamin C derivative covalently conjugated to the hyaluronic acid component. In an exemplary embodiment, the composition and having a G' value between about 40 Pa and about 100 Pa. Further, the composition may have a hyaluronic acid concentration of between about 18 mg/g and about 30 mg/g. These compositions may be especially useful and effective in treating fine lines or superficial creases in the skin, for example, even in very thin skin, for example, skin having a thickness of no greater than about 1 mm. In some embodiments, the compositions of the invention last at least 3 months, at least 6 months or up to a year after being introduced into the skin.

These and other aspects and advantages of the present invention may be more readily understood and appreciated with referenced to the following drawings and detailed description.

BRIEF DESCRIPTION OF DRAWINGS

FIG. 7 is a Table showing conjugation degrees and G' values for various dermal filler compositions in accordance with the invention.

FIG. 8 is a Table showing conjugation degrees, HA concentration and G' values for HA-AA2G(BDDE) dermal filler compositions in accordance with the invention.

DETAILED DESCRIPTION

Figure 1:
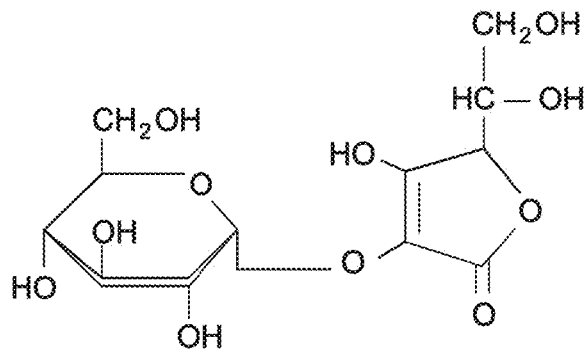
FIG. 1 is a representation of the structure of L-ascorbic acid 2-glucoside (AA2G)
Figure 2:
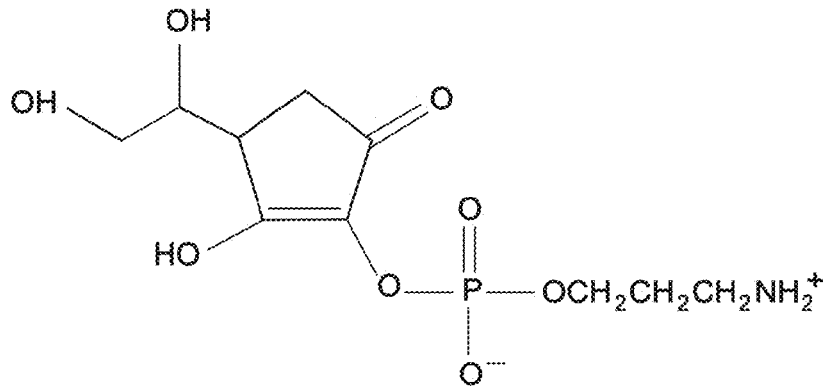
FIG. 2 is a representation of the structure of ascobyl 3-aminopropyl phosphate (Vitagen).
Figure 3:
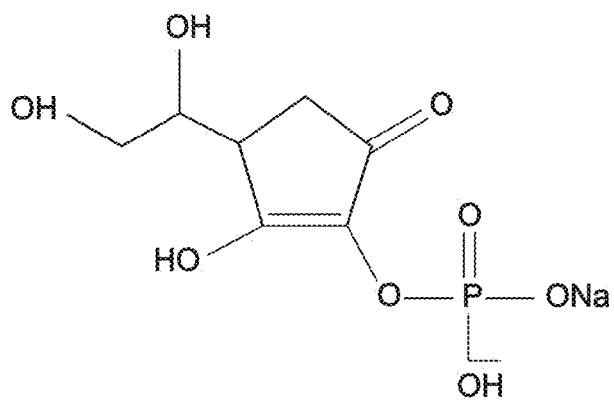
FIG. 3 is a representation of the structure of sodium ascorbyl phosphate (AA2P).
Figure 4:
FIG. 4 is a representation of the structure of 1,4-butanediol diglycidyl ether (BDDE).
Figure 5:
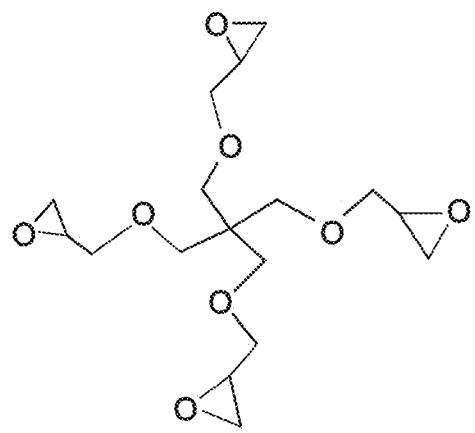
FIG. 5 is a representation of the structure of pentaerythritol glycidal ether (Star-PEG epoxide).
Figure 6:
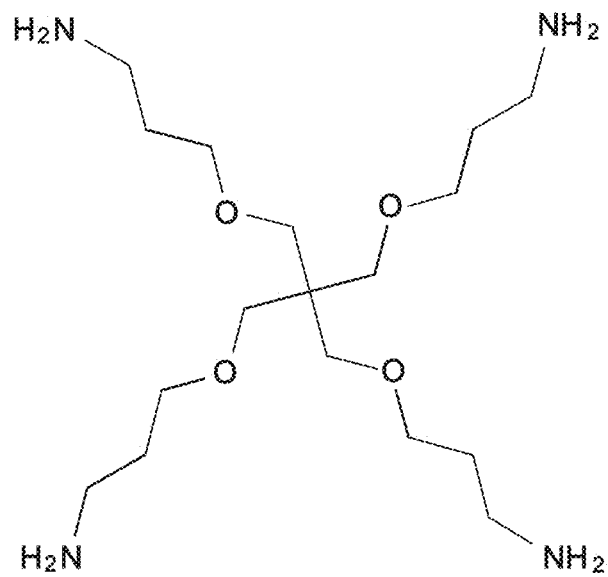
FIG. 6 is a representation of the structure of pentaerythritol (3-aminopropyl) ether (Star-PEG amine).

In one aspect of the invention, dermal filler compositions are provided, the compositions generally comprising a biocompatible polymer, for example, a polysaccharide such as a crosslinked hyaluronic acid, and a vitamin C derivative covalently conjugated to the polymer. The composition is provides sustained release of the vitamin C for skin neocollagenesis as well as other therapeutic or cosmetic benefits. When introduced into the skin, for example intradermally, the composition reacts with endogeneous enzymes in the body, and over time, bioactive vitamin C is generated in vivo, via enzymatic cleavages. As vitamin C is released from the composition over a period of weeks or months, its attendant benefits are made available to the body.

The polymer may be selected from the group of polymers consisting of proteins, peptides and polypeptides, polylysine, collagens, pro-collagens, elastins, and laminins.

The polymer may be selected from the group of polymers consisting of synthetic polymers with hydroxyl, amine, and carboxyl functional groups: poly(vinyl alcohol), polyethylene glycol, polyvinlyl amine, polyallylamine, deacetylated polyacrylamide, polyacrylic acid, and polymethacrylic acid. The polymer may be selected from the group of polymers consisting of dentric or branched polymers, including dentric polyols and dentric polyamines. The polymer may be selected from the group of polymers consisting of solid surface with hydroxyl, amine, and carboxyl functional groups.

The polymer may be a polysaccharide, for example, selected from the group of polysaccharides including starch and its derivatives; dextran and its derivatives, cellulose and its derivatives; chitin and chitosan and alginate and its derivatives.

In an exemplary embodiment of the invention, the polymer is glycosaminoglycan. The hydrogel composition disclosed herein can further comprise two or more different glycosaminoglycan polymers. As used herein, the term "glycosaminoglycan" is synonymous with "GAG" and "mucopolysaccharide" and refers to long unbranched polysaccharides consisting of a repeating disaccharide units. The repeating unit consists of a hexose (six-carbon sugar) or a hexuronic acid, linked to a hexosamine (six-carbon sugar containing nitrogen) and pharmaceutically acceptable salts thereof. Members of the GAG family vary in the type of hexosamine, hexose or hexuronic acid unit they contain, such as, e.g., glucuronic acid, iduronic acid, galactose, galactosamine, glucosamine) and may also vary in the geometry of the glycosidic linkage. Any glycosaminoglycan polymer is useful in the hydrogel compositions disclosed herein with the proviso that the glycosaminoglycan polymer improves a condition of the skin. Non-limiting examples of glycosaminoglycans include chondroitin sulfate, dermatan sulfate, keratan sulfate, hyaluronan. Non-limiting examples of an acceptable salt of a glycosaminoglycans includes sodium salts, potassium salts, magnesium salts, calcium salts, and combinations thereof. Glycosaminoglycan and their resulting polymers useful in the hydrogel compositions and methods disclosed herein are described in, e.g., Piron and Tholin, Polysaccharide Crosslinking, Hydrogel Preparation, Resulting Polysaccharides(s) and Hydrogel(s), uses Thereof, U.S. Patent Publication 2003/0148995; Lebreton, Cross-Linking of Low and High Molecular Weight Polysaccharides Preparation of Injectable Monophase Hydrogels; Lebreton, Viscoelastic Solutions Containing Sodium Hyaluronate and Hydroxypropyl Methyl Cellulose, Preparation and Uses, U.S. Patent Publication 2008/0089918; Lebreton, Hyaluronic Acid-Based Gels Including Lidocaine, U.S. Patent Publication 2010/0028438; and Polysaccharides and Hydrogels thus Obtained, U.S. Patent Publication 2006/0194758; and Di Napoli, Composition and Method for Intradermal Soft Tissue Augmentation, International Patent Publication WO 2004/073759, each of which is hereby incorporated by reference in its entirety. GAGs useful in the hydrogel compositions and methods disclosed herein are commercially available, such as, e.g., hyaluronan-based dermal fillers JUVEDERM®, JUVEDERM® 30, JUVEDERM® Ultra, JUVEDERM® Ultra Plus, JUVEDERM® Ultra XC, and JUVEDERM® Ultra Plus XC (Allergan Inc, Irvine, Calif.). Table 1 lists representative GAGs.

TABLE 1

Examples of GAGs

| Name | Hexuronic acid/Hexose | Hexosamine | Glycosidic linkage geometry | Unique features |
| --- | --- | --- | --- | --- |
| Chondroitin sulfate | GlcUA or GlcUA(2S) | GalNAc or GalNAc(4S) or GalNAc(6S) or GalNAc(4S,6S) | -4GlcUAβ1- 3GalNAcβ1- | Most prevalent GAG |
| Dermatan sulfate | GlcUA or IdoUA or IdoUA(2S) | GalNAc or GalNAc(4S) or GalNAc(6S) or GalNAc(4S,6S) | -4IdoUAβ1- 3GalNAcβ1- | Distinguished from chondroitin sulfate by the presence of iduronic acid, although some hexuronic acid monosaccharides may be glucuronic acid. |
| Keratan sulfate | Gal or Gal(6S) | GlcNAc or GlcNAc(6S) | -3Gal(6S)β1- 4GlcNAc(6S)β1- | Keratan sulfate type II may be fucosylated. |
| Heparin | GlcUA or IdoUA(2S) | GlcNAc or GlcNS or | -4IdoUA(2S)α1- 4GlcNS(6S)α1- | Highest negative charge density of any known |

TABLE 1-continued

Examples of GAGs

| Name | Hexuronic acid/Hexose | Hexosamine | Glycosidic linkage geometry | Unique features |
|---|---|---|---|---|
| | | GlcNAc(6S) or GlcNS(6S) | | biological molecule |
| Heparan sulfate | GlcUA or IdoUA or IdoUA(2S) | GlcNAc or GlcNS or GlcNAc(6S) or GlcNS(6S) | -4GlcUAβ1-4GlcNAcα1- | Highly similar in structure to heparin, however heparan sulfates disaccharide units are organized into distinct sulfated and non-sulfated domains. |
| Hyaluronan | GlcUA | GlcNAc | -4GlcUAβ1-3GlcNAcβ1- | The only GAG that is exclusively non-sulfated |

GlcUA = β-D-glucuronic acid
GlcUA(2S) = 2-O-sulfo-β-D-glucuronic acid
IdoUA = α-L-iduronic acid
IdoUA(2S) = 2-O-sulfo-α-L-iduronic acid
Gal = β-D-galactose
Gal(6S) = 6-O-sulfo-β-D-galactose
GalNAc = β-D-N-acetylgalactosamine
GalNAc(4S) = β-D-N-acetylgalactosamine-4-O-sulfate
GalNAc(6S) = β-D-N-acetylgalactosamine-6-O-sulfate
GalNAc(4S,6S) = β-D-N-acetylgalactosamine-4-O, 6-O-sulfate
GlcNAc = α-D-N-acetylglucosamine
GlcNS = α-D-N-sulfoglucosamine
GlcNS(6S) = α-D-N-sulfoglucosamine-6-O-sulfate Aspects of the present invention provide, in part, a hydrogel composition comprising a chondroitin sulfate polymer. As used herein, the term "chondroitin sulfate polymer" refers to an unbranched, sulfated polymer of variable length comprising disaccharides of two alternating monosaccharides of D-glucuronic acid (GlcA) and N-acetyl-D-galactosamine (GalNAc) and pharmaceutically acceptable salts thereof. A chondroitin sulfate polymer may also include D-glucuronic acid residues that are epimerized into L-iduronic acid (IdoA), in which case the resulting disaccharide is referred to as dermatan sulfate. A chondroitin sulfate polymer can have a chain of over 100 individual sugars, each of which can be sulfated in variable positions and quantities. Chondroitin sulfate polymers are an important structural component of cartilage and provide much of its resistance to compression. Any chondroitin sulfate polymer is useful in the compositions disclosed herein with the proviso that the chondroitin sulfate polymer improves a condition of the skin. Non-limiting examples of pharmaceutically acceptable salts of chondroitin sulfate include sodium chondroitin sulfate, potassium chondroitin sulfate, magnesium chondroitin sulfate, calcium chondroitin sulfate, and combinations thereof.

Aspects of the present specification provide, in part, a hydrogel composition comprising a keratan sulfate polymer. As used herein, the term "keratan sulfate polymer" refers to a polymer of variable length comprising disaccharide units, which themselves include β-D-galactose and N-acetyl-D-galactosamine (GalNAc) and pharmaceutically acceptable salts thereof. Disaccharides within the repeating region of keratan sulfate may be fucosylated and N-Acetylneuraminic acid caps the end of the chains. Any keratan sulfate polymer is useful in the compositions disclosed herein with the proviso that the keratan sulfate polymer improves a condition of the skin. Non-limiting examples of pharmaceutically acceptable salts of keratan sulfate include sodium keratan sulfate, potassium keratan sulfate, magnesium keratan sulfate, calcium keratan sulfate, and combinations thereof.

Aspects of the present specification provide, in part, a hydrogel composition comprising a hyaluronan polymer. As used herein, the term "hyaluronic acid polymer" is synonymous with "HA polymer", "hyaluronic acid polymer", and "hyaluronate polymer" refers to an anionic, non-sulfated glycosaminoglycan polymer comprising disaccharide units, which themselves include D-glucuronic acid and D-N-acetylglucosamine monomers, linked together via alternating β-1,4 and β-1,3 glycosidic bonds and pharmaceutically acceptable salts thereof. Hyaluronan polymers can be purified from animal and non-animal sources. Polymers of hyaluronan can range in size from about 5,000 Da to about 20,000,000 Da. Any hyaluronan polymer is useful in the compositions disclosed herein with the proviso that the hyaluronan improves a condition of the skin. Non-limiting examples of pharmaceutically acceptable salts of hyaluronan include sodium hyaluronan, potassium hyaluronan, magnesium hyaluronan, calcium hyaluronan, and combinations thereof.

Aspects of the present specification provide, in part, a hydrogel composition comprising a crosslinked glycosaminoglycan polymer. As used herein, the term "crosslinked" refers to the intermolecular bonds joining the individual polymer molecules, or monomer chains, into a more stable structure like a gel. As such, a crosslinked glycosaminoglycan polymer has at least one intermolecular bond joining at least one individual polymer molecule to another one. The crosslinking of glycosaminoglycan polymers typically result in the formation of a hydrogel. Such hydrogels have high viscosity and require considerable force to extrude through a fine needle. Glycosaminoglycan polymers disclosed herein may be crosslinked using dialdehydes and disulfides crosslinking agents including, without limitation, multifunctional PEG-based crosslinking agents, divinyl sulfones, diglycidyl ethers, and bis-epoxides, biscarbodiimide. Non-limiting examples of hyaluronan crosslinking agents include multifunctional PEG-based crosslinking agents like pentaerythritol tetraglycidyl ether (PETGE), divinyl sulfone (DVS), 1,4-butanediol diglycidyl ether (BDDE), 1,2-bis(2,3- epoxypropoxy)ethylene (EGDGE), 1,2,7,8-diepoxyoctane (DEO), (phenylenebis-(ethyl)-carbodiimide and 1,6 hexamethylenebis(ethylcarbodiimide), adipic dihydrazide (ADH), bis(sulfosuccinimidyl)suberate (BS), hexamethylenediamine (NMDA), 1-(2,3-epoxypropyl)-2,3-epoxycyclohexane, lysine, lysine methylester, or combinations thereof. Other useful cross-linking agents are disclosed in Stroumpoulis and Tezel, Tunably Crosslinked Polysaccharide Compositions, U.S. patent application Ser. No. 12/910,466, filed Oct. 22, 2010, which is incorporated by reference in its entirety. Non-limiting examples of methods of crosslinking glycosaminoglycan polymers are described in, e.g., Glycosaminoglycan polymers useful in the compositions and methods disclosed herein are described in, e.g., Piron and Tholin, Polysaccharide Crosslinking, Hydrogel Preparation, Resulting Polysaccharides(s) and Hydrogel(s), uses Thereof, U.S. Patent Publication 2003/0148995; Lebreton, Cross-Linking of Low and High Molecular Weight Polysaccharides Preparation of Injectable Monophase Hydrogels; Lebreton, Viscoelastic Solutions Containing Sodium Hyaluronate and Hydroxypropyl Methyl Cellulose, Preparation and Uses, U.S. Patent Publication 2008/0089918; Lebreton, Hyaluronic Acid-Based Gels Including Lidocaine, U.S. Patent Publication 2010/0028438; and Polysaccharides and Hydrogels thus Obtained, U.S. Patent Publication 2006/0194758; and Di Napoli, Composition and Method for Intradermal Soft Tissue Augmentation, International Patent Publication WO 2004/073759, each of which is hereby incorporated by reference in its entirety.

Aspects of the present specification provide, in part, a hydrogel composition comprising a crosslinked glycosaminoglycan polymer having a degree of crosslinking. As used herein, the term "degree of crosslinking" refers to the percentage of glycosaminoglycan polymer monomeric units, such as, e.g., the disaccharide monomer units of hyaluronan that are bound to a cross-linking agent. The degree of crosslinking is expressed as the percent weight ratio of the crosslinking agent to glycosaminoglycan. The degree of crosslinking in certain advantageous embodiment of the invention is between about 3% and about 12%, for example, between about 5% and about 10%.

In an embodiment, a hydrogel composition comprises a crosslinked glycosaminoglycan polymer, for example, crosslinked hyaluronic acid, wherein the crosslinked glycosaminoglycan polymer is present in the composition at a concentration of, for example, between about 18 mg/g and about 30 mg/g. In some embodiments, the compositions have a total hyaluronic acid concentration of about 24 mg/g or about 25 mg/g.

Aspects of the present specification provide, in part, a hydrogel composition comprising hyaluronan polymers of low molecular weight, hyaluronan polymers of high molecular weight, or hyaluronan polymers of both low and high molecular weight. As used herein, the term "high molecular weight" when referring to "hyaluronan" refers to hyaluronan polymers having a mean molecular weight of 1,000,000 Da or greater. Non-limiting examples of a high molecular weight hyaluronan polymers include hyaluronan polymers about 1,500,000 Da, about 2,000,000 Da, about 2,500,000 Da, about 3,000,000 Da, about 3,500,000 Da, about 4,000,000 Da, about 4,500,000 Da, and about 5,000,000 Da. As used herein, the term "low molecular weight" when referring to "hyaluronan" refers to hyaluronan polymers having a mean molecular weight of less than 1,000,000 Da. Non-limiting examples of a low molecular weight hyaluronan polymers include hyaluronan polymers of about 200,000 Da, about 300,000 Da, about 400,000 Da, about 500,000 Da, about 600,000 Da, about 700,000 Da, of about 800,000 Da, and about 900,000 Da.

In an embodiment, a composition comprises crosslinked hyaluronan polymers of low molecular weight. In aspects of this embodiment, a composition comprises crosslinked hyaluronan polymers having a mean molecular weight of, e.g., about 100,000 Da, about 200,000 Da, about 300,000 Da, about 400,000 Da, about 500,000 Da, about 600,000 Da, about 700,000 Da, about 800,000 Da, or about 900,000 Da. In yet other aspects of this embodiment, a composition comprises crosslinked hyaluronan polymers having a mean molecular weight of, e.g., at most 100,000 Da, at most 200,000 Da, at most 300,000 Da, at most 400,000 Da, at most 500,000 Da, at most 600,000 Da, at most 700,000 Da, at most 800,000 Da, at most 900,000 Da, or at most 950,000 Da. In still other aspects of this embodiment, a composition comprises crosslinked hyaluronan polymers having a mean molecular weight of, e.g., about 100,000 Da to about 500,000 Da, about 200,000 Da to about 500,000 Da, about 300,000 Da to about 500,000 Da, about 400,000 Da to about 500,000 Da, about 500,000 Da to about 950,000 Da, about 600,000 Da to about 950,000 Da, about 700,000 Da to about 950,000 Da, about 800,000 Da to about 950,000 Da, about 300,000 Da to about 600,000 Da, about 300,000 Da to about 700,000 Da, about 300,000 Da to about 800,000 Da, or about 400,000 Da to about 700,000 Da.

In another embodiment, a composition comprises crosslinked hyaluronan polymers of high molecular weight. In aspects of this embodiment, a composition comprises a crosslinked hyaluronan polymers having a mean molecular weight of, e.g., about 1,000,000 Da, about 1,500,000 Da, about 2,000,000 Da, about 2,500,000 Da, about 3,000,000 Da, about 3,500,000 Da, about 4,000,000 Da, about 4,500,000 Da, or about 5,000,000 Da. In yet other aspects of this embodiment, a composition comprises a crosslinked hyaluronan polymers having a mean molecular weight of, e.g., at least 1,000,000 Da, at least 1,500,000 Da, at least 2,000,000 Da, at least 2,500,000 Da, at least 3,000,000 Da, at least 3,500,000 Da, at least 4,000,000 Da, at least 4,500,000 Da, or at least 5,000,000 Da. In still other aspects of this embodiment, a composition comprises a crosslinked hyaluronan polymers having a mean molecular weight of, e.g., about 1,000,000 Da to about 5,000,000 Da, about 1,500,000 Da to about 5,000,000 Da, about 2,000,000 Da to about 5,000,000 Da, about 2,500,000 Da to about 5,000,000 Da, about 2,000,000 Da to about 3,000,000 Da, about 2,500,000 Da to about 3,000,000 Da.

In yet another embodiment, a composition comprises a crosslinked hyaluronan polymers where the crosslinked hyaluronan polymers comprise a combination of both high molecular weight hyaluronan polymers and low molecular weight hyaluronan polymers, in various ratios. In aspects of this embodiment, a composition comprises a crosslinked hyaluronan polymers where the crosslinked hyaluronan polymers comprises a combination of both high molecular weight hyaluronan polymers and low molecular weight hyaluronan polymers in a ratio of about 20:1, about 15:1, about 10:1, about 5:1, about 1:1, about 1:5 about 1:10, about 1:15, or about 1:20.

Aspects of the present specification provide, in part, a hydrogel composition comprising an uncrosslinked glycosaminoglycan polymer. As used herein, the term "uncrosslinked" refers to a lack of intermolecular bonds joining the individual glycosaminoglycan polymer molecules, or monomer chains. As such, an uncrosslinked glycosaminoglycan polymer is not linked to any other glycosaminoglycan polymer by an intermolecular bond. In aspects of this embodiment, a composition comprises an uncrosslinked chondroitin sulfate polymer, an uncrosslinked dermatan sulfate polymer, an uncrosslinked keratan sulfate polymer, an uncrosslinked heparan polymer, an uncrosslinked heparan sulfate polymer, or an uncrosslinked hyaluronan polymer. Uncrosslinked glycosaminoglycan polymers are water soluble and generally remain fluid in nature. As such, uncross-linked glycosaminoglycan polymers are often mixed with a glycosaminoglycan polymer-based hydrogel composition as a lubricant to facilitate the extrusion process of the composition through a fine needle.

In an embodiment, a composition comprises an uncrosslinked glycosaminoglycan polymer where the uncrosslinked glycosaminoglycan polymer is present at a concentration of, e.g., about 2 mg/g, about 3 mg/g, about 4 mg/g, about 5 mg/g, about 6 mg/g, about 7 mg/g, about 8 mg/g, about 9 mg/g, about 10 mg/g, about 11 mg/g, about 12 mg/g, about 13 mg/g, about 13.5 mg/g, about 14 mg/g, about 15 mg/g, about 16 mg/g, about 17 mg/g, about 18 mg/g, about 19 mg/g, about 20 mg/g, about 40 mg/g, or about 60 mg/g. In other aspects of this embodiment, a composition comprises an uncrosslinked glycosaminoglycan where the uncrosslinked glycosaminoglycan is present at a concentration of, e.g., at least 1 mg/g, at least 2 mg/g, at least 3 mg/g, at least 4 mg/g, at least 5 mg/g, at least 10 mg/g, at least 15 mg/g, at least 20 mg/g, at least 25 mg/g at least 35 mg/g, or at least 40 mg/g. In yet other aspects of this embodiment, a composition comprises an uncrosslinked glycosaminoglycan where the uncrosslinked glycosaminoglycan is present at a concentration of, e.g., at most 1 mg/g, at most 2 mg/g, at most 3 mg/g, at most 4 mg/g, at most 5 mg/g, at most 10 mg/g, at most 15 mg/g, at most 20 mg/g, or at most 25 mg/g. In still other aspects of this embodiment, a composition comprises an uncrosslinked glycosaminoglycan where the uncrosslinked glycosaminoglycan is present at a concentration of, e.g., about 1 mg/g to about 60 mg/g, about 10 mg/g to about 40 mg/g, about 7.5 mg/g to about 19.5 mg/g, about 8.5 mg/g to about 18.5 mg/g, about 9.5 mg/g to about 17.5 mg/g, about 10.5 mg/g to about 16.5 mg/g, about 11.5 mg/g to about 15.5 mg/g, or about 12.5 mg/g to about 14.5 mg/g.

Aspects of the present specification provide, in part, a hydrogel composition that is essentially free of a crosslinked glycosaminoglycan polymer. As used herein, the term "essentially free" (or "consisting essentially of") refers to a composition where only trace amounts of cross-linked matrix polymers can be detected. In an aspect of this embodiment, a composition comprises a chondroitin sulfate that is essentially free of a crosslinked chondroitin sulfate polymer, a dermatan sulfate essentially free of a crosslinked dermatan sulfate polymer, a keratan sulfate essentially free of a crosslinked keratan sulfate polymer, a heparan essentially free of a crosslinked heparan polymer, a heparan sulfate essentially free of a crosslinked heparan sulfate polymer, or a hyaluronan sulfate essentially free of a crosslinked hyaluronan polymer.

Aspects of the present specification provide, in part, a hydrogel composition that is entirely free of a crosslinked glycosaminoglycan polymer. As used herein, the term "entirely free" refers to a composition that within the detection range of the instrument or process being used, crosslinked glycosaminoglycan polymers cannot be detected or its presence cannot be confirmed. In an aspect of this embodiment, a composition comprises a chondroitin sulfate that is entirely free of a crosslinked chondroitin sulfate polymer, a dermatan sulfate entirely free of a crosslinked dermatan sulfate polymer, a keratan sulfate entirely free of a crosslinked keratan sulfate polymer, a heparan entirely free of a crosslinked heparan polymer, a heparan sulfate entirely free of a crosslinked heparan sulfate polymer, or a hyaluronan sulfate entirely free of a crosslinked hyaluronan polymer.

Aspects of the present specification provide, in part, a hydrogel composition comprising a ratio of crosslinked glycosaminoglycan polymer and uncrosslinked glycosaminoglycan polymer. This ratio of crosslinked and uncrosslinked glycosaminoglycan polymer is also known as the gel:fluid ratio. Any gel:fluid ratio is useful in making the compositions disclosed herein with the proviso that such ratio produces a composition disclosed herein that improves a skin condition as disclosed herein. Non-limiting examples of gel:fluid ratios in compositions of the present invention include 100:0, 98:2, 90:10, 75:25, 70:30, 60:40, 50:50, 40:60, 30:70, 25:75, 10:90; 2:98, and 0:100.

In aspects of this embodiment, a composition comprises a crosslinked glycosaminoglycan polymer and an uncrosslinked glycosaminoglycan polymer where the gel:fluid ratio is, e.g., about 0:100, about 1:99, about 2:98, about 3:97, about 4:96, about 5:95, about 6:94, about 7:93, about 8:92, about 9:91, or about 10:90. In other aspects of this embodiment, a composition comprises a crosslinked glycosaminoglycan polymer and an uncrosslinked glycosaminoglycan polymer where the gel:fluid ratio is, e.g., at most 1:99, at most 2:98, at most 3:97, at most 4:96, at most 5:95, at most 6:94, at most 7:93, at most 8:92, at most 9:91, or at most 10:90. In yet other aspects of this embodiment, a composition comprises a crosslinked glycosaminoglycan polymer and an uncrosslinked glycosaminoglycan polymer where the gel:fluid ratio is, e.g., about 0:100 to about 3:97, about 0:100 to about 5:95, or about 0:100 to about 10:90.

In other aspects of this embodiment, a composition comprises a crosslinked glycosaminoglycan polymer and an uncrosslinked glycosaminoglycan polymer where the gel:fluid ratio is, e.g., about 15:85, about 20:80, about 25:75, about 30:70, about 35:65, about 40:60, about 45:55, about 50:50, about 55:45, about 60:40, about 65:35, about 70:30, about 75:25, about 80:20, about 85:15, about 90:10, about 95:5, about 98:2, or about 100:0. In yet other aspects of this embodiment, a composition comprises a crosslinked glycosaminoglycan polymer and an uncrosslinked glycosaminoglycan polymer where the gel:fluid ratio is, e.g., at most 15:85, at most 20:80, at most 25:75, at most 30:70, at most 35:65, at most 40:60, at most 45:55, at most 50:50, at most 55:45, at most 60:40, at most 65:35, at most 70:30, at most 75:25, at most 80:20, at most 85:15, at most 90:10, at most 95:5, at most 98:2, or at most 100:0. In still other aspects of this embodiment, a composition comprises a crosslinked glycosaminoglycan polymer and an uncrosslinked glycosaminoglycan polymer where the gel:fluid ratio is, e.g., about 10:90 to about 70:30, about 15:85 to about 70:30, about 10:90 to about 55:45, about 80:20 to about 95:5, about 90:10 to about 100:0, about 75:25 to about 100:0, or about 60:40 to about 100:0.

A hydrogel composition disclosed herein may further comprise another agent or combination of agents that provide a beneficial effect when the composition is administered to an individual. Such beneficial agents include, without limitation, an antioxidant, an anti-itch agent, an anti-cellulite agent, an anti-scarring agent, an anti-inflammatory agent, an anesthetic agent, an anti-irritant agent, a vasoconstrictor, a vasodilator, an anti-hemorrhagic agent like a hemostatic agent or anti-fibrinolytic agent, a desquamating agent, a tensioning agent, an anti-acne agent, a pigmentation agent, an anti-pigmentation agent, or a moisturizing agent.

For purposes of the present specification, unless otherwise stated, "%" in a formulation is defined as weight by weight (i.e., w/w) percentage.

Aspects of the present specification provide, in part, a hydrogel composition disclosed herein that may optionally comprise an anesthetic agent. An anesthetic agent is preferably a local anesthetic agent, i.e., an anesthetic agent that causes a reversible local anesthesia and a loss of nociception, such as, e.g., aminoamide local anesthetics and aminoester local anesthetics. The amount of an anesthetic agent included in a composition disclosed herein is an amount effective to mitigate pain experienced by an individual upon administration of the composition. As such, the amount of an anesthetic agent included in a composition disclosed in the present specification is between about 0.1% to about 5% by weight of the total composition. Non-limiting examples of anesthetic agents include lidocaine, ambucaine, amolanone, amylocalne, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethysoquin, dimethocaine, diperodon, dycyclonine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, psuedococaine, pyrrocaine, ropivacaine, salicyl alcohol, tetracaine, tolycaine, trimecaine, zolamine, combinations thereof, and salts thereof. Non-limiting examples of aminoester local anesthetics include procaine, chloroprocaine, cocaine, cyclomethycaine, cimethocaine (larocaine), propoxycaine, procaine (novocaine), paraparacaine, tetracaine (amethocaine). Non-limiting examples of aminoamide local anesthetics include articaine, bupivacaine, cinchocaine (dibucaine), etidocaine, levobupivacaine, lidocaine (lignocaine), mepivacaine, piperocaine, prilocalne, ropivacaine, and trimecaine. A composition disclosed herein may comprise a single anesthetic agent or a plurality of anesthetic agents. A non-limiting example of a combination local anesthetic is lidocaine/prilocalne (EMLA).

Thus in an embodiment, a composition disclosed herein comprises an anesthetic agent and salts thereof. In aspects of this embodiment, a composition disclosed herein comprises an aminoamide local anesthetic and salts thereof or an aminoester local anesthetic and salts thereof. In other aspects of this embodiment, a composition disclosed herein comprises procaine, chloroprocaine, cocaine, cyclomethycaine, cimethocaine, propoxycaine, procaine, proparacaine, tetracaine, or salts thereof, or any combination thereof. In yet other aspects of this embodiment, a composition disclosed herein comprises articaine, bupivacaine, cinchocaine, etidocaine, levobupivacaine, lidocaine, mepivacaine, piperocaine, prilocalne, ropivacaine, trimecaine, or salts thereof, or any combination thereof. In still other aspects of this embodiment, a composition disclosed herein comprises a lidocaine/prilocalne combination.

In other aspects of this embodiment, a composition disclosed herein comprises an anesthetic agent in an amount of, e.g., about 0.1%, about 0.2%, about 0.3%, about 0.4%, about 0.5%, about 0.6%, about 0.7%, about 0.8% about 0.9%, about 1.0%, about 2.0%, about 3.0%, about 4.0%, about 5.0%, about 6.0%, about 7.0%, about 8.0%, about 9.0%, or about 10% by weight of the total composition. In yet other aspects, a composition disclosed herein comprises an anesthetic agent in an amount of, e.g., at least 0.1%, at least 0.2%, at least 0.3%, at least 0.4%, at least 0.5%, at least 0.6%, at least 0.7%, at least 0.8% at least 0.9%, at least 1.0%, at least 2.0%, at least 3.0%, at least 4.0%, at least 5.0%, at least 6.0%, at least 7.0%, at least 8.0%, at least 9.0%, or at least 10% by weight of the total composition. In still other aspects, a composition disclosed herein comprises an anesthetic agent in an amount of, e.g., at most 0.1%, at most 0.2%, at most 0.3%, at most 0.4%, at most 0.5%, at most 0.6%, at most 0.7%, at most 0.8% at most 0.9%, at most 1.0%, at most 2.0%, at most 3.0%, at most 4.0%, at most 5.0%, at most 6.0%, at most 7.0%, at most 8.0%, at most 9.0%, or at most 10% by weight of the total composition. In further aspects, a composition disclosed herein comprises an anesthetic agent in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.2% to about 0.9%, about 0.2% to about 1.0%, about 0.2% to about 2.0%, about 0.5% to about 1.0%, or about 0.5% to about 2.0% by weight of the total composition.

In another embodiment, a composition disclosed herein does not comprise an anesthetic agent.

In one aspect of the present invention, an injectable dermal filler is provided which comprises a polymer, for example, a glycosaminoglycan polymer, for example a hyaluronic acid polymer, for example, a hyaluronic acid at least a portion of which is crosslinked, and an additive or beneficial agent combined with the polymer.

The beneficial agent combined with the polymer may comprise a vitamin, for example, vitamin C. Non-limiting examples of suitable forms of vitamin C include ascorbic acid and sodium, potassium, and calcium salts of ascorbic acid, fat-soluble esters of ascorbic acid with long-chain fatty acids (ascorbyl palmitate or ascorbyl stearate), magnesium ascorbyl phosphate (MAP), sodium ascorbyl phosphate (SAP), and ascorbic acid 2-glucoside (AA2G™), sodium ascorbyl phosphate (AA2P), disodium ascorbyl sulfate, and ascobyl 3-aminopropyl phosphate (Vitagen).

In an especially advantageous embodiment, the beneficial agent is covalently conjugated to the polymer. For example, the beneficial agent may be a vitamin C, or a vitamin C derivative, which is covalently conjugated to the polymer and is present in the compositions in an amount between about 0.04% to about 5.0% by weight of the total composition, for example, between about 0.1% to about 4.0% by weight of the total composition, for example, between about 0.2% to about 2.0% by weight of the total composition. In one embodiment, the amount of vitamin C included in a composition disclosed herein is between about 0.3% to about 1.2% by weight of the total composition.

Preferably, the vitamin C covalently conjugated to the polymer, includes at least one of ascorbic acid, L-ascorbic acid, L-ascorbic acid 2-sulfate (AA-2S) and L-ascorbic acid 2-phosphate (AA-2P), ascorbic acid 2-O-glucoside (AA-2G), 6-O-acyl-2-O-alpha-D-glucopyranosyl-L-ascorbic acids (6-Acyl-AA-2G), (ascobyl 3-aminopropyl phosphate, Ascorbyl palmitate), derivatives and combinations thereof. A composition disclosed herein may comprise a single vitamin C agent or a plurality of vitamin C agents.

In another embodiment of the invention, a dermal filler is provided wherein the hyaluronic acid is crosslinked with BDDE. In this embodiment, the degree of conjugation may be between about 3 mol % and about 10 mol %, to about 15 mol % to about 40 mol %.

In some embodiments, the dermal fillers have a sustained bioavailability. For example, dermal fillers are provided which, when introduced into the skin of a human being, are effective to release ascorbic acid or other vitamin into the human being for at least about 1 months and up to about 20 months or more.

Aspects of the present specification provide, in part, a hydrogel composition disclosed herein that exhibits a complex modulus, an elastic modulus, a viscous modulus and/or a tan δ. The compositions as disclosed herein are viscoelastic in that the composition has an elastic component (solid-like such as, e.g., crosslinked glycosaminoglycan polymers) and a viscous component (liquid-like such as, e.g., uncrosslinked glycosaminoglycan polymers or a carrier phase) when a force is applied (stress, deformation). The rheological attribute that described this property is the complex modulus (G*), which defines a composition's total resistance to deformation. The complex modulus is a complex number with a real and imaginary part: $G^*=G'+iG''$. The absolute value of G* is $Abs(G^*)=Sqrt(G'^2+G''^2)$. The complex modulus can be defined as the sum of the elastic modulus (G') and the viscous modulus (G''). Falcone, et al., *Temporary Polysaccharide Dermal Fillers: A Model for Persistence Based on Physical Properties*, Dermatol Surg. 35(8): 1238-1243 (2009); Tezel, supra, 2008; Kablik, supra, 2009; Beasley, supra, 2009; each of which is hereby incorporated by reference in its entirety.

Elastic modulus, or modulus of elasticity, refers to the ability of a hydrogel material to resists deformation, or, conversely, an object's tendency to be non-permanently deformed when a force is applied to it. Elastic modulus characterizes the firmness of a composition and is also known as the storage modulus because it describes the storage of energy from the motion of the composition. The elastic modulus describes the interaction between elasticity and strength (G'=stress/strain) and, as such, provides a quantitative measurement of a composition's hardness or softness. The elastic modulus of an object is defined as the slope of its stress-strain curve in the elastic deformation region: λ=stress/strain, where λ is the elastic modulus in Pascal's; stress is the force causing the deformation divided by the area to which the force is applied; and strain is the ratio of the change caused by the stress to the original state of the object. Although depending on the speed at which the force is applied, a stiffer composition will have a higher elastic modulus and it will take a greater force to deform the material a given distance, such as, e.g., an injection. Specifying how stresses are to be measured, including directions, allows for many types of elastic moduli to be defined. The three primary elastic moduli are tensile modulus, shear modulus, and bulk modulus.

Viscous modulus is also known as the loss modulus because it describes the energy that is lost as viscous dissipation. Tan δ is the ratio of the viscous modulus and the elastic modulus, tan δ=G''/G'. Falcone, supra, 2009. For tan δ values disclosed in the present specification, a tan δ is obtained from the dynamic modulus at a frequency of 1 Hz. A lower tan δ corresponds to a stiffer, harder, or more elastic composition.

In another embodiment, a hydrogel composition disclosed herein exhibits an elastic modulus. In aspects of this embodiment, a hydrogel composition exhibits an elastic modulus of, e.g., about 25 Pa, about 50 Pa, about 75 Pa, about 100 Pa, about 125 Pa, about 150 Pa, about 175 Pa, about 200 Pa, about 250 Pa, about 300 Pa, about 350 Pa, about 400 Pa, about 450 Pa, about 500 Pa, about 550 Pa, about 600 Pa, about 650 Pa, about 700 Pa, about 750 Pa, about 800 Pa, about 850 Pa, about 900 Pa, about 950 Pa, about 1,000 Pa, about 1,200 Pa, about 1,300 Pa, about 1,400 Pa, about 1,500 Pa, about 1,600 Pa, about 1700 Pa, about 1800 Pa, about 1900 Pa, about 2,000 Pa, about 2,100 Pa, about 2,200 Pa, about 2,300 Pa, about 2,400 Pa, or about 2,500 Pa. In other aspects of this embodiment, a hydrogel composition exhibits an elastic modulus of, e.g., at least 25 Pa, at least 50 Pa, at least 75 Pa, at least 100 Pa, at least 125 Pa, at least 150 Pa, at least 175 Pa, at least 200 Pa, at least 250 Pa, at least 300 Pa, at least 350 Pa, at least 400 Pa, at least 450 Pa, at least 500 Pa, at least 550 Pa, at least 600 Pa, at least 650 Pa, at least 700 Pa, at least 750 Pa, at least 800 Pa, at least 850 Pa, at least 900 Pa, at least 950 Pa, at least 1,000 Pa, at least 1,200 Pa, at least 1,300 Pa, at least 1,400 Pa, at least 1,500 Pa, at least 1,600 Pa, at least 1700 Pa, at least 1800 Pa, at least 1900 Pa, at least 2,000 Pa, at least 2,100 Pa, at least 2,200 Pa, at least 2,300 Pa, at least 2,400 Pa, or at least 2,500 Pa. In yet other aspects of this embodiment, a hydrogel composition exhibits an elastic modulus of, e.g., at most 25 Pa, at most 50 Pa, at most 75 Pa, at most 100 Pa, at most 125 Pa, at most 150 Pa, at most 175 Pa, at most 200 Pa, at most 250 Pa, at most 300 Pa, at most 350 Pa, at most 400 Pa, at most 450 Pa, at most 500 Pa, at most 550 Pa, at most 600 Pa, at most 650 Pa, at most 700 Pa, at most 750 Pa, at most 800 Pa, at most 850 Pa, at most 900 Pa, at most 950 Pa, at most 1,000 Pa, at most 1,200 Pa, at most 1,300 Pa, at most 1,400 Pa, at most 1,500 Pa, or at most 1,600 Pa. In still other aspects of this embodiment, a hydrogel composition exhibits an elastic modulus of, e.g., about 25 Pa to about 150 Pa, about 25 Pa to about 300 Pa, about 25 Pa to about 500 Pa, about 25 Pa to about 800 Pa, about 125 Pa to about 300 Pa, about 125 Pa to about 500 Pa, about 125 Pa to about 800 Pa, about 500 Pa to about 1,600 Pa, about 600 Pa to about 1,600 Pa, about 700 Pa to about 1,600 Pa, about 800 Pa to about 1,600 Pa, about 900 Pa to about 1,600 Pa, about 1,000 Pa to about 1,600 Pa, about 1,100 Pa to about 1,600 Pa, about 1,200 Pa to about 1,600 Pa, about 500 Pa to about 2,500 Pa, about 1,000 Pa to about 2,500 Pa, about 1,500 Pa to about 2,500 Pa, about 2,000 Pa to about 2,500 Pa, about 1,300 Pa to about 1,600 Pa, about 1,400 Pa to about 1,700 Pa, about 1,500 Pa to about 1,800 Pa, about 1,600 Pa to about 1,900 Pa, about 1,700 Pa to about 2,000 Pa, about 1,800 Pa to about 2,100 Pa, about 1,900 Pa to about 2,200 Pa, about 2,000 Pa to about 2,300 Pa, about 2,100 Pa to about 2,400 Pa, or about 2,200 Pa to about 2,500 Pa.

In another embodiment, a hydrogel composition disclosed herein exhibits a viscous modulus. In aspects of this embodiment, a hydrogel composition exhibits a viscous modulus of, e.g., about 10 Pa, about 20 Pa, about 30 Pa, about 40 Pa, about 50 Pa, about 60 Pa, about 70 Pa, about 80 Pa, about 90 Pa, about 100 Pa, about 150 Pa, about 200 Pa, about 250 Pa, about 300 Pa, about 350 Pa, about 400 Pa, about 450 Pa, about 500 Pa, about 550 Pa, about 600 Pa, about 650 Pa, or about 700 Pa. In other aspects of this embodiment, a hydrogel composition exhibits a viscous modulus of, e.g., at most 10 Pa, at most 20 Pa, at most 30 Pa, at most 40 Pa, at most 50 Pa, at most 60 Pa, at most 70 Pa, at most 80 Pa, at most 90 Pa, at most 100 Pa, at most 150 Pa, at most 200 Pa, at most 250 Pa, at most 300 Pa, at most 350 Pa, at most 400 Pa, at most 450 Pa, at most 500 Pa, at most 550 Pa, at most 600 Pa, at most 650 Pa, or at most 700 Pa. In yet other aspects of this embodiment, a hydrogel composition exhibits a viscous modulus of, e.g., about 10 Pa to about 30 Pa, about 10 Pa to about 50 Pa, about 10 Pa to about 100 Pa, about 10 Pa to about 150 Pa, about 70 Pa to about 100 Pa, about 50 Pa to about 350 Pa, about 150 Pa to about 450 Pa, about 250 Pa to about 550 Pa, about 350 Pa to about 700 Pa, about 50 Pa to about 150 Pa, about 100 Pa to about 200 Pa, about 150 Pa to about 250 Pa, about 200 Pa to about 300 Pa, about 250 Pa to about 350 Pa, about 300 Pa to about 400 Pa, about 350 Pa to about 450 Pa, about 400 Pa to about 500 Pa, about 450 Pa to about 550 Pa, about 500 Pa to about 600 Pa, about 550 Pa to about 650 Pa, or about 600 Pa to about 700 Pa.

In another embodiment, a hydrogel composition disclosed herein exhibits a tan δ. In aspects of this embodiment, a hydrogel composition exhibits a tan δ of, e.g., about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, or about 2.5. In other aspects of this embodiment, a hydrogel composition exhibits a tan δ of, e.g., at most 0.1, at most 0.2, at most 0.3, at most 0.4, at most 0.5, at most 0.6, at most 0.7, at most 0.8, at most 0.9, at most 1.0, at most 1.1, at most 1.2, at most 1.3, at most 1.4, at most 1.5, at most 1.6, at most 1.7, at most 1.8, at most 1.9, at most 2.0, at most 2.1, at most 2.2, at most 2.3, at most 2.4, or at most 2.5. In yet other aspects of this embodiment, a hydrogel composition exhibits a tan δ of, e.g., about 0.1 to about 0.3, about 0.3 to about 0.5, about 0.5 to about 0.8, about 1.1 to about 1.4, about 1.4 to about 1.7, about 0.3 to about 0.6, about 0.1 to about 0.5, about 0.5 to about 0.9, about 0.1 to about 0.6, about 0.1 to about 1.0, about 0.5 to about 1.5, about 1.0 to about 2.0, or about 1.5 to about 2.5.

Aspects of the present specification provide, in part, a hydrogel composition disclosed herein having a transparency and/or translucency. Optical transparency is the physical property of allowing visible light to pass through a material, whereas translucency (also called translucence or translucidity) only allows light to pass through diffusely. The opposite property is opacity. Transparent materials are clear, while translucent ones cannot be seen through clearly. The hydrogels disclosed herein are preferably optically transparent or at least translucent.

In an embodiment, a hydrogel composition disclosed herein is optically translucent. In aspects of this embodiment, a hydrogel composition diffusely transmits, e.g., about 75% of the light, about 80% of the light, about 85% of the light, about 90% of the light, about 95% of the light, or about 100% of the light. In other aspects of this embodiment, a hydrogel composition diffusely transmits, e.g., at least 75% of the light, at least 80% of the light, at least 85% of the light, at least 90% of the light, or at least 95% of the light. In yet other aspects of this embodiment, a hydrogel composition diffusely transmits, e.g., about 75% to about 100% of the light, about 80% to about 100% of the light, about 85% to about 100% of the light, about 90% to about 100% of the light, or about 95% to about 100% of the light. In an embodiment, a hydrogel composition disclosed herein is optically transparent and transmits 100% of visible light.

A hydrogel composition disclosed herein may be further processed by pulverizing the hydrogel into particles and optionally mixed with a carrier phase such as, e.g., water or a saline solution to form an injectable or topical substance like a solution, oil, lotion, gel, ointment, cream, slurry, salve, or paste. As such, the disclosed hydrogel compositions may be monophasic or multiphasic compositions. A hydrogel may be milled to a particle size from about 10 μm to about 1000 μm in diameter, such as about 15 μm to about 30 μm, about 50 μm to about 75 μm, about 100 μm to about 150 μm, about 200 μm to about 300 μm, about 450 μm to about 550 μm, about 600 μm to about 700 μm, about 750 μm to about 850 μm, or about 900 μm to about 1,000 μm.

Aspects of the present specification provide, in part, a composition disclosed herein is injectable. As used herein, the term "injectable" refers to a material having the properties necessary to administer the composition into a skin region of an individual using an injection device with a fine needle. As used herein, the term "fine needle" refers to a needle that is 27 gauge or smaller. Injectability of a composition disclosed herein can be accomplished by sizing the hydrogel particles as discussed above.

In aspect of this embodiment, a hydrogel composition disclosed herein is injectable through a fine needle. In other aspects of this embodiment, a hydrogel composition disclosed herein is injectable through a needle of, e.g., about 27 gauge, about 30 gauge, or about 32 gauge. In yet other aspects of this embodiment, a hydrogel composition disclosed herein is injectable through a needle of, e.g., 22 gauge or smaller, 27 gauge or smaller, 30 gauge or smaller, or 32 gauge or smaller. In still other aspects of this embodiment, a hydrogel composition disclosed herein is injectable through a needle of, e.g., about 22 gauge to about 35 gauge, 22 gauge to about 34 gauge, 22 gauge to about 33 gauge, 22 gauge to about 32 gauge, about 22 gauge to about 27 gauge, or about 27 gauge to about 32 gauge.

In aspects of this embodiment, a hydrogel composition disclosed herein can be injected with an extrusion force of about 60 N, about 55 N, about 50 N, about 45 N, about 40 N, about 35 N, about 30 N, about 25 N, about 20 N, or about 15 N at speeds of 100 mm/min. In other aspects of this embodiment, a hydrogel composition disclosed herein can be injected through a 27 gauge needle with an extrusion force of about 60 N or less, about 55 N or less, about 50 N or less, about 45 N or less, about 40 N or less, about 35 N or less, about 30 N or less, about 25 N or less, about 20 N or less, about 15 N or less, about 10 N or less, or about 5 N or less. In yet other aspects of this embodiment, a hydrogel composition disclosed herein can be injected through a 30 gauge needle with an extrusion force of about 60 N or less, about 55 N or less, about 50 N or less, about 45 N or less, about 40 N or less, about 35 N or less, about 30 N or less, about 25 N or less, about 20 N or less, about 15 N or less, about 10 N or less, or about 5 N or less. In still other aspects of this embodiment, a hydrogel composition disclosed herein can be injected through a 32 gauge needle with an extrusion force of about 60 N or less, about 55 N or less, about 50 N or less, about 45 N or less, about 40 N or less, about 35 N or less, about 30 N or less, about 25 N or less, about 20 N or less, about 15 N or less, about 10 N or less, or about 5 N or less.

Aspects of the present specification provide, in part, a hydrogel composition disclosed herein that exhibits cohesivity. Cohesivity, also referred to as cohesion cohesive attraction, cohesive force, or compression force is a physical property of a material, caused by the intermolecular attraction between like-molecules within the material that acts to unite the molecules. Cohesivity is expressed in terms of grams-force (gmf). Cohesiveness is affected by, among other factors, the molecular weight ratio of the initial free glycosaminoglycan polymer, the degree of crosslinking of glycosaminoglycan polymers, the amount of residual free glycosaminoglycan polymers following crosslinking, and the pH of the hydrogel composition. A composition should be sufficiently cohesive as to remain localized to a site of administration. Additionally, in certain applications, a sufficient cohesiveness is important for a composition to retain its shape, and thus functionality, in the event of mechanical load cycling. As such, in one embodiment, a hydrogel composition disclosed herein exhibits cohesivity, on par with water. In yet another embodiment, a hydrogel composition disclosed herein exhibits sufficient cohesivity to remain localized to a site of administration. In still another embodiment, a hydrogel composition disclosed herein exhibits sufficient cohesivity to retain its shape. In a further embodiment, a hydrogel composition disclosed herein exhibits sufficient cohesivity to retain its shape and functionality.

Aspects of the present specification provide, in part, a hydrogel composition disclosed herein that exhibits a physiologically-acceptable osmolarity. As used herein, the term "osmolarity" refers to the concentration of osmotically active solutes in solution. As used herein, the term "a physiologically-acceptable osmolarity" refers to an osmolarity in accord with, or characteristic of, the normal functioning of a living organism. As such, administration of a hydrogel composition as disclosed herein exhibits an osmolarity that has substantially no long term or permanent detrimental effect when administered to a mammal. Osmolarity is expressed in terms of osmoles of osmotically active solute per liter of solvent (Osmol/L or Osm/L). Osmolarity is distinct from molarity because it measures moles of osmotically active solute particles rather than moles of solute. The distinction arises because some compounds can dissociate in solution, whereas others cannot. The osmolarity of a solution can be calculated from the following expression: $Osmol/L = \Sigma \phi_i \eta_i C_i$, where $\phi$ is the osmotic coefficient, which accounts for the degree of non-ideality of the solution; $\eta$ is the number of particles (e.g. ions) into which a molecule dissociates; and C is the molar concentration of the solute; and i is the index representing the identity of a particular solute. The osmolarity of a hydrogel composition disclosed herein can be measured using a conventional method that measures solutions.

In an embodiment, a hydrogel composition disclosed herein exhibits a physiologically-acceptable osmolarity. As used herein, the term "osmolality" refers to the concentration of osmotically active solutes per kilo of solvent in the body. As used herein, the term "a physiologically-acceptable osmolality" refers to an osmolality in accord with, or characteristic of, the normal functioning of a living organism. As such, administration of a hydrogel composition disclosed herein exhibits an osmolality that has substantially no long term or permanent detrimental effect when administered to a mammal. Osmolality is expressed in terms of osmoles of osmotically active solute per kilogram of solvent (osmol/kg or Osm/kg) and is equal to the sum of the molalities of all the solutes present in that solution. The osmolality of a solution can be measured using an osmometer. The most commonly used instrument in modern laboratories is a freezing point depression osmometer. This instruments measure the change in freezing point that occurs in a solution with increasing osmolality (freezing point depression osmometer) or the change in vapor pressure that occurs in a solution with increasing osmolality (vapor pressure depression osmometer).

In aspects of this embodiment, a hydrogel composition disclosed herein exhibits an osmolarity of, e.g., about 100 mOsm/L, about 150 mOsm/L, about 200 mOsm/L, about 250 mOsm/L, about 300 mOsm/L, about 350 mOsm/L, about 400 mOsm/L, about 450 mOsm/L, or about 500 mOsm/L. In other aspects of this embodiment, a hydrogel composition exhibits an osmolarity of, e.g., at least 100 mOsm/L, at least 150 mOsm/L, at least 200 mOsm/L, at least 250 mOsm/L, at least 300 mOsm/L, at least 350 mOsm/L, at least 400 mOsm/L, at least 450 mOsm/L, or at least 500 mOsm/L. In yet other aspects of this embodiment, a hydrogel composition exhibits an osmolarity of, e.g., at most 100 mOsm/L, at most 150 mOsm/L, at most 200 mOsm/L, at most 250 mOsm/L, at most 300 mOsm/L, at most 350 mOsm/L, at most 400 mOsm/L, at most 450 mOsm/L, or at most 500 mOsm/L. In still other aspects of this embodiment, a hydrogel composition exhibits an osmolarity of, e.g., about 100 mOsm/L to about 500 mOsm/L, about 200 mOsm/L to about 500 mOsm/L, about 200 mOsm/L to about 400 mOsm/L, about 300 mOsm/L to about 400 mOsm/L, about 270 mOsm/L to about 390 mOsm/L, about 225 mOsm/L to about 350 mOsm/L, about 250 mOsm/L to about 325 mOsm/L, about 275 mOsm/L to about 300 mOsm/L, or about 285 mOsm/L to about 290 mOsm/L.

Aspects of the present specification provide, in part, a hydrogel composition disclosed herein that exhibits substantial stability. As used herein, the term "stability" or "stable" when referring to a hydrogel composition disclosed herein refers to a composition that is not prone to degrading, decomposing, or breaking down to any substantial or significant degree while stored before administration to an individual. As used herein, the term "substantial heat stability", "substantially heat stable", "autoclave stable", or "steam sterilization stable" refers to a hydrogel composition disclosed herein that is substantially stable when subjected to a heat treatment as disclosed herein.

Stability of a hydrogel composition disclosed herein can be determined by subjecting a hydrogel composition to a heat treatment, such as, e.g., steam sterilization at normal pressure or under pressure (e.g., autoclaving). Preferably the heat treatment is carried out at a temperature of at least about 100° C. for between about one minute and about 10 minutes. Substantial stability of a hydrogel composition disclosed herein can be evaluated 1) by determining the change in the extrusion force (ΔF) of a hydrogel composition disclosed herein after sterilization, where the change in extrusion force less 2N is indicative of a substantially stable hydrogel composition as measured by (the extrusion force of a hydrogel composition with the specified additives) minus (the extrusion force of the a hydrogel composition without the added additives); and/or 2) by determining the change in rheological properties of a hydrogel composition disclosed herein after sterilization, where the change in tan δ 1 Hz of less than 0.1 is indicative of a substantially stable hydrogel composition as measured by (tan δ 1 Hz of gel formulation with additives) minus (tan δ 1 Hz of gel formulation without additives). As such, a substantially stable hydrogel composition disclosed herein retains one or more of the following characteristics after sterilization: homogeneousness, extrusion force, cohesiveness, hyaluronan concentration, agent(s) concentration, osmolarity, pH, or other rheological characteristics desired by the hydrogel before the heat treatment.

In an embodiment, a hydrogel composition comprising a glycosaminoglycan polymer and the at least one agent disclosed herein is processed using a heat treatment that maintains the desired hydrogel properties disclosed herein. In aspects of this embodiment, a hydrogel composition comprising a glycosaminoglycan polymer and the at least one agent disclosed herein is processed using a heat treatment of, e.g., about 100° C., about 105° C., about 110° C., about 115° C., about 120° C., about 125° C., or about 130° C. In other aspects of this embodiment, a hydrogel composition comprising a glycosaminoglycan polymer and the at least one agent disclosed herein is processed using a heat treatment of, e.g., at least 100° C., at least 105° C., at least 110° C., at least 115° C., at least 120° C., at least 125° C., or at least 130° C. In yet other aspects of this embodiment, a hydrogel composition comprising a glycosaminoglycan polymer and the at least one agent disclosed herein is processed using a heat treatment of, e.g., about 100° C. to about 120° C., about 100° C. to about 125° C., about 100° C. to about 130° C., about 100° C. to about 135° C., about 110° C. to about 120° C., about 110° C. to about 125° C., about 110° C. to about 130° C., about 110° C. to about 135° C., about 120° C. to about 125° C., about 120° C. to about 130° C., about 120° C. to about 135° C., about 125° C. to about 130° C., or about 125° C. to about 135° C.

Long term stability of a hydrogel composition disclosed herein can be determined by subjecting a hydrogel composition to a heat treatment, such as, e.g., storage in an about 45° C. environment for about 60 days. Long term stability of a hydrogel composition disclosed herein can be evaluated 1) by assessing the clarity and color of a hydrogel composition after the 45° C. heat treatment, with a clear and uncolored hydrogel composition being indicative of a substantially stable hydrogel composition; 2) by determining the change in the extrusion force (ΔF) of a hydrogel composition disclosed herein after the 45° C. heat treatment, where the change in extrusion force less 2N is indicative of a substantially stable hydrogel composition as measured by (the extrusion force of a hydrogel composition with the specified additives before the 45° C. heat treatment) minus (the extrusion force of the a hydrogel composition with the specified additives after the 45° C. heat treatment); and/or 3) by determining the change in rheological properties of a hydrogel composition disclosed herein after sterilization, where the change in tan δ 1 Hz of less than 0.1 is indicative of a substantially stable hydrogel composition as measured by (tan δ 1 Hz of gel formulation with the specified additives before the 45° C. heat treatment) minus (tan δ 1 Hz of gel formulation with the specified additives after the 45° C. heat treatment). As such, a long term stability of a hydrogel composition disclosed herein is evaluated by retention of one or more of the following characteristics after the 45° C. heat treatment: clarity (transparency and translucency), homogeneousness, and cohesiveness.

In aspects of this embodiment, a hydrogel composition is substantially stable at room temperature for, e.g., about 3 months, about 6 months, about 9 months, about 12 months, about 15 months, about 18 months, about 21 months, about 24 months, about 27 months, about 30 months, about 33 months, or about 36 months. In other aspects of this embodiment, a hydrogel composition is substantially stable at room temperature for, e.g., at least 3 months, at least 6 months, at least 9 months, at least 12 months, at least 15 months, at least 18 months, at least 21 months, at least 24 months, at least 27 months, at least 30 months, at least 33 months, or at least 36 months. In other aspects of this embodiment, a hydrogel composition is substantially stable at room temperature for, e.g., about 3 months to about 12 months, about 3 months to about 18 months, about 3 months to about 24 months, about 3 months to about 30 months, about 3 months to about 36 months, about 6 months to about 12 months, about 6 months to about 18 months, about 6 months to about 24 months, about 6 months to about 30 months, about 6 months to about 36 months, about 9 months to about 12 months, about 9 months to about 18 months, about 9 months to about 24 months, about 9 months to about 30 months, about 9 months to about 36 months, about 12 months to about 18 months, about 12 months to about 24 months, about 12 months to about 30 months, about 12 months to about 36 months, about 18 months to about 24 months, about 18 months to about 30 months, or about 18 months to about 36 months.

The present compositions may optionally include, without limitation, other pharmaceutically acceptable components, including, without limitation, buffers, preservatives, tonicity adjusters, salts, antioxidants, osmolality adjusting agents, emulsifying agents, wetting agents, and the like.

A pharmaceutically acceptable buffer is a buffer that can be used to prepare a hydrogel composition disclosed herein, provided that the resulting preparation is pharmaceutically acceptable. Non-limiting examples of pharmaceutically acceptable buffers include acetate buffers, borate buffers, citrate buffers, neutral buffered salines, phosphate buffers, and phosphate buffered salines. Any concentration of a pharmaceutically acceptable buffer can be useful in formulating a pharmaceutical composition disclosed herein, with the proviso that a therapeutically effective amount of the active ingredient is recovered using this effective concentration of buffer. Non-limiting examples of concentrations of physiologically-acceptable buffers occur within the range of about 0.1 mM to about 900 mM. The pH of pharmaceutically acceptable buffers may be adjusted, provided that the resulting preparation is pharmaceutically acceptable. It is understood that acids or bases can be used to adjust the pH of a pharmaceutical composition as needed. Any buffered pH level can be useful in formulating a pharmaceutical composition, with the proviso that a therapeutically effective amount of the matrix polymer active ingredient is recovered using this effective pH level. Non-limiting examples of physiologically-acceptable pH occur within the range of about pH 5.0 to about pH 8.5. For example, the pH of a hydrogel composition disclosed herein can be about 5.0 to about 8.0, or about 6.5 to about 7.5, about 7.0 to about 7.4, or about 7.1 to about 7.3.

Pharmaceutically acceptable preservatives include, without limitation, sodium metabisulfite, sodium thiosulfate, acetylcysteine, butylated hydroxyanisole and butylated hydroxytoluene. Pharmaceutically acceptable preservatives include, without limitation, benzalkonium chloride, chlorobutanol, thimerosal, phenylmercuric acetate, phenylmercuric nitrate, a stabilized oxy chloro composition, such as, e.g., PURITE® (Allergan, Inc. Irvine, Calif.) and chelants, such as, e.g., DTPA or DTPA-bisamide, calcium DTPA, and CaNaDTPA-bisamide.

Pharmaceutically acceptable tonicity adjustors useful in a hydrogel composition disclosed herein include, without limitation, salts such as, e.g., sodium chloride and potassium chloride; and glycerin. The composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition disclosed herein. Other non-limiting examples of pharmacologically acceptable components can be found in, e.g., Ansel, supra, (1999); Gennaro, supra, (2000); Hardman, supra, (2001); and Rowe, supra, (2003), each of which is hereby incorporated by reference in its entirety.

Aspects of the present specification provide, in part, a method of treating a soft tissue condition of an individual by administering a hydrogel composition disclosed herein. As used herein, the term "treating," refers to reducing or eliminating in an individual a cosmetic or clinical symptom of a soft tissue condition characterized by a soft tissue imperfection, defect, disease, and/or disorder; or delaying or preventing in an individual the onset of a cosmetic or clinical symptom of a condition characterized by a soft tissue imperfection, defect, disease, and/or disorder. For example, the term "treating" can mean reducing a symptom of a condition characterized by a soft tissue defect, disease, and/or disorder by, e.g., at least 20%, at least 30%, at least 40%, at least 50%, at least 60%, at least 70%, at least 80%, at least 90% or at least 100%. The effectiveness of a hydrogel composition disclosed herein in treating a condition characterized by a soft tissue defect, disease, and/or disorder can be determined by observing one or more cosmetic, clinical symptoms, and/or physiological indicators associated with the condition. An improvement in a soft tissue defect, disease, and/or disorder also can be indicated by a reduced need for a concurrent therapy. Those of skill in the art will know the appropriate symptoms or indicators associated with specific soft tissue defect, disease, and/or disorder and will know how to determine if an individual is a candidate for treatment with a compound or composition disclosed herein.

A hydrogel composition in accordance with the invention is administered to an individual. An individual is typically a human being of any age, gender or race. Typically, any individual who is a candidate for a conventional procedure to treat a soft tissue condition is a candidate for a method disclosed herein. Although a subject experiencing the signs of aging skin is an adult, subjects experiencing premature aging or other skin conditions suitable for treatment (for example, a scar) can also be treated with a hydrogel composition disclosed herein. In addition, the presently disclosed hydrogel compositions and methods may apply to individuals seeking a small/moderate enlargement, shape change or contour alteration of a body part or region, which may not be technically possible or aesthetically acceptable with existing soft tissue implant technology. Pre-operative evaluation typically includes routine history and physical examination in addition to thorough informed consent disclosing all relevant risks and benefits of the procedure.

The hydrogel composition and methods disclosed herein are useful in treating a soft tissue condition. A soft tissue condition includes, without limitation, a soft tissue imperfection, defect, disease, and/or disorder. Non-limiting examples of a soft tissue condition include breast imperfection, defect, disease and/or disorder, such as, e.g., a breast augmentation, a breast reconstruction, mastopexy, micromastia, thoracic hypoplasia, Poland's syndrome, defects due to implant complications like capsular contraction and/or rupture; a facial imperfection, defect, disease or disorder, such as, e.g., a facial augmentation, a facial reconstruction, a mesotherapy, Parry-Romberg syndrome, lupus erythematosus profundus, dermal divots, scars, sunken checks, thin lips, nasal imperfections or defects, retro-orbital imperfections or defects, a facial fold, line and/or wrinkle like a glabellar line, a nasolabial line, a perioral line, and/or a marionette line, and/or other contour deformities or imperfections of the face; a neck imperfection, defect, disease or disorder; a skin imperfection, defect, disease and/or disorder; other soft tissue imperfections, defects, diseases and/or disorders, such as, e.g., an augmentation or a reconstruction of the upper arm, lower arm, hand, shoulder, back, torso including abdomen, buttocks, upper leg, lower leg including calves, foot including plantar fat pad, eye, genitals, or other body part, region or area, or a disease or disorder affecting these body parts, regions or areas; urinary incontinence, fecal incontinence, other forms of incontinence; and gastroesophageal reflux disease (GERD). As used herein, the term "mesotherapy" refers to a non-surgical cosmetic treatment technique of the skin involving intra-epidermal, intradermal, and/or subcutaneous injection of an agent administered as small multiple droplets into the epidermis, dermo-epidermal junction, and/or the dermis.

The amount of a hydrogel composition used with any of the methods as disclosed herein will typically be determined based on the alteration and/or improvement desired, the reduction and/or elimination of a soft tissue condition symptom desired, the clinical and/or cosmetic effect desired by the individual and/or physician, and the body part or region being treated. The effectiveness of composition administration may be manifested by one or more of the following clinical and/or cosmetic measures: altered and/or improved soft tissue shape, altered and/or improved soft tissue size, altered and/or improved soft tissue contour, altered and/or improved tissue function, tissue ingrowth support and/or new collagen deposition, sustained engraftment of composition, improved patient satisfaction and/or quality of life, and decreased use of implantable foreign material.

Effectiveness of the compositions and methods in treating a facial soft tissue may be manifested by one or more of the following clinical and/or cosmetic measures: increased size, shape, and/or contour of facial feature like increased size, shape, and/or contour of lip, cheek or eye region; altered size, shape, and/or contour of facial feature like altered size, shape, and/or contour of lip, cheek or eye region shape; reduction or elimination of a wrinkle, fold or line in the skin; resistance to a wrinkle, fold or line in the skin; rehydration of the skin; increased elasticity to the skin; reduction or elimination of skin roughness; increased and/or improved skin tautness; reduction or elimination of stretch lines or marks; increased and/or improved skin tone, shine, brightness and/or radiance; increased and/or improved skin color, reduction or elimination of skin paleness; sustained engraftment of composition; decreased side effects; improved patient satisfaction and/or quality of life.

As yet another example, for urinary incontinence procedures, effectiveness of the compositions and methods for sphincter support may be manifested by one or more of the following clinical measures: decreased frequency of incontinence, sustained engraftment, improved patient satisfaction and/or quality of life, and decreased use of implantable foreign filler.

In aspects of this embodiment, the amount of a hydrogel composition administered is, e.g., about 0.01 g, about 0.05 g, about 0.1 g, about 0.5 g, about 1 g, about 5 g, about 10 g, about 20 g, about 30 g, about 40 g, about 50 g, about 60 g, about 70 g, about 80 g, about 90 g, about 100 g, about 150 g, or about 200 g. In other aspects of this embodiment, the amount of a hydrogel composition administered is, e.g., about 0.01 g to about 0.1 g, about 0.1 g to about 1 g, about 1 g to about 10 g, about 10 g to about 100 g, or about 50 g to about 200 g. In yet other aspects of this embodiment, the amount of a hydrogel composition administered is, e.g., about 0.01 mL, about 0.05 mL, about 0.1 mL, about 0.5 mL, about 1 mL, about 5 mL, about 10 mL, about 20 mL, about 30 mL, about 40 mL, about 50 mL, about 60 mL, about 70 g, about 80 mL, about 90 mL, about 100 mL, about 150 mL, or about 200 mL. In other aspects of this embodiment, the amount of a hydrogel composition administered is, e.g., about 0.01 mL to about 0.1 mL, about 0.1 mL to about 1 mL, about 1 mL to about 10 mL, about 10 mL to about 100 mL, or about 50 mL to about 200 mL.

The duration of treatment will typically be determined based on the cosmetic and/or clinical effect desired by the individual and/or physician and the body part or region being treated. In aspects of this embodiment, administration of a hydrogel composition disclosed herein can treat a soft tissue condition for, e.g., about 6 months, about 7 months, about 8 months, about 9 months, about 10 months, about 11 months, about 12 months, about 13 months, about 14 months, about 15 months, about 18 months, or about 24 months. In other aspects of this embodiment, administration of a hydrogel composition disclosed herein can treat a soft tissue condition for, e.g., at least 6 months, at least 7 months, at least 8 months, at least 9 months, at least 10 months, at least 11 months, at least 12 months, at least 13 months, at least 14 months, at least 15 months, at least 18 months, or at least 24 months. In yet aspects of this embodiment, administration of a hydrogel composition disclosed herein can treat a soft tissue condition for, e.g., about 6 months to about 12 months, about 6 months to about 15 months, about 6 months to about 18 months, about 6 months to about 21 months, about 6 months to about 24 months, about 9 months to about 12 months, about 9 months to about 15 months, about 9 months to about 18 months, about 9 months to about 21 months, about 6 months to about 24 months, about 12 months to about 15 months, about 12 months to about 18 months, about 12 months to about 21 months, about 12 months to about 24 months, about 15 months to about 18 months, about 15 months to about 21 months, about 15 months to about 24 months, about 18 months to about 21 months, about 18 months to about 24 months, or about 21 months to about 24 months.

Aspects of the present specification provide, in part, administering a hydrogel composition disclosed herein. As used herein, the term "administering" means any delivery mechanism that provides a composition disclosed herein to an individual that potentially results in a clinically, therapeutically, or experimentally beneficial result. The actual delivery mechanism used to administer a composition to an individual can be determined by a person of ordinary skill in the art by taking into account factors, including, without limitation, the type of skin condition, the location of the skin condition, the cause of the skin condition, the severity of the skin condition, the degree of relief desired, the duration of relief desired, the particular composition used, the rate of excretion of the particular composition used, the pharmacodynamics of the particular composition used, the nature of the other compounds included in the particular composition used, the particular route of administration, the particular characteristics, history and risk factors of the individual, such as, e.g., age, weight, general health and the like, or any combination thereof. In an aspect of this embodiment, a composition disclosed herein is administered to a skin region of an individual by injection.

The route of administration of a hydrogel composition to an individual patient will typically be determined based on the cosmetic and/or clinical effect desired by the individual and/or physician and the body part or region being treated. A composition disclosed herein may be administered by any means known to persons of ordinary skill in the art including, without limitation, syringe with needle, a pistol (for example, a hydropneumatic-compression pistol), catheter, topically, or by direct surgical implantation. The hydrogel composition disclosed herein can be administered into a skin region such as, e.g., a dermal region or a hypodermal region. For example, a hydrogel composition disclosed herein can be injected utilizing needles with a diameter of about 0.26 mm to about 0.4 mm and a length ranging from about 4 mm to about 14 mm. Alternately, the needles can be 21 to 32 G and have a length of about 4 mm to about 70 mm. Preferably, the needle is a single-use needle. The needle can be combined with a syringe, catheter, and/or a pistol.

In addition, a composition disclosed herein can be administered once, or over a plurality of times. Ultimately, the timing used will follow quality care standards. For example, a hydrogel composition disclosed herein can be administered once or over several sessions with the sessions spaced apart by a few days, or weeks. For instance, an individual can be administered a hydrogel composition disclosed herein every 1, 2, 3, 4, 5, 6, or 7 days or every 1, 2, 3, or 4 weeks. The administration a hydrogel composition disclosed herein to an individual can be on a monthly or bi-monthly basis or administered every 3, 6, 9, or 12 months.

Aspects of the present specification provide, in part, a dermal region. As used herein, the term "dermal region" refers to the region of skin comprising the epidermal-dermal junction and the dermis including the superficial dermis (papillary region) and the deep dermis (reticular region). The skin is composed of three primary layers: the epidermis, which provides waterproofing and serves as a barrier to infection; the dermis, which serves as a location for the appendages of skin; and the hypodermis (subcutaneous adipose layer). The epidermis contains no blood vessels, and is nourished by diffusion from the dermis. The main type of cells which make up the epidermis are keratinocytes, melanocytes, Langerhans cells and Merkels cells.

The dermis is the layer of skin beneath the epidermis that consists of connective tissue and cushions the body from stress and strain. The dermis is tightly connected to the epidermis by a basement membrane. It also harbors many Mechanoreceptor/nerve endings that provide the sense of touch and heat. It contains the hair follicles, sweat glands, sebaceous glands, apocrine glands, lymphatic vessels and blood vessels. The blood vessels in the dermis provide nourishment and waste removal from its own cells as well as from the Stratum basale of the epidermis. The dermis is structurally divided into two areas: a superficial area adjacent to the epidermis, called the papillary region, and a deep thicker area known as the reticular region.

The papillary region is composed of loose areolar connective tissue. It is named for its fingerlike projections called papillae that extend toward the epidermis. The papillae provide the dermis with a "bumpy" surface that interdigitates with the epidermis, strengthening the connection between the two layers of skin. The reticular region lies deep in the papillary region and is usually much thicker. It is composed of dense irregular connective tissue, and receives its name from the dense concentration of collagenous, elastic, and reticular fibers that weave throughout it. These protein fibers give the dermis its properties of strength, extensibility, and elasticity. Also located within the reticular region are the roots of the hair, sebaceous glands, sweat glands, receptors, nails, and blood vessels. Tattoo ink is held in the dermis. Stretch marks from pregnancy are also located in the dermis.

The hypodermis lies below the dermis. Its purpose is to attach the dermal region of the skin to underlying bone and muscle as well as supplying it with blood vessels and nerves. It consists of loose connective tissue and elastin. The main cell types are fibroblasts, macrophages and adipocytes (the hypodermis contains 50% of body fat). Fat serves as padding and insulation for the body.

In an aspect of this embodiment, a hydrogel composition disclosed herein is administered to a skin region of an individual by injection into a dermal region or a hypodermal region. In aspects of this embodiment, a hydrogel composition disclosed herein is administered to a dermal region of an individual by injection into, e.g., an epidermal-dermal junction region, a papillary region, a reticular region, or any combination thereof.

Advantageously, some of the present compositions are especially useful and effective in reducing appearance of fine lines, for example, in thin skin regions, of a patient. For example, methods are provided for fine line treatment comprising the steps of administering to the patient a dermal filler composition as described elsewhere herein, at a depth of no greater than about 1 mm.

Other aspects of the present specification disclose, in part, a method of treating a skin condition comprises the step of administering to an individual suffering from a skin condition a hydrogel composition disclosed herein, wherein the administration of the composition improves the skin condition, thereby treating the skin condition. In an aspect of this embodiment, a skin condition is a method of treating skin dehydration comprises the step of administering to an individual suffering from skin dehydration a hydrogel composition disclosed herein, wherein the administration of the composition rehydrates the skin, thereby treating skin dehydration. In another aspect of this embodiment, a method of treating a lack of skin elasticity comprises the step of administering to an individual suffering from a lack of skin elasticity a hydrogel composition disclosed herein, wherein the administration of the composition increases the elasticity of the skin, thereby treating a lack of skin elasticity. In yet another aspect of this embodiment, a method of treating skin roughness comprises the step of administering to an individual suffering from skin roughness a hydrogel composition disclosed herein, wherein the administration of the composition decreases skin roughness, thereby treating skin roughness. In still another aspect of this embodiment, a method of treating a lack of skin tautness comprises the step of administering to an individual suffering from a lack of skin tautness a hydrogel composition disclosed herein, wherein the administration of the composition makes the skin tauter, thereby treating a lack of skin tautness.

In a further aspect of this embodiment, a method of treating a skin stretch line or mark comprises the step of administering to an individual suffering from a skin stretch line or mark a hydrogel composition disclosed herein, wherein the administration of the composition reduces or eliminates the skin stretch line or mark, thereby treating a skin stretch line or mark. In another aspect of this embodiment, a method of treating skin paleness comprises the step of administering to an individual suffering from skin paleness a hydrogel composition disclosed herein, wherein the administration of the composition increases skin tone or radiance, thereby treating skin paleness. In another aspect of this embodiment, a method of treating skin wrinkles comprises the step of administering to an individual suffering from skin wrinkles a hydrogel composition disclosed herein, wherein the administration of the composition reduces or eliminates skin wrinkles, thereby treating skin wrinkles. In yet another aspect of this embodiment, a method of treating skin wrinkles comprises the step of administering to an individual a hydrogel composition disclosed herein, wherein the administration of the composition makes the skin resistant to skin wrinkles, thereby treating skin wrinkles.

In some embodiments, the dermal fillers have a sustained bioavailability. For example, dermal fillers are provided which, when introduced into the skin of a human being, (for example, intradermally or subdermally into a human being for the correction of soft tissue defects of voids in the face), release ascorbic acid (or other vitamin) into the human being for at least about 1 months and up to about 20 months or more.

For example, to predict a sustained Vitamin C efficacy in coordinate with filler duration, an estimation on conjugated degree is made. This estimation was based on the formulation of AA2G conjugation to HA via etherification. The formulation is stable under physiological conditions but start to release of Ascorbic acid (AsA) by α-glucosidase which is attached to the cell membrane. Release of AsA happens at the filler/cell interface due to the fact that α-glucosidase is attached to cell membrane. Further release of AsA from HA-AA2G will be accompanied by HA degradation to make AA2G available to fibroblasts. The release of AsA is thus depending on AA2G conjugation degree and duration of HA. A gel with conjugation degree of 5 mol % approximately could release active Vitamin C in a period of at least up to 1 month, for example, between 3~5 months; a gel with 10 mol % conjugation degree could release active Vitamin C in a period up to 6~8 months; a gel with 15 mol % conjugation degree could release active Vitamin C in a period up to 10~ months; 30 mol % up to one and half years.

| Conjugation degree (mol %) | Total AsA available* (mM) | Calculated number (months)** |
|---|---|---|
| 3 | 2.13 | 2.8 |
| 5 | 3.55 | 3.1 |
| 1 | 7.10 | 6.3 |
| 15 | 10.65 | 9.4 |
| 25 | 17.75 | 15.7 |
| 30 | 21.13 | 18.8 |

*Based on parameters of Gels: volume, 0.1 cc; concentration, 24 mg/ml. (0.1 × 24 × 3% × 1000)/(338 * 0.1) = 2.13 (mM)
**Assumptions:
AsA is released at a constant rate.
Effective concentration of AsA is 0.05 mM and maintains effective >2 days 2.13 * 2/(0.05 * 30) = 2.8 (months)

In an embodiment of the invention, a dermal filler is provided comprising hyaluronic acid crosslinked with a Star-PEG epoxide and having a vitamin C derivative (for example, one of AA2G (Ascorbic acid 2-Glucoside), Vitagen (3-aminopropyl-L-ascorbyl phosphate) and SAP (sodium ascorbyl phosphate) conjugated to the hyaluronic acid with a degree of conjugation of between about 3 mol % and about 40 mol %.

Methods of making this dermal filler include reacting pentaerythritol glycidal ether (Star-PEG epoxide) with ascorbic acid 2-Glucoside (AA2G) at a ratio, reaction temperature and reaction time suitable for achieving a composition containing AA2G capped by 4-arm epoxides (AA2G-4 arm epoxides), unreacted 4-arm epoxides and free AA2G. The 4 arm epoxide capped AA2G (AA2G-4 arm epoxides) is conjugated to hyaluronic acid via the epoxyl group. The unreacted 4 arm epoxides serves as a crosslinker to crosslink hyaluronic acid and as a conjugation agent to further conjugate AA2G.

In another embodiment of the invention, a dermal filler is provided comprising hyaluronic acid crosslinked with BDDE and having a vitamin C derivative (for example, one of AA2G (Ascorbic acid 2-Glucoside), Vitagen (3-aminopropyl-L-ascorbyl phosphate) and SAP (sodium ascorbyl phosphate) conjugated to the hyaluronic acid with a degree of conjugation of between about 3 mol % and about 10 mol %.

Methods of making this dermal filler include reacting BDDE with ascorbic acid 2-Glucoside (AA2G) at a ratio, reaction temperature and reaction time suitable for achieve a composition containing AA2G capped by BDDE (AA2G-BDDE), unreacted BDDE and free AA2G. The BDDE capped AA2G (AA2G-BDDE) is conjugated to hyaluronic acid via the epoxyl group. The unreacted BDDE serves as a crosslinker to crosslink hyaluronic acid and as a conjugation agent to further conjugate AA2G.

Figure 9:
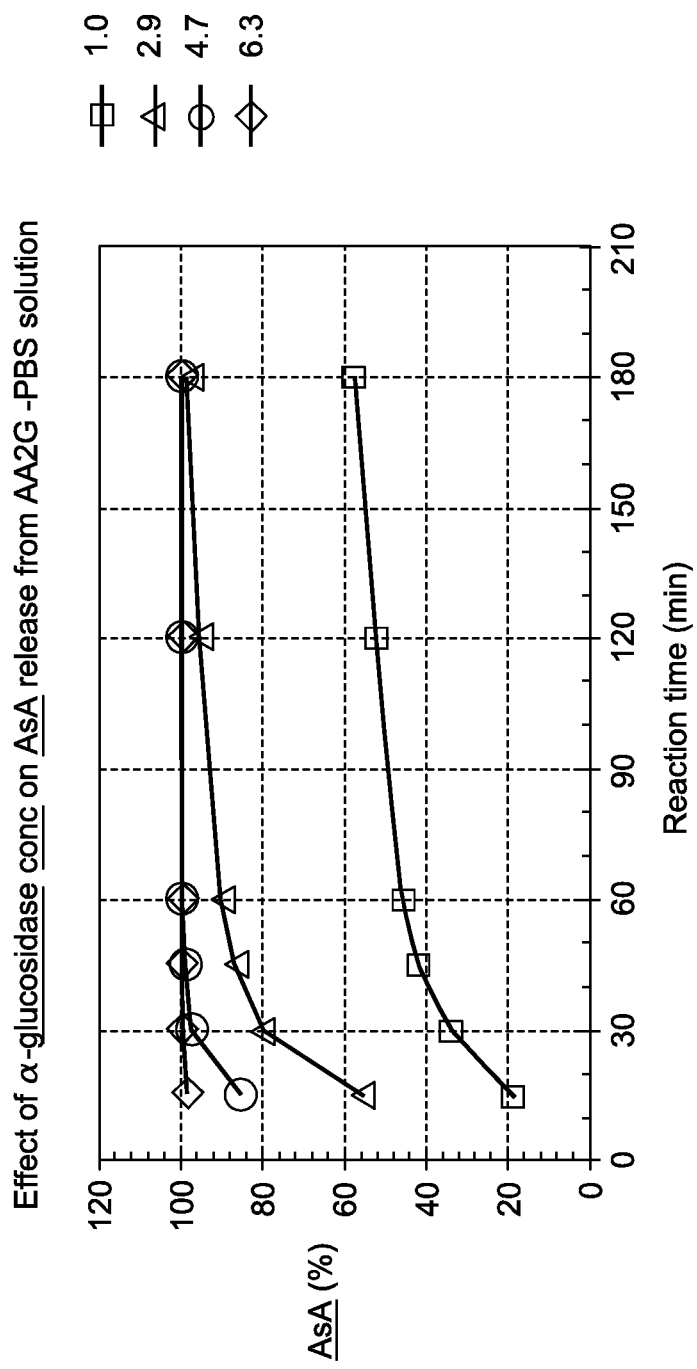
FIG. 9 is a graphical representation of observed percent release of AsA from a solution of AA2G in PBS, in terms of time in minutes, for four different α-glucosidase concentrations.

FIG. 9 is a Table showing the effect of α-glucosidase concentration on AsA release from AA2G-PBS solution. This is an established enzymatic method based on α-glycosidase effectively cleaving AA2G to AsA.
The reaction follows first order kinetics:

$$C = C_0(1 - e^{-kt}).$$

The conversion of AA2G to AsA depends on the concentration of α-glycosidase. 100% conversion of AA2G to AsA is reached within a few minutes at higher enzyme concentrations. AA2G converted AsA almost completely in 15 minutes when α-glycosidase concentration is 6.3 unit per gram gel. When α-glycosidase concentration is 4.7 units per gram gel, It took 30 minutes to completely convert AA2G to AsA. Further decease α-glycosidase concentration resulted in slow conversion of AA2G to AsA.

Figure 10:
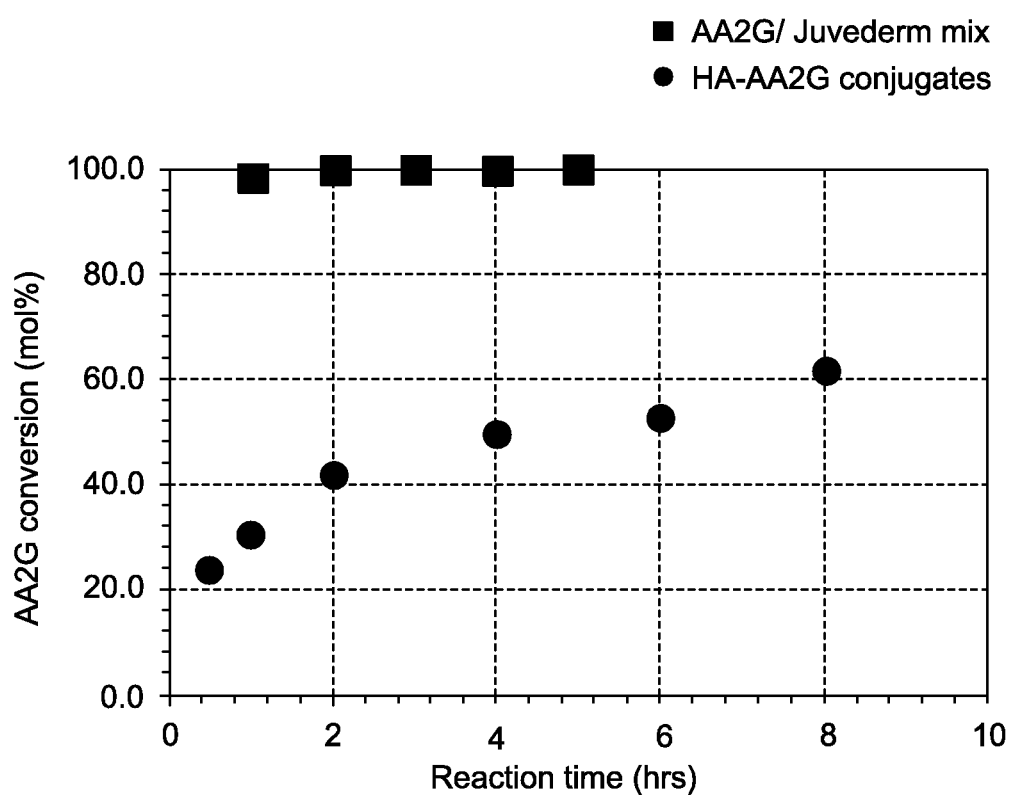
FIG. 10 shows a representation of a release profile of free AsA from conjugated dermal fillers in accordance with the invention (sustained release) (AA2G conversion in mol % versus reaction time).

FIG. 10 shows a representation of a release profile of free AsA from conjugated dermal fillers in accordance with the invention (sustained release) (AA2G conversion in mol % versus reaction time). AA2G completely converted to AsA in AA2G/HA mix in 40 minutes. In comparison, AA2H/HA conjugates showed a time dependence of AA2G conversion to AsA, with about 60 mol % conversions of AA2G at 8 hours, as shown in FIG. 10.

Figure 11A:
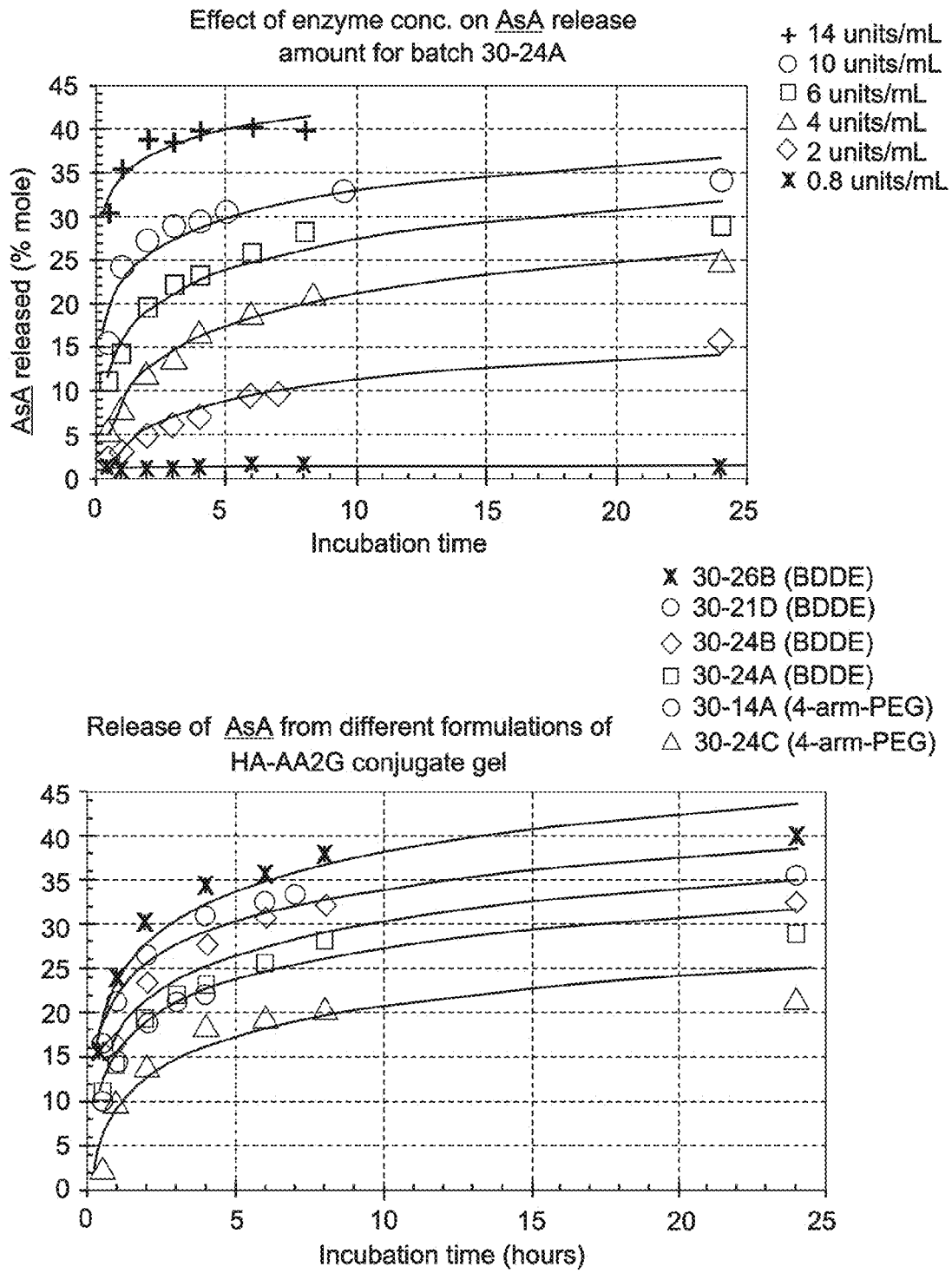
FIGS. 11A and 11B show additional release data for various dermal fillers in accordance with the invention.
Figures 11B, 12:
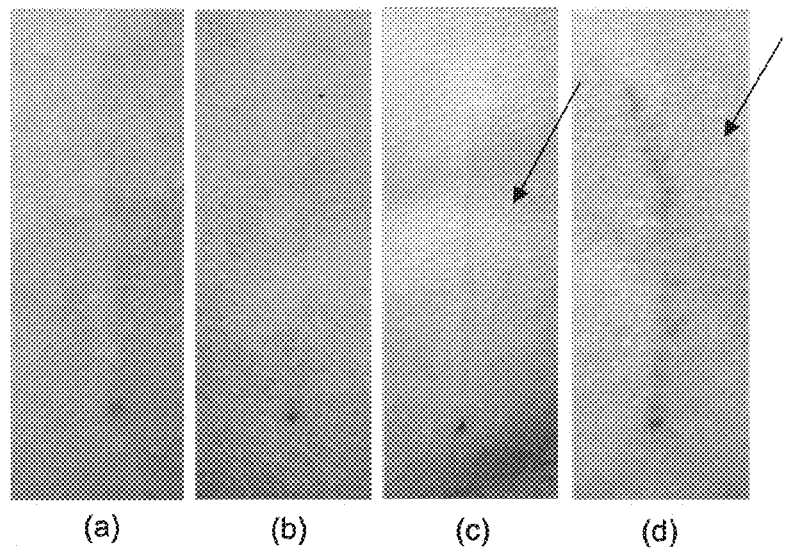
FIG. 12 shows images of skin after superficial injection of HA based dermal filler gels of the invention and some commercially available gels for fine line application.

FIGS. 11A and 11B show additional release data for various dermal fillers in accordance with the invention. More specifically, conversion of AA2G to AsA in HA-AA2G gels is dependent on α-glycosidase concentration. High α-glycosidase concentration resulted in a fast conversion of AA2G to AsA. For a given α-glycosidase concentration, different formulations showed different profiles of AA2G to AsA.

In one aspect of the invention, dermal fillers are provided which are especially effective in treating and eliminating the appearance of fine lines, for example, relatively superficial, creases in the skin, for example, but not limited to, fine lines near the eyes, the tear trough region, forehead, periorbital, glabellar lines, etc.

The appearance of a blue discoloration at the skin site where a dermal filler had been injected, (Tyndall effect) is a significant adverse event experienced by some dermal filler patients. Tyndall effect is more common in patients treated for superficial fine line wrinkles. Embodiments of the present invention have been developed which provide long lasting, translucent fillers which can be injected superficially to treat fine lines and wrinkles, even in regions of relatively thin skin, without any resulting blue discoloration from Tyndall effect. Fine lines or superficial wrinkles are generally understood to be those wrinkles or creases in skin that are typically found in regions of the face (forehead, lateral canthus, vermillion border/perioral lines) where the skin is thinnest, that is, the skin has a dermis thickness of less than 1 mm. On the forehead the average dermal thickness is about 0.95 mm for normal skin and about 0.81 mm for wrinkled skin. Dermis around the lateral canthus is even thinner (e.g. about 0.61 mm for normal skin and about 0.41 mm for wrinkled skin). The average outer diameter of a 30 or 32 gauge needle (needles that are typically used for fine line gel application) is about 0.30 and about 0.24 mm.

The present invention provides a dermal filler composition such as described elsewhere herein, which does not result in Tyndall effect. For example, compositions of the invention comprise a hyaluronic acid component crosslinked with a crosslinking component, an additive other than the crosslinking component; the composition exhibiting reduced Tyndall effect when administered into a dermal region of a patient, relative to composition that is substantially identical except without the additive. The composition may be substantially optically transparent.

In one embodiment, the additive is a vitamin C derivative, for example, AA2G which may be chemically conjugated to the hyaluronic acid as described elsewhere herein.

In some embodiments, the crosslinking component is BDDE and the degree of conjugation is between about 3 mol % and about 10 mol %, or up to 15 mol % or greater. In some embodiments, the composition further comprises an anesthetic agent, for example, lidocaine in an amount suitable for providing comfort to the patient upon injection.

Methods of treating fine lines in the skin of a patient are also provided. The methods generally comprise the steps of introducing into skin of a patient, a composition such as described herein. For example the compositions comprise a mixture of a hyaluronic acid component, a crosslinking component crosslinking the hyaluronic acid, and an additive other than the crosslinking component, the composition being substantially optically transparent; and wherein the dermal filler composition exhibits reduced Tyndall effect relative to composition that is substantially identical except without the additive.

In some embodiments of the invention, the composition comprises a hyaluronic acid component crosslinked with di- or multiamine crosslinker using EDC chemistry. For example, the crosslinker may be HMDA.

In certain embodiments of the invention in which the crosslinker is HMDA, the composition has a G' of up to about 70 Pa, G"/G' between about 0.65 and about 0.75, extrusion force of about 24 N or less, and a final HA concentration of between about 24 mg/g and about 25 mg/g.

In certain embodiments of the invention in which the additive is HA-AA2G conjugate or HA-Vitagen conjugate, the conjugation degree is between about 3 mol % and about 10 mol %, or up to about 15 mol %, or up to about 40 mol %. These compositions may have a G' from at least about 30 Pa, more preferably at least about 40 Pa, to about 100 Pa, G"/G' between about 0.30 and about 0.50, extrusion force of about 27 N or less and a final HA concentration of between about 24 mg/g and about 25 mg/g.

For purposes of the present disclosure, "degree of conjugation" as used herein is defined as molar percentage of conjugant, e.g., AA2G, to the repeating unit of hyaluronic acid (e.g., HA dimer). Thus, 10 mol % conjugation degree means every 100 HA repeat units contain 10 conjugated AA2G. Degree of conjugation can be calculated using the method illustrated in Example 2 below, or other methods known to those of skill in the art.

EXAMPLES

Example 1

AA2G Conjugation to Crosslinked HA Gels Using BDDE as a Crosslinker 400.6 mg of low molecular weight hyaluronic acid (LMW HA) was hydrated in 1802 mg of 1 wt % NaOH in a syringe for ~30 min. 800.7 mg of AA2G was put in a vial, followed by 713.7 mg of BDDE and 1416.8 mg of 10% NaOH. The above solution (pH>12) was allowed to react in a 50° C. water bath for ~20 min, before adding to the hydrated HA. After the addition, the mixture was mixed ~20 times by passing back and forth between 2 syringes. The mixed paste was put in a vial and in the 50° C. water bath for ~2.5 hours. 223.5 mg of 12M HCl was added to 9.05 g PBS, pH7.4. After ~2.5 hours, the HA-AA2G gel was formed. The gel was cut into pieces, and the HCl-PBS solution was added to it. The gel was allowed to neutralize and swell overnight on an orbital shaker. The gel was sized through a ~60 μm screen and mixed ~20 times by passing back and forth between 2 syringes. The gel was put in a 15,000 MWCO RC dialysis bag and dialyzed in PBS, pH 7.4 buffer. The dialysis went on for ~185 hours, with frequent change of PBS buffer. After the dialysis, the gel was put in a syringe and stored in a 4° C. refrigerator.

Example 2

Determination of AA2G Conjugations

The weight of gel as described in Example 1 was noted right before dialysis, and after dialysis. The assumption was made that the gel was ~1 g/mL after dialysis. The dialysis was stopped at the point where no notable AA2G was coming out per >8 hours in 1 L of PBS. The AA2G was measured at 260 nm using UV/Vis spectrophotometer (Nanodrop 2000C, ThermoScientific). The calibration curve of AA2G was calculated using different concentration of AA2G in 2% HA (A@260 nm=1.4838 [AA2G(mM)]).

The weight of HA after dialysis: the starting weight of HA×(actual weight before dialysis/theoretical weight)

The mmol of AA2G after dialysis: put the absorption @ 260 nm after dialysis in the equation (A@260 nm=1.4838 [AA2G(mM)]).

The conjugation @ of AA2G: (mmol of AA2G/mmol of HA)×100%

The AA2G conjugation degree in the gel as described in Example 1 is 14.7 mol %.

Example 3

Determination of Gel Rheological Properties

An oscillatory parallel plate rheometer (Anton Paar, Physica MCR 301) was used to measure the properties of the gel obtained in Example 1. The diameter of plate used was 25 mm. The gap between the plates was set at 1 mm. For each measurement, a frequency sweep at a constant strain was run first, before the strain sweep at a fixed frequency. The G' (storage modulus) was obtained from the strain sweep curve at 1% strain. The value is 1450 Pa for the gel.

Example 4

AA2G Conjugation to Crosslinked HA Gels Using BDDE as a Crosslinker, with Tunable Conjugation Degree and Gel Rheological Properties The procedure was similar to that as described in Example 1. Conjugation degree is modified by tuning crosslinker to HA and AA2G mol ratios. Gel properties were measured as described in Example 3. Details are as follows:

400.8 mg of LMW HA was hydrated in 1752.1 mg of 1% NaOH in a syringe for ~30 min. 800.3 mg of AA2G was put in a vial, followed by 354.1 mg of BDDE and 1402.0 mg of 10% NaOH. The above solution (pH>12) was allowed to react in a 50° C. water bath for ~20 min, before adding to the hydrated HA. After the addition, the mixture was mixed ~20 times by passing back and forth between 2 syringes. The mixed paste was put in a vial and in the 50° C. water bath for ~2.5 hours. 140.9 mg of 12M HCl was added to 9.0053 g PBS, pH7.4. After ~2.5 hours, the HA-AA2G gel was formed. The gel was cut into pieces, and the HCl-PBS solution was added to it. The gel was allowed to neutralize and swell overnight on an orbital shaker. The gel was sized through a ~60 μm screen and mixed ~20 times by passing back and forth between 2 syringes. The gel was put in a 15,000 MWCO RC dialysis bag and dialyzed in PBS, pH7.4 buffer. The dialysis went on for ~164.5 hours, with frequent change of PBS buffer. After the dialysis, the gel was put in a syringe and stored in a 4° C. refrigerator. The conjugation degree is 13%. Gel storage modulus (G') is 803 Pa.

Example 5

AA2G Conjugation to Crosslinked HA Gels Using BDDE as a Crosslinker, Conjugation Degree is 5.3%, G' is ~300 Pa 400.3 mg of LMW HA was hydrated in 3002.0 mg of 1% NaOH in a syringe for ~30 min. 800.5 mg of AA2G was put in a vial, followed by 264.3 mg of BDDE and 1100.0 mg of 10% NaOH. The above solution (pH>12) was allowed to react in a 50° C. water bath for ~20 min, before adding to the hydrated HA. After the addition, the mixture was mixed ~20 times by passing back and forth between 2 syringes. The mixed paste was put in a vial and in the 50° C. water bath for ~2.5 hours. 104.2 mg of 12M HCl was added to 8.5128 g PBS, pH7.4. After ~2.5 hours, the HA-AA2G gel was formed, and the HCl-PBS solution was added to it. The gel was allowed to neutralize and swell over the weekend (~55 hours) on an orbital shaker. The gel was sized through a ~60 μm screen and mixed ~20 times by passing back and forth between 2 syringes. The gel was put in a 15,000 MWCO RC dialysis bag and dialyzed in PBS, pH7.4 buffer. The dialysis went on for ~114 hours, with frequent change of PBS buffer. After the dialysis, the gel was put in a syringe and stored in a 4° C. refrigerator. The conjugation degree and gel rheological properties are measured in a procedure as described in Example 2 and 3. The conjugation degree is 5.3%. Gel storage modulus is ~300 Pa.

Example 6

AA2G Conjugation to Crosslinked HA Gels Using Star-PEG Epoxide as a Crosslinker, Conjugation Degree is 29.4%, G' is ~235 Pa 200.4 mg of LMW HA was hydrated in 2000 mg of 1% NaOH in a syringe for ~30 min. 400 mg of AA2G was put in a vial, followed by 312.7 mg of star-PEG epoxide and 1026.5 mg of 10% NaOH. The above solution was allowed to react in a 50° C. water bath for ~20 min, before adding to the hydrated HA. After the addition, the mixture was mixed ~20 times by passing back and forth between 2 syringes. The mixed paste was put in a vial and in the 50° C. water bath for ~2.5 hours. 187.4 mg of 12M HCl was added to 3.034 g PBS, pH7.4. After ~2.5 hours, the HA-AA2G gel was formed, and the HCl-PBS solution was added to it. The gel was allowed to neutralize and swell over the weekend (~68 hours) on an orbital shaker. The gel was sized through a ~60 μm screen and mixed ~20 times by passing back and forth between 2 syringes. The gel was put in a 15,000 MWCO RC dialysis bag and dialyzed in PBS, pH 7.4 buffer. The dialysis went on for ~95 hours, with frequent change of PBS buffer. After the dialysis, the gel was put in a syringe and stored in a 4° C. refrigerator. The conjugation degree and gel rheological properties are measured in a procedure as described in Examples 2 and 3. The conjugation degree is 29.4%. Gel storage modulus is ~235 Pa.

Example 7

AA2G Conjugation to Crosslinked HA Gels Using Star-PEG Epoxide as a Crosslinker, Conjugation Degree is 27.8%, G' is ~363 Pa 200.3 mg of LMW HA was hydrated in 2000 mg of 1% NaOH in a syringe for ~30 min. 400.2 mg of AA2G was put in a vial, followed by 313.4 mg of star-PEG epoxide and 1022.6 mg of 10% NaOH. The above solution was added to the hydrated HA. After the addition, the mixture was mixed ~20 times by passing back and forth between 2 syringes. The mixed paste was put in a vial and in the 50° C. water bath for ~2.5 hours. 196.5 mg of 12M HCl was added to 3.016 g PBS, pH7.4. After ~2.5 hours, the HA-AA2G gel was formed, and the HCl-PBS solution was added to it. The gel was allowed to neutralize and swell overnight (~24 hours) on an orbital shaker. The gel was sized through a ~60 μm screen and mixed ~20 times by passing back and forth between 2 syringes. The gel was put in a 15,000 MWCO RC dialysis bag and dialyzed in PBS, pH7.4 buffer. The dialysis went on for ~98.5 hours, with frequent change of PBS buffer. After the dialysis, the gel was put in a syringe and stored in a 4° C. refrigerator. The conjugation degree and gel rheological properties are measured in a procedure as described in Examples 2 and 3. The conjugation degree is 27.8%. Gel storage modulus is ~363 Pa.

Example 8

AA2G Conjugation to Crosslinked HMW HA Gels Using BDDE as a Crosslinker, Conjugation Degree is about 10 Mol %, G' is about 240 Pa 400.3 mg of HMW HA was hydrated in 2501.3 mg of 4 wt % NaOH in a syringe for ~30 min. 1200 mg of AA2G was put in a vial, followed by 304.7 mg of BDDE and 1178.6 mg of 16 wt % NaOH. The above solution (pH>12) was allowed to react in a 50° C. water bath for ~20 min and transferred to a 20 cc syringe, before adding to the hydrated HA. After the addition, the mixture was mixed ~20 times by passing back and forth between 2 syringes. The mixed paste was put in a 20 cc vial and in the 50° C. water bath for ~2.5 hours. After ~2.5 hours, the HA-AA2G gel was formed. Then 226.6 mg of 12M HCl was added to 8492.2 mg 10×PBS, pH7.4 to get HCl-PBS solution and the HCl-PBS solution was added to neutralize and swell the gel. The gel was allowed to neutralize and swell over 48 hrs on an orbital shaker. The gel was sized through a ~60 μm screen and mixed ~20 times by passing back and forth between 2 syringes. The gel was put in a 20,000 MWCO CE dialysis bag and dialyzed in PBS, pH7.4 buffer. The dialysis went on for ~114 hours, with frequent change of PBS buffer. After the dialysis, the gel was put in a syringe and stored in a 4° C. refrigerator. The conjugation degree and gel rheological properties are measured in a procedure as described in Examples, 2 and 3. The conjugation degree is 10 mol %. Gel storage modulus is about 240 Pa.

Example 9

Vitagen Conjugation to Crosslinked LMW HA Gels Using BDDE as a Crosslinker, Conjugation Degree is 15 Mol %, G' is about 365 Pa 398.2 mg of LMW HA was hydrated in 1753.24 mg of 1 wt % NaOH in a syringe for ~40 min. BDDE (311.7 mg) was added to swollen HA and continue let HA swell for another 80 min. The swollen HA/BDDE mixture was pre-reacted at 50° C. for 20 min.
801.9 mg of Vitagen was separately dissolved in 1459.7 mg of 10 wt % NaOH and mixed with HA which was pre-reacted with BDDE. The mixture was continued to react at 50° C. for another 2.5 hrs. After ~2.5 hours, the HA-Vitagen gel was formed. Then 195 mg of 12M HCl was added to 9004.0 mg of 10×PBS, pH7.4 to get HCl-PBS solution and the HCl-PBS solution was added to neutralize and swell the gel. The gel was allowed to neutralize and swell over 48 hrs on an orbital shaker. The gel was sized through a ~60 μm screen and mixed ~20 times by passing back and forth between 2 syringes. The gel was put in a 20,000 MWCO CE dialysis bag and dialyzed in PBS, pH7.4 buffer. The dialysis went on for ~120 hours, with frequent change of PBS buffer. After the dialysis, the gel was put in a syringe and stored in a 4° C. refrigerator. The gel rheological properties were measured in a procedure as described in Example 3. The conjugation degree was determined to be about 15 mol % using a similar method as the AA2G determination as described in Example 2. Gel storage modulus is about 365 Pa.

Example 10

Vitagen Conjugation to Linear HA Via Amidization Chemistry 200.3 mg of HMW HA was hydrated in 10 ml of water in 60 cc syringe. 500 mg of Vitagen was dissolved in 0.5 ml of water and solution was neutralized to pH 4.8. 197.7 mg of EDC and 149 mg of NHS were dissolved separately in 6 ml of water. The above solutions (solutions and EDC/NHS solutions) are added to another 60 cc syringe containing 23.5 ml of water. The two syringes are mixed 20 times by passing back and forth between 2 syringes. The mixtures was stored in one syringe and soaked in 37° C. bath for 4 hrs. The solutions was finally dialyzed against PBS pH7.4 buffer until no noticeable Vitagen was observed. The conjugation degree was determined by a similar method as described Example 3. The conjugation degree is about 10 mol %.

Example 11

AA2P Conjugations to Crosslinked HA Gels 200.4 mg of LMW HA is hydrated in 1000 mg of MES 5.2 buffer in a syringe for ~30 min. 292 mg of AA2P is put in a vial, followed by 300 mg of star-PEG amine added. The above solution is allowed to react at room temperature overnight. The gel was hydrated with PBS buffer and dialyzed against PBS buffer to remove unreacted AA2P. The finally gel was characterized as described in Examples 2 and 3 to determine the conjugation degree and gel rheological properties. The conjugation degree is about 20 mol %. The storage modulus (G') is about 500 Pa.

Example 12

Formulation of a HA/BDDE Dermal Filler Product with AA2G for Reducing Appearance of Fine Lines To any of the gels described in the above Examples, after dialysis, a suitable amount of free HA gel may be added to the gel to improve of modify gel cohesivity and/or injectability. For example, free HA fibers are swollen in a phosphate buffer solution, in order to obtain a homogeneous viscoelastic gel ("free" HA gel). This uncrosslinked gel is added, before the dialysis step, to the HA/BDDE crosslinked gel obtained in Example 1 (for example, to obtain a composition having between about 1% to about 5%, w/w free HA). The resulting gel is then filled into Ready-to-Fill sterile syringes and autoclaved at sufficient temperatures and pressures for sterilization for at least about 1 minute. After autoclaving, the final HA/AA2G product is packaged and distributed to physicians to use as a dermal filler for superficial injection to improve the appearance of fine lines in the periorbital or other facial region.

Example 13

Formulation of HA-AA2G Dermal Filler Including Lidocaine

The procedure of Example 12 is followed, but after the dialysis step and before the addition of free HA gel, lidocaine chlorhydrate (lidocaine HCl) is added to the mixture. The (lidocaine HCl) in powder form may first be solubilized in WFI and filtered through a 0.2 μm filter. Dilute NaOH solution is added to the cohesive HA/AA2G gel in order to reach a slightly basic pH (for example, a pH of between about 7.5 and about 8). The lidocaine HCl solution is then added to the slightly basic gel to reach a final desired concentration, for example, a concentration of about 0.3% (w/w). The resulting pH of the HA/AA2G/lidocaine mixture is then about 7 and the HA concentration is about 24 mg/g. Mechanical mixing is performed in order to obtain a proper homogeneity in a standard reactor equipped with an appropriate blender mechanism.

Example 14

Conjugations of Additives Containing Carboxyl Functional Group to HA Hydrogels

Additives such as retinoic acid (AKA, tretinoin), adapalence and alpha-lipoic acid contain carboxyl functional group (—COOH). These additives are conjugated to HA hydrogels via esterifications using EDC chemistry. An example for the conjugations in accordance with an embodiment of the invention is described as follows:

200 mg of HMW HA is hydrated in 10 ml of pH 4.8 MES buffer in 60 cc syringe. In another syringe, 200 mg of retinoic acid is dissolved in 5 ml of water-acetone mixture (water/acetone volume ratio 1:3). The above two syringes are mixed via a syringe connector for about 20 times. Then 197.7 mg of EDC and 149 mg of NHS are dissolved separately in 6 ml of water in a separate syringe. The syringe containing EDC and NHS is connected the syringe containing with HA and retinoic acid to allow reactants to mix at least for 20 times by passing back and forth between 2 syringes. The mixtures are stored in one syringe and soaked in 37° C. bath for 4 hrs. The gels are dialyzed against isopropanol to remove unconjugated Retinoic acid, and then dialyzed against PBS buffer under aseptic conditions. The gels are packaged into sterilized syringes and stored at 4° C.

Example 15

Conjugations of Additives Containing Hydroxyl Functional Group to HA Hydrogels

Additives such as retinol (AKA, tretinoin), catalase, dimethylaminoethanol and g-Tocopherol contain hydroxyl functional group (—OH). These additives are conjugated to HA hydrogels via esterifications using EDC chemistry. A typical example for the conjugations is described as follows:

200 mg of HMW HA is hydrated in 10 ml of pH 4.8 2-(N-morpholino) ethanesulfonic acid (MES) buffer in 60 cc syringe. In another syringe, 200 mg of retinol acid is dissolved in 5 ml of water-acetone mixture (water/acetone volume ratio 1:3). The above two syringes are mixed via a syringe connector for about 20 times. Then 197.7 mg of EDC and 149 mg of NHS are dissolved separately in 6 ml of water in a separate syringe. The syringe containing EDC and NHS is connected the syringe containing with HA and retinol to allow reactants to mix at least for 20 times by passing back and forth between 2 syringes. The mixtures are stored in one syringe and soaked in 37° C. bath for 4 hrs. The gels are dialyzed against isopropanol to remove unconjugated retinol, and then dialyzed against PBS buffer under aseptic conditions. The gels are packaged into sterilized syringes and stored at 4° C.

Example 16

Conjugations of Additives Containing Hydroxyl Functional Group to HA Hydrogels by Post-modifications This is a two-step process.

Step one: A crosslinked HA gel, for example, a commercial HA-based dermal filler, for example, JUVEDERM®, Allergan, Irvine Calif., or Restylane® Medicis Aesthetics, Inc. is treated with EDC/NHS to activate the carboxyl group of HA.

Step 2: the activated HA hydrogel is treated with additives containing hydroxyl groups. Additives containing hydroxyl groups are retinol, catalase, dimethylaminoethanol and g-Tocopherol hydroxyl functional group (—OH).

A typical examples for the conjugation of additives to crosslinked HA gels is as follows:

2 gm of Juvederm gel is mixed with 200 gm of EDC and 150 mg of NHS at room temperature. Then 200 mg of retinol in 3 ml of acetone-water mixture is added. The above mixture is reacted at 37° C. for 4 hrs. The gels are dialyzed against isopropanol to remove unconjugated Retinol, and then dialyzed against PBS buffer under aseptic conditions. The gels are packaged into sterilized syringes and stored at 4° C.

Example 17

Conjugation of Growth Factors, Peptides, or Elastin to HA Hydrogels

Additives such as epidermal growth factor (EGF), transforming growth factor (TGF) and peptides contain functional amine groups may be conjugated to HA to form beneficial dermal fillers. These additives are conjugated to HA via amidization chemistry. A typical example for conjugating is described as follows:

200.3 mg of HMW HA is hydrated in 10 ml of MES pH 5.4 buffer water. 20 mg of EGF in 100 mg of MES solution is added. To above mixture, 197.7 mg of EDC and 149 mg are added. The resulting reaction mixture is allowed to react at 37° C. for 4 hrs. After the reaction completes, the gel is further dialyzed against isopropanol and then dialyzed against PBS buffer under aseptic conditions. The gels are packaged into sterilized syringes and stored at 4° C.

The present invention further provides methods of enhancing viability of grafted adipose tissue. The methods may generally comprise the steps of introducing a composition into the skin of a patient adjacent grafted adipose tissue, the composition being a composition as described elsewhere herein. For example, the composition may comprise hyaluronic acid and a vitamin C derivative covalently conjugated to the hyaluronic acid, wherein a degree of conjugation is between about 3 mol % and about 40 mol %. In other aspects of the invention, methods for treating skin include the steps of introducing, into skin, a composition comprising adipose tissue, hyaluronic acid and a vitamin C conjugated to the hyaluronic acid.

Example 18

Conjugation of Growth Factors, Peptides, or Elastin to HA Hydrogels

To evaluate the mitogenic effects of vitamin C and its derivatives on human adipose tissue derived stem cells (hASCs), hASCs were cultured on tissue culture plastic for 4 days in complete MesenPro medium (Invitrogen, Carlsbad, Calif.) supplemented with or without vitamin C (ascorbic acid) or its derivatives (Vitagen or AA2G) in free form. Proliferation was assessed by MTT assay as described by the manufacturer (ATCC, Manassas, Va.). After 4 days, concentrations of ascorbic acid, 0.25, 0.5, and 1 mM, were found to enhance proliferation (measured by amount of conversion of yellow tetrazolium MTT into purple formazan by dehydrogenase enzymes (the purple formazon is solubilized by detergent) by 60%, 80%, and 96% above controls lacking ascorbic acid, respectively. Using the same concentrations of AA2G yielded proliferation enhancements of 70%, 60%, and 50% above controls, respectively. Similar results were obtained with Vitagen, showing 70%, 60%, and 30% increases over controls, respectively. In summary, vitamin C and its derivatives, AA2G and vitagen, in the presence of growth factor containing media, enhance hASC proliferation in cell culture.

Crosslinked HA Gels with Conjugated Vitamin C

Preparation of crosslinked HA-based gels with conjugated vitamin C and using 1,4-butanediol diglycidylether (BDDE) as a crosslinker, in accordance with certain embodiments of the invention which exhibit reduced Tyndall effect and other advantages are described in Examples 19 and 20 below. In Example 19, the vitamin C derivative is ascorbic acid 2-glucoside (AA2G) and in Example 20, the vitamin C derivative is ascorbyl 3-aminopropyl phosphate (Vitagen). These gels have optimal rheological properties, excellent injectability and high HA concentration (25 mg/g). Although not wishing to be bound by any specific theory of operation, it has been discovered by the present inventors that crosslinking HA with BDDE in the presence of either AA2G or Vitagen greatly changes the properties of the gels, with gels having high crosslinked densities, high HA concentrations, low viscosities and low extrusion forces, relative to commercial HA gels crosslinked with BDDE. Since AA2G or Vitagen is present during crosslinking, the present gels formed have these ascorbic acid derivatives coupled to the HA chains as both pendent groups, and as crosslinkers bridging HA chains, either alone, or via BDDE. The microscopic structure of the gel is greatly changed, resulting in gels that have very low extrusion force, even through needles as fine as 30 gauge. Moreover, the gels have between about 3 mol % to about 10 mol %, or up to about 15 mol %, of vitamin C conjugated to HA. When the gels are injected, they release active Vitamin C by endogeneous enzymes such as α-glucosidase from fibroblasts or phosphotase. The active vitamin C may trigger skin collagenesis and may act as a radical scavenger to inhibit gel degradation.

Example 19

Formulation of a HA/AA2G Gel with Reduced Tyndall Effect

A mixture of 400.1 mg of LMW HA and 402.3 mg AA2G in a syringe, was hydrated for 60 min after adding 1764.0 mg of a 5 wt % NaOH solution. In a separate vial was added 800.8 mg of AA2G, followed by 1401.1 mg of an 9.1 wt % NaOH solution, and 252.6 mg of BDDE. The resulting solution (pH>12) was allowed to react in a 50° C. water bath for ~20 min, before it was transferred to the hydrated HA. After the addition, the mixture was mixed ~20 times by passing it back and forth two syringes. The paste was then transferred in a vial before it was placed in a 50° C. water bath for ~2.5 hours. After crosslinking, a solution containing 197.0 mg of 12 M HCl and 9.18 g 10×PBS, pH 7.4 was added to neutralize the base, and swell the gel for 72 h on an orbital shaker. The gel was sized by forcing it through a ~60 µm pore size mesh. The sized gel was mixed ~20 times by passing it back and forth two syringes before it was transferred into a cellulose ester dialysis bag, MWCO ~20 kDa and dialyzed against PBS, pH 7.4 buffer for 5 days changing the buffer twice daily. After dialysis, the gel was dispensed into 1 ml COC syringes, centrifuge at 5000 RPM for 5 min to remove air bubbles, and sterilized with moist steam. The gel had final HA concentration of 25 mg/g, an AA2G mol % calculated as described in Example 2 of about 10 mol %, and a G' of about 80 Pa. Other gels were made in a similar manner with G' values of about 60 Pa to about 80 Pa.

Example 19A

Formulation of a HA/AA2G with Lidocaine Gel with Reduced Tyndall Effect

To the gel of Example 19, an amount of lidocaine was added to produce a HA/AA2G with lidocaine gel having 0.3% ww lidocaine. A solution of lidocaine was prepared by dissolving lidocaine HCl in PBS buffer pH ~7.4. An aliquot of the lidocaine solution was added to the gel in Example 19 after dialysis but before sterilization. The gel was then thoroughly mixed to obtain a homogenized mixture with a 0.3% w/w lidocaine concentration.

Example 20

Formulation of a HA/Vitagen Gel with Reduced Tyndall Effect 401.0 mg of LMW HA was hydrated in 2355.0 mg of 1 wt % NaOH solution in a syringe for ~45 min. 303.8 mg BDDE of was added to the hydrated HA and mix 10 times by syringe-to-syringe mixing. The mixture was pre-reacted in a 50° C. water bath for 15 min. 800.1 mg of Vitagen was separately dissolved in 950.6 mg of 15 wt % NaOH, followed by 510.1 Milli-Q water. The Vitagen solution was mixed with the pre-heated hydrated HA/BDDE mixture 30 times back and forth using syringe-to-syringe mixing. The mixture was placed back in the 50° C. water bath and the reaction proceeded for another 2 h after which a solution containing 148.1 mg of 12M HCl and 8523.1 mg of 10×PBS, pH7.4 was added to the cross The HCl-PBS solution was added to neutralize and swell the gel. The gel was allowed to neutralize and swell over 48 hrs on an orbital shaker. The gel was sized through a ~60 µm screen and mixed ~20 times by passing back and forth between 2 syringes. The gel was put in a 20,000 MWCO CE dialysis bag and dialyzed in PBS, pH7.4 buffer. The dialysis went on for ~197 hours, with frequent change of PBS buffer. After the dialysis, the gel was transferred into 1 ml COC syringes, centrifuge at 5000 RPM for 5 min, and sterilized with moist steam. The final HA concentration of the gel was 24 mg/g.

Crosslinked HA Gels Via
1-Ethyl-3-[3-Dimethylaminopropyl]Carbodiimide
Hydrochloride (EDC) Chemistry Preparation of crosslinked HA-based gels, in accordance with certain embodiments of the invention which exhibit reduced Tyndall effect and other advantages are described in Examples 21 and 22 below. In Example 21, the gel is made via EDC chemistry using crosslinker is hexamethylene diamine (NMDA), and in Example 20, 3-[3-(3-amino propoxy)-2,2-bis(3-amino-propoxymethyl)-propoxy]-propylamine (4 arm amine-4 AA). Crosslinking is carried out under mild conditions, e.g. room temperature, and for example, at pH 5.4. The reactions conditions could be tuned to prepare highly reticulate gels with optimal gel properties, excellent injectability and high final HA concentrations (~24 mg/g). It has been discovered by the inventors that it may be advantageous to crosslink HA at very low hydration or reaction concentrations, with a moderate amount of either HMDA or 4 AA, in conjunction with 1-ethyl-3-(3-dimethylaminopropyl) carbodiimide hydrochloride (EDC) and N-hydroxysuccinimide (NHS) or sulfonyl-NHS (sulfo-NHS), the coupling agents. The gels will have crosslinked points that are far from each other hence highly crosslinked materials which have high damping force. In contrast, crosslinking of HA with BDDE at such low hydration or reaction concentrations may be impracticable because of the relative inefficiency of the crosslinker.

Example 21

Formulation of a HA/HMDA Gel with Reduced Tyndall Effect 20.0 g of 100 mM MES buffer pH 5.2 was added to a syringe containing 1000.0 mg of LMW HA. HMDA solution was prepared by dissolving 260.9 mg HMDA.HCl in 2010.5 mg of 100 mM MES buffer pH 5.2, and adding 2 µl of 1M NaOH to bring pH to 5.2. EDC solution was prepared by dissolving 254.2 mg of EDC in 1188.4 mg 100 mM MES buffer pH 5.2, and in a separate vial, 44.3 mg of NHS was dissolved in 1341.8 mg of 100 mM MES buffer pH 5.2. Upon full hydration of the HA, ~1 h, 790 µl of the HMDA solution was added to the hydrated HA. The mixture was homogenized by 10 times syringe-to-syringe mixing. 490 µl EDC and 490 µl NHS solutions were then added to the homogenized paste and again mix 10 times by syringe-to-syringe mixing. The mixture was then transferred to a vial and crosslinked at room temperature for 5 h. before the addition of 17.9 ml of 1×PBS buffer pH 7.4. The gel was allowed to swell for 3 days on a roller before it was force through a 60 µm pore size mesh. The sized gel was placed in a cellulose ester membrane dialysis tubing MWCO 20 KDa and dialyzed against 1×PBS for 4 days changing the buffer twice a day. The gel was dispensed in 1 ml COC syringes, centrifuge at 5000 RPM for 5 min, and sterilized with moist steam. The final HA concentration of the gel was 25 mg/g.

Example 22

Formulation of a HA/4 AA Gel with Reduced Tyndall Effect 32.55 g of 100 mM MES buffer pH 5.2 was added to a syringe containing 1000.4 mg of LMW HA. 4 AA solution was prepared by dissolving 256.3 mg 4 AA in 1039.8 mg of 100 mM MES buffer pH 5.2, and adding 380 µl of 6 M HCl to bring pH to 5.2. EDC solution was prepared by dissolving 251.2 mg of EDC in 1013.8 mg 100 mM MES buffer pH 5.2, and in a separate vial, 74.7 mg of NHS was dissolved in 2020.0 mg of 100 mM MES buffer pH 5.2. Upon full hydration of the HA, ~1 h, 260 µl of the 4 AA solution was added to the hydrated HA. The mixture was homogenized by 10 times syringe-to-syringe mixing. 277 µl EDC and 273 µl NHS solutions were then added to the homogenized paste and again mix 10 times by syringe-to-syringe mixing. The mixture was then transferred to a vial and crosslinked at room temperature for 5 h. before the addition of 6.4 ml of 10×PBS buffer pH 7.4. The gel was allowed to swell for 3 days on a roller before it was force through a 60 µm pore size mesh. The sized gel was placed in a cellulose ester membrane dialysis tubing MWCO 20 KDa and dialyzed against 1×PBS for 4 days changing the buffer twice a day. The gel was dispensed in 1 ml COC syringes, centrifuge at 5000 RPM for 5 min, and sterilized with moist steam. The gel had a final HA concentration of 23 mg/g.

Example 23

Determination of Rheological Properties of Gels of Examples 19-22

An Oscillatory parallel plate rheometer, Anton Paar Physica MCR 301, was used to measure the rheological properties of the gels. A plate diameter of 25 mm was used at a gap height of 1 mm. Measurements were done at a constant temperature of 25° C. Each measurement consisted of a frequency sweep from 1 to 10 Hz at a constant strain of 2% and a logarithmic increase of frequency followed by a strain sweep from 1 to 300% at a constant frequency of 5 Hz with a logarithmic increase in strain. The storage modulus (G') and the viscose modulus (G") were obtained from the strain sweep at 1% strain.

Storage and Viscous Moduli of Gels Obtained from Examples 19-22

| Sample ID | Storage Modulus (G') Pa | Viscous Modulus (G") Pa |
| --- | --- | --- |
| Example 19 | 84 | 25 |
| Example 20 | 83 | 33.7 |
| Example 21 | 67 | 42 |
| Example 22 | 41 | 29.5 |

Example 24

Extrusion Force Measurements of Gels of Examples 19-22

The force required to extrude the gels through a 30 gauge needle was measured using an Instron 5564 and a Bluehill 2 software. The gels were extruded from a 1 ml COO syringe through a 30 G½ TSK needle. The plunger was pushed at a speed of 100 mm/min for 11.35 mm, and the extrusion force was recorded.

Extrusion Force of Gels Obtained from Examples 19-22

| Sample ID | Extrusion force (N) |
| --- | --- |
| Example 19 | 25 |
| Example 20 | 24 |
| Example 21 | 22 |
| Example 22 | 19.5 |

Example 25

Biocompatibility Testing of Gels of Examples 19-22

50 µl bolus injections of gel were implanted intradermally in the dorsal surface of Sprague Dawley rats. The implants were removed at 1 week and analyzed by histology with hematoxylin and eosin (H&E) staining, and CD68 staining which is a marker for mononuclear inflammation cells. Three 20× images of CD68 were scored from 0-4 based on the degree of staining. These values were then averaged out to give a sample score. Four samples were analyzed from each gel.

Average CD68 Scores of Examples 19-22

| Sample ID | Score |
|---|---|
| Example 1 | 1.8 |
| Example 2 | 1.6 |
| Example 3 | 2.7 |
| Example 4 | 1.3 |

Example 26

Cytotoxicity Testing of Gels of Examples 19-22, ISO 10993-5

In Vitro cytotoxicity tests of the gels were performed by NAMSA according to the Agarose Overlay Method of ISO 10993-5: biological Evaluation of Medical Devices—Part 5: Tests for In Vitro Cytotoxicity. Triplicate wells were dosed with 0.1 ml of test articles placed on a filtered disc, as well as 0.9% NaCl solution, 1 cm length of high density polyethylene as a negative control, and 1×1 $cm^2$ portion of latex as a positive control. Each was placed on an agarose surface directly overlaying a monolayer of L929 mouse fibroblast cells. After incubating at 37° C. in 5% $CO_2$ for 24 h. the cultures were examined macroscopically and microscopically for any abnormal cell morphology and cell lysis. The test articles were scored from 0-4 based on the zone of lysis in the proximity of the samples. Test materials from examples 1, 3, and 4 scored 0 as test articles showed no evidence of causing any cell lysis or toxicity.

Quantitative Analysis of Tyndall Effect

In order to further support visual observations and carry out comparative performance analysis of HA fillers, it was deemed necessary to do a quantitative analysis of Tyndall effect. As such no quantitative techniques for Tyndall effect specific to dermal fillers exist in the literature. However, based on existing scientific understanding on light scattering and interaction of light with skin, two distinct approaches based on (a) colorimetry, and (b) spectroscopy were employed to quantify Tyndall effect in skin. Based on these techniques three distinct quantitative parameters (outlined below) were defined to measure Tyndall effect in vivo.
a) Tyndall Effect Visual Score: The scale had a range of 1 to 5 with increments of 0.5. A score of 1 was given to injection sites with normal skin tone and no blue discoloration. A maximum score of 5 was given to thick and pronounced blue discoloration (typically associated with Restylane or Juvéderm Ultra Plus). Three independent observers were trained on the scale before being blinded to score test samples.
b) Blue Component of Skin Color—"b": A chromameter (CM2600D, Konica Minolta, NJ) was used to quantify the blue color component of light remitted from skin sites injected with the various fillers. This was achieved by using the "b" component of L-a-b color scale.
c) "% Blue Light" Remitted from Skin: A portable spectrophotometer (CM2600D, Konica Minolta, NJ) was used to quantify the % blue light remitted from skin in the total visible light range. This was achieved by integrating the area under the visible light spectrum between 400-490 nm and normalizing it by the total area under the spectrum (400-700 nm).

Example 27

Tyndall Evaluation of Gels

Gels were injected intradermally through a 27 G½ TSK needle using linear threading technique into the thighs of two months old hairless rats. The gels were implanted superficially to mimic clinical fine line procedures. Tests for Tyndall were performed 48 h after gel implantation. Before performing the Tyndall tests, the animals were euthanized to improve contrast of the Tyndall effect due to lack of hemoglobin.

Images of gels from Examples 19 and 21, 2 days after implantation, are shown in FIG. 12. Images for commercial Juvéderm Refine and Restylane Touch are also shown for comparison. A bluish line (Tyndall effect) is clearly visible in the images of commercial gels Juvéderm Refine and Restylane Touch. Gels from Examples 19, 19A (not shown) and 21 exhibited no Tyndall effect.

Figure 13:
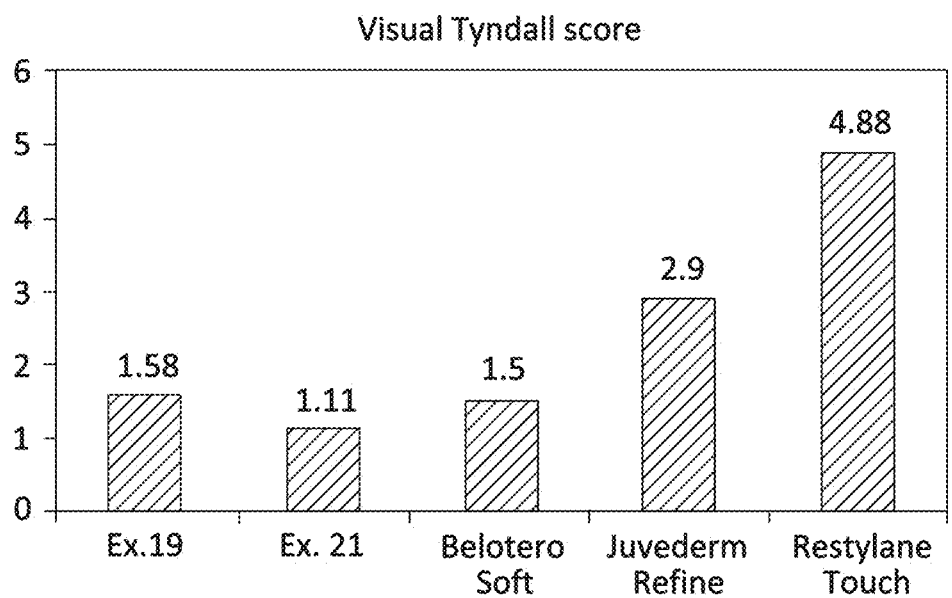
FIG. 13 shows visual Tyndall scores of HA based dermal filler gels of the invention and certain commercially available gels for fine line application.
Figure 14:
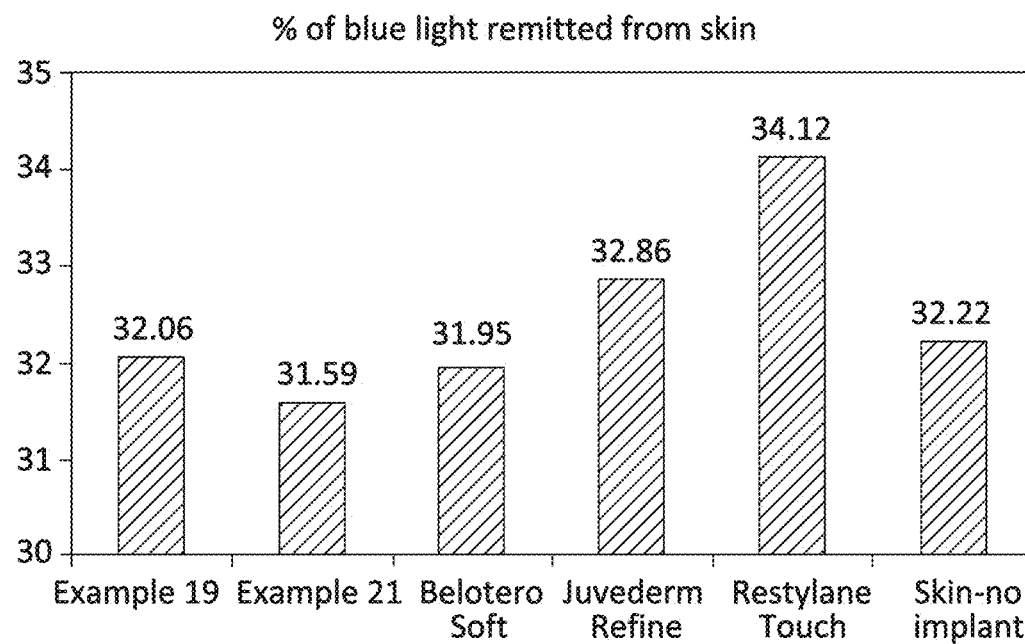
FIG. 14 shows % of blue light remitted from skin of HA based dermal filler gels of the invention and some commercially available gels for fine line application

A visual score of 1-5 with increments of 0.5, was used to score the injection sites. Injection sites with score of 1 showed no skin discoloration, while injections sites with score of 5 showed severe blue discoloration of the skin. Spectroscopic analyses were also performed on the injection sites with the aid of a chromatometer (CM2600D, Konica Minolta, NJ). The blue component of skin color "b", and the % of blue light remitted from skin (400-700 nm) were independently measured. FIGS. 13 and 14, show visual Tyndall score and % of blue light remitted. Gels from Examples 19 and 21 showed no Tyndall effect, and had lower visual Tyndall score and % of blue light remitted values. The Tyndall score and % of remitted blue light values were higher for Juvéderm Refine and Restylane Touch. Belotero Soft did not show any Tyndall and values were comparable to those of Examples 19 and 21. See FIGS. 13 and 14.

Example 28

In vivo Duration Evaluation of Gels by Histology

Figure 15:
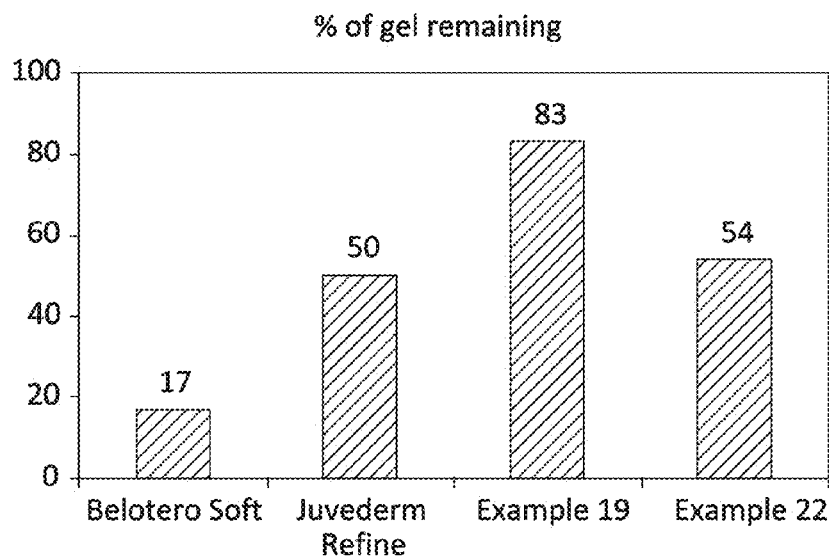
FIG. 15 shows overall % of gel remaining after 1 week implantation of HA based dermal filler gels of the invention and some commercially available gels for fine line application.

50 μl bolus injections of gels of the invention and commercial gels were implanted intradermally in the dorsal surface of Sprague Dawley rats. The implants were removed at 1 week and analyzed by histology with hematoxylin and eosin (H&E) staining. Sections were taken at exactly at the injection sites. Two sections were cut from each tissue sample and the H&E stained section was stitched using a stitching scope. The samples were then grouped and scored as follows; none (0%), low (25%), medium (50%), and high (100%) depending on the amount of material remaining. See FIG. 15.

Example 28A

In vivo Duration Evaluation of Gels by MRI

Figure 16:
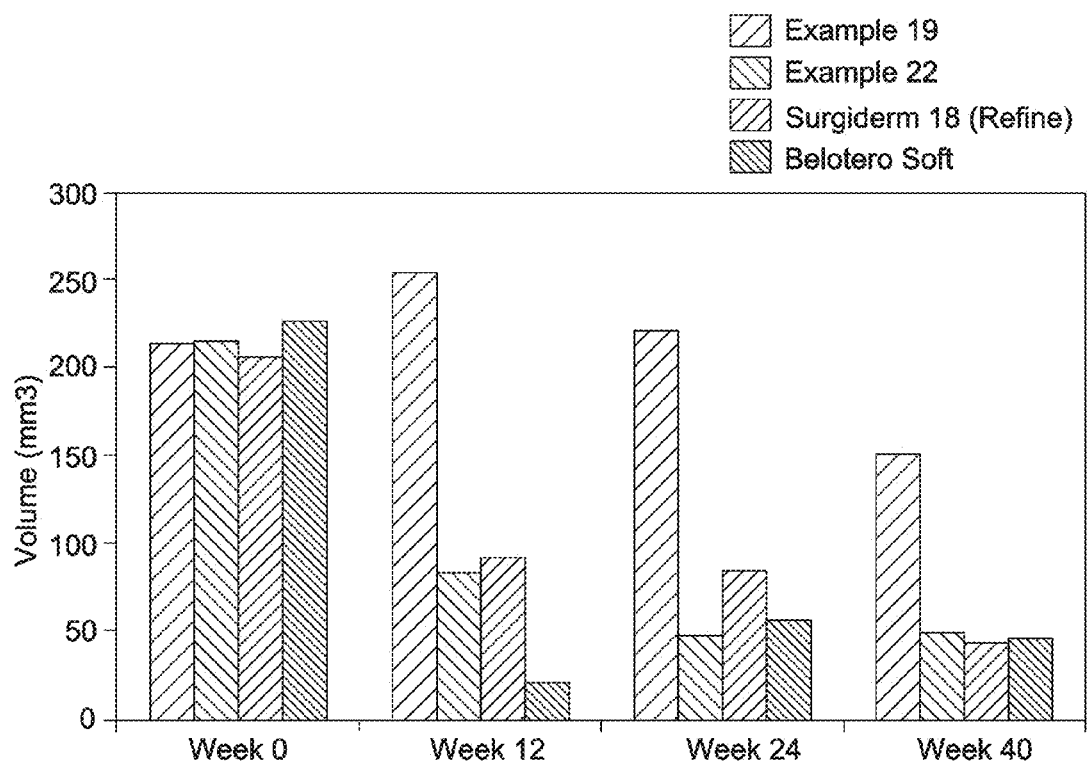
FIG. 16 shows overall % of gel remaining at Week 0, Week 12, Week 24 and Week 40 of implanted HA based dermal filler gels of the invention and some commercially available gels for fine line application.

Magnetic Resonance Imaging (MRI) study was used to evaluate the volume and surface area change with time of gels of the invention and commercial gels over a period of 40 weeks, after intradermal injections in female Sprague-Dawley rats. The gels were injected at a target volume of 150 μl per implant. Implants were located at two contralateral sites slightly caudal to shoulder, two contralateral sites slightly rostral from knee, and two contralateral sites midpoint between head and tail. MRI scans were performed on a 7 Tesla 70/30 Bruker Biospec MRI scanner. Images were collected on the day of implantation (week 0), and at 12, 24, 40 weeks after implantation. Plots of absolute volume of gel versus Time is shown in FIG. 16 below. High persistence gels have high absolute volume at 40 weeks implantation.

Example 29

Compositions of the Invention as Used in the Treatment of Periorbital Lines

A 40 year old thin woman presents with fine wrinkles in the periorbital region and requests dermal filler treatment. Using a 30 gauge needle, the physician introduces 0.6 ml of a HA-based gel in accordance with the invention (such as that described in Example 19) superficially into the fine lines beneath each of her eyes and in the tear trough region using linear threading technique. Although the gel is introduced superficially, no blue discoloration is observed and the patient is satisfied with the results.

As shown, compositions of the present invention, for example, those of Examples 19 and 21, have reduced or insignificant Tyndall effect, and substantially longer duration in the body relative to certain HA-based commercial gels, for example, Juvederm Refine/Surgiderm 18 and Belotero Soft. Relative to Belotero Soft, the gels of the present invention had not only a Tyndall score at least as favorable as this commercial gel, but advantageously exhibited substantially higher in vivo duration.

Example 30

Injectable Compositions of the Invention for Improvement of the Appearance of Fine Lines Additives such as Vitamin A, Vitamin B, Vitamin C, Vitamin D, Vitamin E and derivatives thereof, alone and in combination, are conjugated to crosslinked hyaluronic acid gels in a manner so as to produce a variety of substantially optically transparent, injectable HA-based gels. The HA component is at least 90% by weight, for example, is substantially entirely low molecular weight HA, or about 100% low molecular weight HA, as defined elsewhere herein. These additives are conjugated to HA hydrogels using any suitable means. The conjugated gels are sized and processed to produce an injectable, pH neutral, cohesive composition having a HA concentration of at least about 20 mg/g, for example, about 23, about 24 mg/g, about 25 mg/g, up to about 30 mg/g, and suitable for injection through a fine gauge needle. The gels have a G' value of at least about 50 PA, about 60 Pa, about 70 Pa, about 80 Pa up to, and no greater than about 100 Pa. The gels are packaged and sterilized using autoclave, UV light or other suitable means.

Each of the gels is useful for superficial injection, for example, injection into skin at a depth of no greater than about 1.0 mm, in a wrinkle of patients, for example, the periorbital region, nasolabial fold region, tear trough region, neck region, or any other facial region that would benefit from dermal filling. Despite the superficial introduction of the gels, no discoloration due to Tyndall effect is observed and the patients are satisfied with the results.

In closing, it is to be understood that although aspects of the present specification have been described with reference to the various embodiments, one skilled in the art will readily appreciate that the specific examples disclosed are only illustrative of the principles of the subject matter disclosed herein. Therefore, it should be understood that the disclosed subject matter is in no way limited to a particular methodology, protocol, and/or reagent, etc., described herein. As such, those skilled in the art could make numerous and various modifications or changes to or alternative configurations of the disclosed subject matter can be made in accordance with the teachings herein without departing from the spirit of the present specification. Changes in detail may be made without departing from the spirit of the invention as defined in the appended claims. Lastly, the terminology used herein is for the purpose of describing particular embodiments only, and is not intended to limit the scope of the present invention, which is defined solely by the claims. In addition, it is intended that all matter contained in the above description or shown in the accompanying drawings shall be interpreted as illustrative only and not limiting. Accordingly, the present invention is not limited to that precisely as shown and described.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing quantities of ingredients, properties such as molecular weight, reaction conditions, and so forth used in the specification and claims are to be understood as being modified in all instances by the term "about." As used herein, the term "about" means that the item, parameter or term so qualified encompasses a range of plus or minus ten percent above and below the value of the stated item, parameter or term. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

What is claimed is:

1. A method of treating fine lines of a face, the method comprising administering, to a dermal region of a patient, a dermal filler composition that exhibits no or insignificant Tyndall effect, the composition comprising ascorbic acid 2-glucoside (AA2G) covalently conjugated to hyaluronic acid via 1,4-butanediol diglycidyl ether (BDDE), wherein the hyaluronic acid is crosslinked via a crosslinking agent, and wherein the composition transmits at least 75% of visible light.

2. The method of claim 1 wherein the hyaluronic acid component is chemically conjugated to the AA2 with a degree of conjugation of between about 3 mol % and about 40 mol %.

3. The method of claim 1 wherein the hyaluronic acid component is chemically conjugated to the AA 2 with a degree of conjugation of between about 3 mol % and about 10 mol %.

4. The method of claim 1 wherein the administering comprises injecting the composition at a depth of no greater than about 0.8 mm.

5. The method of claim 1 wherein the administering comprises injecting the composition at a depth of no greater than about 0.6 mm.

6. The method of claim 1 wherein the administering comprises injecting the composition at a depth of no greater than about 0.4 mm.

7. The method of claim 1, wherein the crosslinking agent is BDDE.

8. The method of claim 1, wherein the composition has a storage modulus of between about 40 Pa and about 100 Pa.

9. The method of claim 1, wherein the composition has a storage modulus of about 80 Pa.

10. The method of claim 1, wherein the composition has a hyaluronic acid concentration of between about 18 mg/g and about 30 mg/g.

11. The method of claim 1, wherein the composition has a hyaluronic acid concentration of between about 12 mg/g and about 30 mg/g.

12. The method of claim 1, wherein the composition has a hyaluronic acid concentration of about 25 mg/g.

13. The method of claim 1, wherein the hyaluronic acid is at least 90 % low molecular weight hyaluronic acid.

14. The method of claim 1, wherein the hyaluronic acid has a mean molecular weight of between about 300 K Daltons and about 500 K Daltons.

15. The method of claim 1, wherein:
the composition has a degree of conjugation of about 10 mol %, and a storage modulus of about 60 Pa to about 80 Pa;
the hyaluronic acid has a mean molecular weight of between about 300 K Daltons and about 900 K Daltons; and
the crosslinking agent is BDDE.

16. The method of claim 1 wherein the composition transmits 75% to about 100% of the visible light.

* * * * *